United States Patent
Schaffer et al.

(10) Patent No.: US 12,054,700 B2
(45) Date of Patent: Aug. 6, 2024

(54) ILLUMINATION DEVICE FOR SPATIAL AND TEMPORAL CONTROL OF MORPHOGEN SIGNALING IN CELL CULTURES

(71) Applicant: The Regents of the University of California, Oakland, CA (US)

(72) Inventors: David V. Schaffer, Danville, CA (US); Nicole Anne Repina, Albany, CA (US); Ruoxing Lei, Berkeley, CA (US); Thomas Patrick C. McClave, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 200 days.

(21) Appl. No.: 17/608,896

(22) PCT Filed: May 6, 2020

(86) PCT No.: PCT/US2020/031707
§ 371 (c)(1),
(2) Date: Nov. 4, 2021

(87) PCT Pub. No.: WO2020/231707
PCT Pub. Date: Nov. 19, 2020

(65) Prior Publication Data
US 2022/0244184 A1     Aug. 4, 2022

Related U.S. Application Data

(60) Provisional application No. 62/847,684, filed on May 14, 2019.

(51) Int. Cl.
*G01N 21/64*     (2006.01)
*C12M 1/00*      (2006.01)
*C12M 1/32*      (2006.01)

(52) U.S. Cl.
CPC ............ *C12M 31/10* (2013.01); *C12M 23/12* (2013.01); *C12M 31/08* (2013.01);
(Continued)

(58) Field of Classification Search
CPC ...... C12M 31/10; C12M 23/12; C12M 31/08; C12M 31/02; C12M 41/06; G01N 21/6452; G01N 21/6486; G01N 2201/062
See application file for complete search history.

(56) References Cited

U.S. PATENT DOCUMENTS 5,785,116 A       7/1998   Wagner et al.
6,307,024 B1 *   10/2001   Novak ................... A61P 35/00
                                                              435/69.7
(Continued)

FOREIGN PATENT DOCUMENTS

CA        2560016      10/2005
CN      106975158       7/2017
(Continued)

OTHER PUBLICATIONS

Kupfer et al., "Advanced imaging approaches for regenerative medicine: Emerging technologies for monitoring stem cell fate in vitro and in vivo", Biotechnology Journal, vol. 10, pp. 1515-1528. (Year: 2015).*
(Continued)

*Primary Examiner* — Kiho Kim
(74) *Attorney, Agent, or Firm* — Rudy J. Ng; Bozicevic, Field & Francis LLP

(57) ABSTRACT

Provided are systems and methods for spatially and temporally controlling light with an illumination device comprising a light source operably connected to a circuit board, one or more light guide plates, one or more optical masks, a controller, and a computer readable medium, comprising instructions that, when executed by the controller, cause the
(Continued)

controller to: illuminate a cell or a substrate with light from the light source, and spatially and temporally control illumination of light to the cell or the substrate with one or more illumination parameters, wherein the one or more light guide plates provides uniform illumination of the light. Also provided herein are methods of screening using the system and/or device of the present disclosure.

19 Claims, 41 Drawing Sheets

(52) U.S. Cl.
CPC ..... *G01N 21/6452* (2013.01); *G01N 21/6486* (2013.01); *G01N 2201/062* (2013.01)

(56) References Cited

U.S. PATENT DOCUMENTS

| | | | |
|---|---|---|---|
| 6,337,435 | B1 | 1/2002 | Chu et al. |
| 9,091,447 | B2 | 7/2015 | Arrigoni et al. |
| 9,839,698 | B2 | 12/2017 | Yang et al. |
| 10,604,553 | B2 | 5/2020 | Heo et al. |
| 10,711,242 | B2 | 7/2020 | Deisseroth et al. |
| 2003/0082809 | A1* | 5/2003 | Quail ................ C12N 15/8237 435/254.2 |
| 2005/0095266 | A1 | 5/2005 | Perichaud et al. |
| 2006/0004306 | A1 | 5/2006 | Altshuler et al. |
| 2009/0057000 | A1 | 3/2009 | Kraus et al. |
| 2009/0186334 | A1* | 7/2009 | Young ................ C12N 5/0607 435/378 |
| 2011/0207209 | A1 | 8/2011 | Hammoms et al. |
| 2011/0216953 | A1 | 9/2011 | Callahan et al. |
| 2012/0004124 | A1 | 1/2012 | Schultze et al. |
| 2014/0099662 | A1 | 4/2014 | Ando et al. |
| 2015/0203837 | A1 | 7/2015 | Heo et al. |
| 2016/0326219 | A1 | 11/2016 | Riedler et al. |
| 2016/0328216 | A1 | 11/2016 | Leonelli et al. |
| 2016/0369222 | A1 | 12/2016 | Cho |
| 2017/0146720 | A1 | 5/2017 | Yamamoto et al. |
| 2019/0155146 | A1 | 5/2019 | Hribar et al. |
| 2020/0140821 | A1 | 5/2020 | Elfenbein et al. |
| 2021/0221858 | A1 | 7/2021 | Lee et al. |
| 2022/0017577 | A1* | 1/2022 | Kennedy ................ C12N 9/52 |
| 2022/0195371 | A1 | 6/2022 | Schaffer et al. |
| 2023/0105479 | A1 | 4/2023 | Lee et al. |

FOREIGN PATENT DOCUMENTS

| | | |
|---|---|---|
| CN | 112342241 A | 2/2021 |
| EP | 1964610 | 3/2008 |
| EP | 2682469 B1 | 12/2018 |
| WO | WO-2013185892 A1 | 12/2013 |
| WO | WO 2015/041219 | 3/2015 |
| WO | WO-2015086818 A1 | 6/2015 |
| WO | WO 2020/231707 | 11/2020 |
| WO | WO-2023004031 A1 | 1/2023 |
| WO | WO-2023235815 A1 | 12/2023 |

OTHER PUBLICATIONS

Follain et al., "Seeing is believing -multi-scale spatio-temporal imaging towards in vivo cell biology", Journal of Cell Science, vol. 130 pp. 23-38. (Year: 2017).*
Repina et al., (2017) "At Light Speed: Advances in Optogenetic Systems for Regulating Cell Signaling and Behavior", Annu Rev Chem Biomol Eng 8: 13-39.
Choi et al., (2021) "Novel Culture System via Wirelessly Controllable Optical Stimulation of the FGF Signaling Pathway for Human and Pig Pluripotency", Biomaterials 269, 11pages.
Kim et al., (2014) "Spatiotemporal Control of Fibroblast Growth Factor Receptor Signals by Blue Light", Chemistry & Biology 21: 903-912.
Li et al., (2018) "Spatiotemporal Control of TGF-β Signaling with Light", ACS Synth Biol. 7(2): 443-451.
Repina et al., (2020) "Engineered Illumination Devices for Optogenetic Control of Cellular Signaling Dynamics", Cell Reports 31, 107737, 17 pages.
Rost et al., (2017) "Optogenetic Tools for Subcellular Applications in Neuroscience", Neuron 96: 572-603.
Sokolik et al., (2015) "Transcription Factor Competition Allows Embryonic Stem Cells to Distinguish Authentic Signals from Noise", Cell Systems 1, 117-129.
Stroh et al., (2011) "Tracking Stem Cell Differentiation in the Setting of Automated Optogenetic Stimulation", Stem Cells 29(1):78-88.
Swartz et al., (2020) "Establishment of a Human Induced Pluripotent Stem Cell-Derived Neuromuscular Co-Culture Under Optogenetic Control", bioRvx 49 pages.
Tang et al., (2015) "A Flexible Reporter System for Direct Observation and Isolation of Cancer Stem Cells", Stem Cell Reports, vol. 4: 155-169.
Zhao et al., (2018) "Optogenetic Regulation of Engineered Cellular Metabolism for Microbial Chemical Production", Nature 555(7698): 683-687.
Amit, M et al.: Clonally Derived Human Embryonic Stem Cell Lines Maintain Pluripotency and Proliferative Potential for Prolonged Periods of Culture, Developmental Biology 227, 271-278 (2000).
Anzalone, et al., Search-and-replace Genome Editing Without Double-strand Breaks or Donor DNA. Nature 576(7785):149-157 (2019).
Beer, H D, et al., Fibroblast Growth Factor (FGF) Receptor 1-IIIb is a Naturally Occurring Functional Receptor for FGFs That is Preferentially Expressed in the Skin and the Brain. The Journal of Biological Chemistry 275(21):16091-7 (2000).
Bugaj, Lukasz J, et al., Optogenetic Protein Clustering and Signaling Activation in Mammalian Cells. Nature Methods 10(3):249-52 (2013).
Chatelle, C. et al., "A Green-Light-Responsive System for the Control of Transgene Expression in Mammalian and Plant Cells", ACS Synthetic Biology, 2018, vol. 7, pp. 1349-1358.
Chen, Guokai, et al., Chemically Defined Conditions for Human iPSC Derivation and Culture. Nature methods 8(5):424-9 (2011).
Chen, Guokai, et al., Thermal Stability of Fibroblast Growth Factor Protein is a Determinant Factor in Regulating Self-renewal, Differentiation, and Reprogramming in Human Pluripotent Stem Cells. Stem Cells 30(4):623-30 (2012).
Choi, In Young, et al., Concordant but Varied Phenotypes Among Duchenne Muscular Dystrophy Patient-specific Myoblasts Derived Using a Human Ipsc-based Model. Cell Reports 15(10):2301-2312 (2016).
Choi, In Young, et al., Transcriptional Landscape of Myogenesis From Human Pluripotent Stem Cells Reveals a Key Role of TWIST1 in Maintenance of Skeletal Muscle Progenitors. Elife 9:e46981 (2020).
Cong, et al., Multiplex Genome Engineering Using CRISPR/Cas Systems. Science 339(6121):819-823 (2013).
Dakhore, Sushrut, et al., Human Pluripotent Stem Cell Culture: Current Status, Challenges, and Advancement. Stem Cells International 2018:7396905 (2018).
De Santis et al. Self-organization of Human Dorsal-ventral Forebrain Structures by Light Induced SHH. Nature communications. vol. 12, 1 (2021):6768.
Deisseroth et al., "Next-Generation Optical Technologies for Illuminating Genetically Targeted Brain Circuits," The Journal of Neuroscience, 26(41), pp. 10380-10386 (Oct. 2006).
Dolgin, Elie, et al., Sizzling Interest in Lab-grown Meat Belies Lack of Basic Research. Nature 566(7743):161-162 (2019).
Ezashi, Toshihiko, et al., Derivation of Induced Pluripotent Stem Cells From Pig Somatic Cells. Proceedings of the National Academy of Sciences of the United States of America 106(27):10993-8 (2009).
Fenno et al., "The Development and Application of Optogenetics", Annu. Rev. Neumsci., (2011), vol. 34, pp. 389-412.

(56) References Cited

OTHER PUBLICATIONS

Furue et al., "Heparin Promotes the growth of human embryonic stem cells in a defined serum-free medium", Proc. Natl. Acad. Sci. U.S.A., (2008), vol. 105, No. 46, pp. 13409-13414.
Gao et al., "Establishment of porcine and human expanded potential stem cells", Nat Cell Biol, (Jun. 2019), vol. 21, pp. 687-699.
Gentile et al., "VEGF-mediated phosphorylation of eNOS regulates angioblast and embryonic endothelial cell proliferation", Dev. Biol , (2013), vol. 373, pp. 163-175.
Golonka, D. et al., "Deconstructing and repurposing the light-regulated interplay between Arabidopsis phytochromes and interacting factors", Communications Biology, 2019, vol. 2, No. 448, pp. 1-12.
Gramazio, S. et al., "Light-induced fermenter production of derivatives of the sweet protein monellin is maximized in prestationary *Saccharomyces cerevisiae* cultures", Biotechnology Journal, 2022, vol. 17, No. 2100676, pp. 1-10.
Grusch et al., "Spatio-temporally precise activation of engineered receptor tyrosine kinases by light", Embo J., (2014), , vol. 33, No. 15, pp. 1713-1726.
Huang et al., "Isolation and characterization of a Chlamydomonas gene that encodes a putative blue-light photoreceptor of the phototmpIn family", Physioi Plant, (2002), vol. 115, pp. 613-622.
Huang et al. Temporal Induction of Lhx8 by Optogenetic Control System for Efficient Bone Regeneration. Stem Cell Research & Therapy. vol. 12 (2021):339.
Ingles-Prieto et al., "Light-assisted small-molecule screening against protein kinases", Nature Chemical Biology., (Dec. 2015), vol. 11, pp. 952-954.
Itoh et al., "Evolution of the Fgf and Fgfr gene families", Trends Genet, (Nov. 2004), vol. 20, No. 11, pp. 563-569.
Johnson et al., "The Spatiotemporal Limits of Developmental Erk Signaling", Dev. Cell, (2017), vol. 40, pp. 185-192.
Kamm, et al. Perspective: The Promise Of Multi-Cellular Engineered Living Systems. APL Bioengineering. Vol. No. 2, Issue No. 4 (2018): pp. 040901-1-040901-21.
Karlin et al., Applications and statistics for multiple high-scoring segments in molecular sequences. PNAS USA 90(12):5873-5877 (1993).
Kennedy, et al., Rapid Blue-light-mediated Induction of Protein Interactions in Living Cells. Nature Methods 7(12):973-975 (2010).
Kim, et al., Spatiotemporal control of fibroblast growth factor receptor signals by blue light, 2014, Chemistry & Biology, 21, 7, 806-808 (Year: 2014).
Kinoshita et al., "phot1 and phot2 mediate blue light regulation of stomatal opening", Nature, (Dec. 6, 2001), vol. 414, pp. 656-660.
Kleinstiver et al. High-fidelity CRISPR-Cas9 nucleases with No. detectable genome-wide off target effects. Nature 529(7587):490-495 (2016).
Kriks et al., "Dopamine neurons derived from human ES cells efficiently engraft in animal models of Parkinson's disease", Nature, (Dec. 29, 2011 ), vol. 480, pp. 547-551.
Ledford, "Quest to Use CRISPR Gene Editing to Fight Disease Gains Ground", Nature, (Jan. 9, 2020), vol. 577, p. 156.
Lee, "Establishment of Light-inducibie control of stem cell fate", institute for Cell Engineering Department of Neurology & Neuroscience, Johns Hopkins University School of Medicine, 2018 System IMBA IMP Austria 2018 Vienna Conference (27 pages).
Levenstein, Mark E, et al., Basic Fibroblast Growth Factor Support of Human Embryonic Stern Cell Self-Renewal. Stem Cell 24(3):568-574 (2006).
Levskaya, Anselm, et al., Spatiotemporal control of cell signalling using a Light-switchable protein interaction. Nature 461:997-1001 (2009).
Lim, HoTae, et al., Profiling Individual Human Embryonic Stem Cells by Quantitative RT-PCR. Journal of Visualized Experiments (87) 6 pages (2014).
Liu, Hongta, et al., Photoexcited CRY2 Interacts with CIB1 to Regulate Transcription and Floral Initiation in Arabidopsis. Science 322:1535-1539 (2008).
Liu, HoTae, et al., Assessing cell-based animal proteins. Science 363(6429):825-827 (2019).
Lotz, Steven, et al., Sustained Levels of FGF2 Maintain Undifferentiated Stem Cell Cultures with Biweekly Feeding. PloS One 8(2):10 pages (2013).
Mali, et al. RNA-guided human genome engineering via Cas9. Science. Feb. 1, 20135;339(6121):823-6. doi: 10.1126/science. 1232033. Epub Jan. 3, 2013.
Mohammadi, et al., Identification of Six Novel Autophosphorylation Sites on Fibroblast Growth Factor Receptor 1 and Elucidation of Their importance in Receptor Activation and Signal Transduction. Molecular and Cellular Biology 16(3):977-989 (1996).
Motta-Mena, L.B et al., "An optogenetic gene expression system with rapid activation and deactivation kinetics", Nat Chem Biol, 2014, vol. 10, No. 3, pp. 196-202.
Muller, et al. Orthogonal Optogenetic Triple-gene Control In Mammalian Cells. ACS Synthetic Biology. Vol. No. 3, Issue No. 11 (2014): pp. 796-801.
Nagel, G. et al., "Channelrhodopsin-1: A Light-Gated Proton Channel in Green Algae," Science vol. 296, 2002, pp. 2395-2398.
Oh, Yohan, et al., Functional Coupling with Cardiac Muscle Promotes Maturation of hPSC-Derived Sympathetic Neurons. CellStem Cell 19:95-106 (2016).
Ornitz, D M, et al., Heparin is Required for Cell-Free Binding of Basic Fibroblast Growth Factor to a Soluble Receptor and for Mitogenesis in Whole Cells. Molecules and Cells 12:240-247 (1992).
Polstein et al. An Engineered Optogenetic Switch for Spatiotemporal Control Of Gene Expression, Cell Differentiation, and Tissue Morphogenesis. ACS Synthetic Biology. Vol 6, (2017): 17 pages.
Pomeroy, J.E., "Genetically Encoded Photoactuators and Photosensors for Characterization and Manipulation of Pluripotent Stem Cells", Theranostics, 2017, vol. 7, No. 14, pp. 3539-3558.
Porrello et al., "A symphony of stem cells in Vienna—looking to the future, 2018", The Company of Biologists, (2018), vol. 145, (6 pages).
Ran et al., Double Nicking by RNA-Guided CRISPR Cas9 for Enhanced Genome Editing Specificity. Cell 154: 1380-1389 (2013).
Reichhart et al., "A Phytochrome Sensory Domain Permits Receptor Activation by Red Light", Angewandte Chemie International Edition., (2016), vol. 55, pp. 6339-6342.
Repina et al. Optogenetic Control of Wnt Signaling for Modeling Early Embryogneic Patterning With Human Pluripotent Stem Cells. bioRxiv. (2019): pp. 1-61.
Reyes et al., "Activation of mitogen- and stress-activated kinase 1 is required for proliferation of breast cancer cells in response to estrogens or progestins", Oncogene, (2014), vol. 33, pp. 1570-1580.
Sako et al., "Optogenetic Control of Nodal Signaling Reveals a Temporal Pattem of Nodal Signaling Regulating Cell Fate Specification During Gastrulation", Cell Rep.; (2016), vol. 16, pp. 866-877.
Seale, P. et al., "PRDM16 Controls a Brown Fat/Skeletal Muscle Switch", Nature, 2008, vol. 454, No. 7207, pp. 961-967.
Sllimizu-Sato et al. . "A light-switchable gene promoter system", Nat. Biotechnol., (Oct. 2002), vol. 20, pp. 1041-1044.
Stadtrmauer et al, "CRISPR-engineered T ceils in patients with refractory cancer", Science, (2020), vol. 367, (14 pages).
Stockley et al., "Surpassing light-induced cell damage in vitro with novel cell culture media", Sci. Rep., (Apr. 12, 2017), vol. 7, (11 pages).
Takahashi et al., "Aureochome, a Photoreceptor required for photomorphogenesis in stramenopiles", Proc. Natl. Acad. Sci .U.S. A., (Dec. 4, 2007), vol. 104, No. 49, p. 19625- 19630.
Takahashi et al. Induction of Pluripotent Stem Cells from Adult Human Fibroblasts by Defined Factors. Cell 131:861-872 (2007).
Tesar et al, "New cell lines from mouse epiblast share defining features witll llurnan embryonic stem cells", Nature, (Jul. 12, 2007), vol. 448, pp. 196-199.
Thomson et al. Embryonic stem cell lines derived from human blastocysts. Science 282(5391):1145-1147 (1998).
Tischer et al. "Illuminating cell signalling witll optogenetic tools", Nat Rev. Mol Cell Bioi., (Aug. 2014), vol. 5, pp. 551-558.

(56) References Cited

OTHER PUBLICATIONS

Toyooka et al., "Photoreactions of Aureochrome-1", Biophys. J., (Jun. 2011), vol. 100, pp. 2801-2809.

Urakawa et al., "Klotho converts canonical FGF receptor into a specific receptor for FGF23", Nature, (Dec. 7, 2006), vol. 444, pp. 770-774.

Vater, C. et al., "Culture media for the differentiation of mesenchymal stromal cells", Acta Biomaterialia, 2011, vol. 7, pp. 463-477.

Vizoso, et al. A Doxycycline- And Light-inducible Cre Recombinase Mouse Model For Optogenetic Genome Editing. Nature Communications. vol. No. 13, Issue No. 1 (2022): 15 Pages.

Walker, E.J. et al., "Transcriptomic changes during TGF-β-mediated differentiation of airway fibroblasts to myofibroblasts", Scientific Reports, 2019, vol. 9, No. 20377, pp. 1-14.

Wang, H. et al., "Mini Photobioreactors for in Vivo Real-Time Characterization and Evolutionary Tuning of Bacterial Optogenetic Circuit", ACS Synth Biol., 2017, vol. 6, No. 9, pp. 1793-1796.

Weinberg, et al. High-Performance Chemical- And Light-Inducible Recombinases In Mammalian Cells And Mice. Nature Communications. vol. No. 10, Issue No. 1 (2019): 10 Pages.

West et al, "Porcine Induced Pluripotent Stem Cells Produce Chimeric Offspring", Stem Cells Dev., (2010), vol. 19, No. 8, pp. 1211-1220.

Wu et al., A genetically encoded photoactivatable Rac controls the motility of living cells. Nature. 461(7260): 104-108 (2009).

Wu Y et al. Directed Differentiation of Human iPSCs Into Mesenchymal Lineages by Optogenetic Control of TGF-B Signaling. Cell Reports, vol. 42, 5 (2023):112509.

Xie et al., "Optimization of a CRISPR/Cas9-mediated Knock-in Strategy at the Porcine Rosa26 Locus in Porcine Foetal Fibroblasts", Sci. Rep., (2017), vol. 7; (12 pages).

Xu et al., "CRISPR-Edited Stem cells in a Patient with HIV and Acute Lymphocytic Leukemia", N. Engl. J. Med., (Sep. 26, 2019), vol. 381, No. 13. pp. 1240-1247.

Yazawa et al, "Induction of protein-protein interactions in live cells using light", Nat. BiotechnoL, (Oct. 2009), vol. 27, No. 10, pp. 941-945.

Zhang et al. "Heat shock protein 27 promotes cell proliferation through activator protein-1 In lung cancer", Oncol. Lett; (2015), vol. 9, pp. 2572-2576.

Zhang et al., "Optogenetic control of intracellular signaling pathways", Trends Biotech no !. , (Feb. 2015), vol. 33, , No. 2, pp. 92-100.

\* cited by examiner

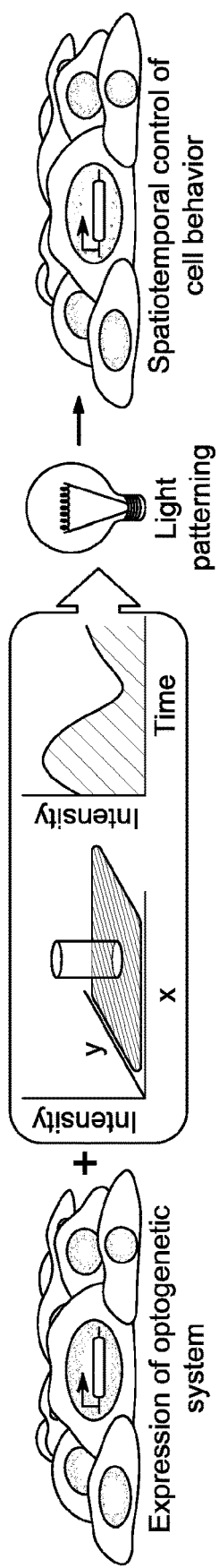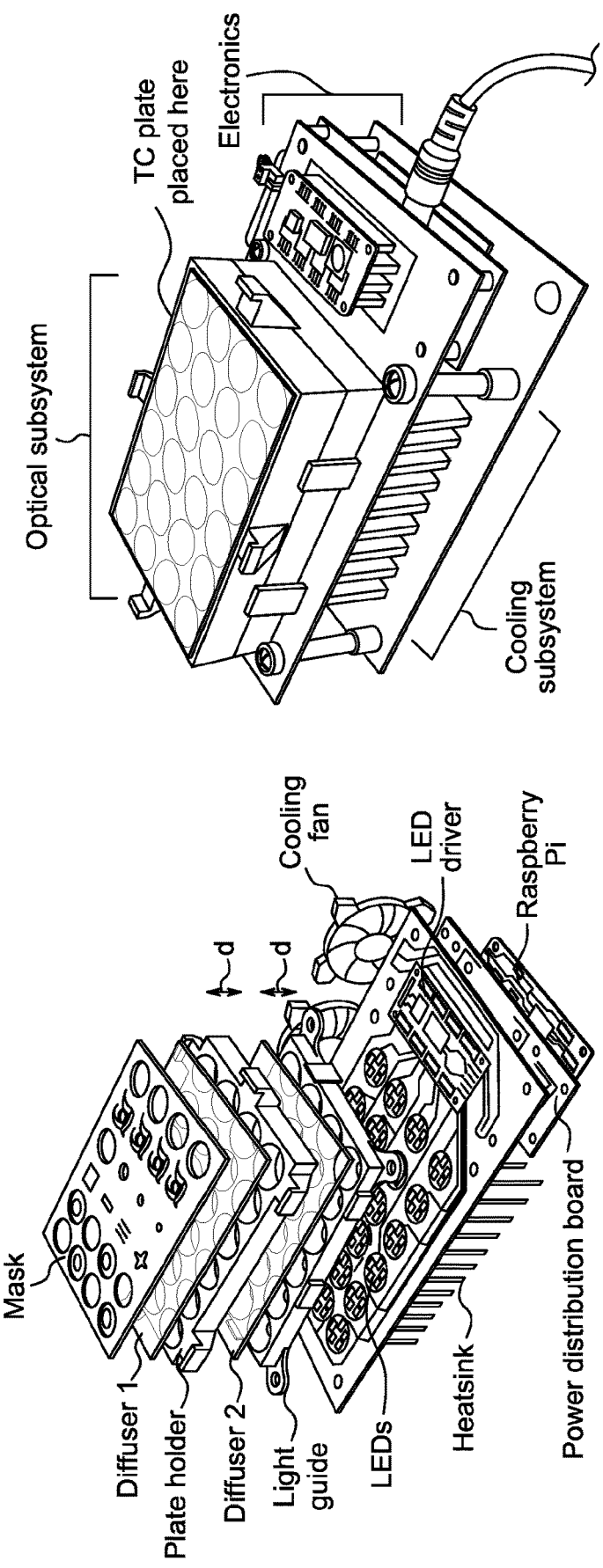
FIG. 1A
FIG. 1B
FIG. 1C

Light patterning

LED Controller

Plate Type
● 24 Plate Well

Overview (LED Preview)

Intensity / PWM Conversion

$I_{\mu W/mm^2}(x_{pwm}) = m x_{pwm} + b$ m = 0.005151   b = 0.0278

Interface Information:
Duty cycle = Percent time "on" per period.
Period = Length of blink cycle.
E.g. For 100ms blinks with 900ms pause, set duty cycle to 10% and period to 1s.
Function Max Sample Rate: 100 kHz (i.e. 100 ms)
Blink Min Period: 100 ms (i.e. 100 kHz)

Board Specifications:
- 24 Plate Well
- Raspberry Pi Zero W with Raspbian Stretch
- Adafruit TLC5947 LED Driver

| Channel: | Const | Blink | Func | I(µW/mm²) | $I_{min}$ | $I_{max}$ | Duty cycle | Period(s) |
|---|---|---|---|---|---|---|---|---|
| Channel A1: | ● | ○ | ○ | 0.5 | | | | |
| Channel A2: | ● | ○ | ○ | 0.5 | | | | |
| Channel A3: | ● | ○ | ○ | | | | | |
| Channel A4: | ○ | ● | ○ | | 0 | 2 | 50 | 2 |
| Channel A5: | ● | ○ | ○ | 2 | | | | |
| Channel A6: | ○ | ● | ○ | | 1 | 10 | 10 | 10 |
| Channel B1: | ○ | ○ | ● | 0.4 | | | | |
| Channel B2: | ● | ○ | ○ | | | | | |
| Channel B3: | ○ | ○ | ● | | | | | |
| Channel B4: | ● | ○ | ○ | | | | | |
| Channel B5: | ○ | ○ | ● | | | | | |
| Channel B6: | ● | ○ | ○ | 10 | | | | |
| Channel C1: | ● | ○ | ○ | | | | | |
| Channel C2: | ● | ○ | ○ | | | | | |
| Channel C3: | ○ | ● | ○ | | 0 | 5 | 1 | 0.1 |
| Channel C4: | ● | ○ | ○ | | | | | |
| Channel C5: | ● | ○ | ○ | | | | | |
| Channel C6: | ● | ○ | ○ | | | | | |
| Channel D1: | ● | ○ | ○ | 0.5 | | | | |
| Channel D2: | ● | ○ | ○ | | | | | |
| Channel D3: | ● | ○ | ○ | | | | | |
| Channel D4: | ● | ○ | ○ | 0.5 | | | | |
| Channel D5: | ● | ○ | ○ | | | | | |
| Channel D6: | ● | ○ | ○ | 0.5 | | | | |

Submit and Upload!

FIG. 8A

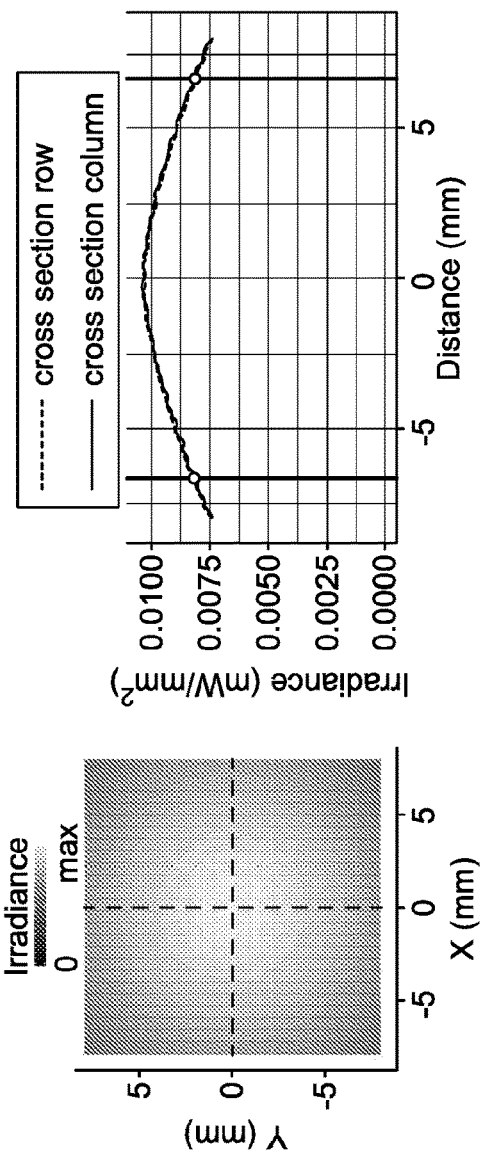
FIG. 9A
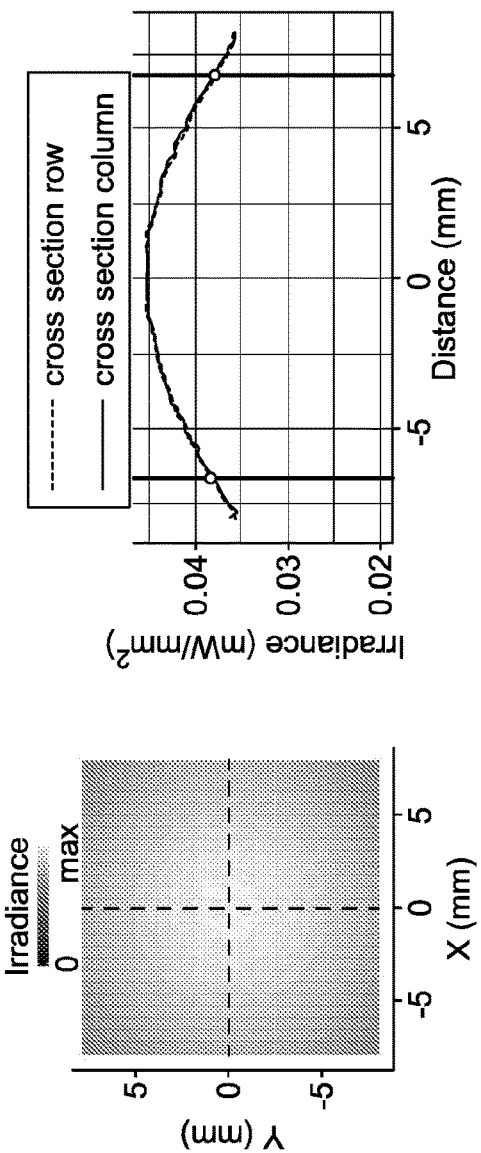
FIG. 9B
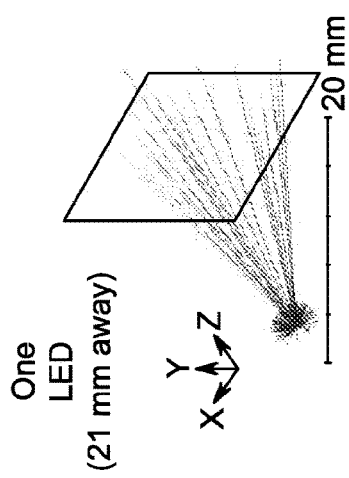
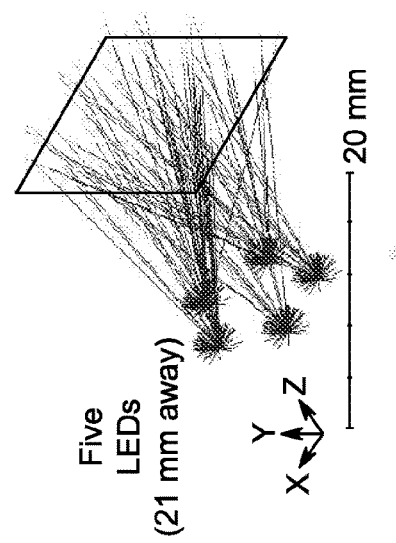

| | Object Type | ect | Insi | X Position | Y Position | Z Position | | Tilt Abo | Tilt Abo | Tilt Abo | Material |
|---|---|---|---|---|---|---|---|---|---|---|---|
| 1 | Cylinder Volume ▷ | 0 | 0 | 0.000 | 0.000 | 0.000 | | 0.000 | 0.000 | 0.000 | |
| 2 | Source Radial ▷ | 0 | 1 | 0.000 | 5.000 | 1.000E-03 | | 0.000 | 0.000 | 0.000 | - |
| 3 | Source Radial ▷ | 0 | 1 | 4.755 | 1.545 | 1.000E-03 | | 0.000 | 0.000 | 0.000 | - |
| 4 | Source Radial ▷ | 0 | 1 | 2.939 | -4.045 | 1.000E-03 | | 0.000 | 0.000 | 0.000 | - |
| 5 | Source Radial ▷ | 0 | 1 | -2.939 | -4.045 | 1.000E-03 | | 0.000 | 0.000 | 0.000 | - |
| 6 | Source Radial ▷ | 0 | 1 | -4.755 | 1.545 | 1.000E-03 | | 0.000 | 0.000 | 0.000 | - |
| 7 | Cylinder Volume ▷ | 1 | 0 | 0.000 | 0.000 | 15.000 | P | 0.000 | 0.000 | 0.000 | POLYC... |
| 8 | Cylinder Volume ▷ | 7 | 0 | 0.000 | 0.000 | 0.254 | P | 0.000 | 0.000 | 0.000 | LUMINI... |
| 9 | Cylinder Volume ▷ | 8 | 0 | 0.000 | 0.000 | 1.000E-02 | P | 0.000 | 0.000 | 0.000 | |
| 10 | Cylinder Volume ▷ | 9 | 0 | 0.000 | 0.000 | 15.000 | P | 0.000 | 0.000 | 0.000 | POLYC... |
| 11 | Cylinder Volume ▷ | 10 | 0 | 0.000 | 0.000 | 0.254 | P | 0.000 | 0.000 | 0.000 | LUMINI... |
| 12 | Rectangular Volume ▷ | 11 | 0 | 0.000 | 0.000 | 1.000E-02 | P | 0.000 | 0.000 | 0.000 | |
| 13 | Detector Rectangle ▷ | 12 | 0 | 0.000 | 0.000 | 0.501 | P | 0.000 | 0.000 | 0.000 | |

FIG. 16

| Front R | Z Length | Back R | Par 4(un) | Par 5(un) | Par 6(un) | Par 7(un) |
|---|---|---|---|---|---|---|
| 8.250 | 15.000 | 8.250 | | | | |
| 15 | 5E+06 | 14.400 | 1 | 0 | 1.000E-04 | 1.000E |
| 15 | 5E+06 | 14.400 | 1 | 0 | 1.000E-04 | 1.000E |
| 15 | 5E+06 | 14.400 | 1 | 0 | 1.000E-04 | 1.000E |
| 15 | 5E+06 | 14.400 | 1 | 0 | 1.000E-04 | 1.000E |
| 40.000 | 0.254 | 40.000 | | | | |
| 40.000 P | 1.000E-02 | 40.000 P | | | | |
| 8.250 P | 15.000 | 8.250 P | | | | |
| 40.000 | 0.254 | 40.000 | | | | |
| 40.000 P | 1.000E-02 | 40.000 P | | | | |
| 8.500 | 8.500 | 0.500 | 8.500 | 8.500 | 0.000 | 0 |
| 8.500 | 8.500 | 200 | 200 | 0 | 0 | |

Line Thickness

FIG. 16 (Cont'd)

ILLUMINATION DEVICE FOR SPATIAL AND TEMPORAL CONTROL OF MORPHOGEN SIGNALING IN CELL CULTURES

CROSS-REFERENCE

This application claims the benefit of U.S. Provisional Patent Application No. 62/847,684, filed May 14, 2019, which application is incorporated herein by reference in its entirety.

STATEMENT REGARDING FEDERALLY SPONSORED RESEARCH

This invention was made with government support under NS087253 awarded by the National Institutes of Health. The government has certain rights in the invention.

INTRODUCTION

Morphogen gradients are present throughout development and orchestrate the dynamic, coordinated movement and differentiation of cell populations. Spatially and temporally varying patterns of morphogens localize signaling to specific subpopulations of cells. Genetic perturbation and biomolecular treatment with pathway agonists or inhibitors have given immense insight into the key regulators of developmental progression, yet spatially-varying interactions between cell subpopulations and time-varying signal dynamics and thresholds remain largely unstudied, since such patterns of signaling are difficult to perturb and control in model developmental systems.

There is a need for optogenetic tools that control spatial and temporal patterns of light for high-throughput optogenetic screening.

SUMMARY

Provided are systems and methods for spatially and temporally controlling light with an illumination device comprising a light source operably connected to a circuit board, one or more light guide plates, one or more optical masks, a controller, and a computer readable medium, comprising instructions that, when executed by the controller, cause the controller to: illuminate a cell or a substrate with light from the light source, and spatially and temporally control illumination of light to the cell or the substrate with one or more illumination parameters, wherein the one or more light guide plates provides uniform illumination of the light. Also provided herein are methods of screening using the system and/or device of the present disclosure.

BRIEF DESCRIPTION OF THE DRAWINGS

FIG. 1, Panels A-C. Overview of illumination device, LAVA, for optogenetic stimulation of hESC cultures.

FIG. 16. Screenshot of Zemax model parameters of LAVA well, optimized for uniform 24-well illumination.

DEFINITIONS

Figure 2A:
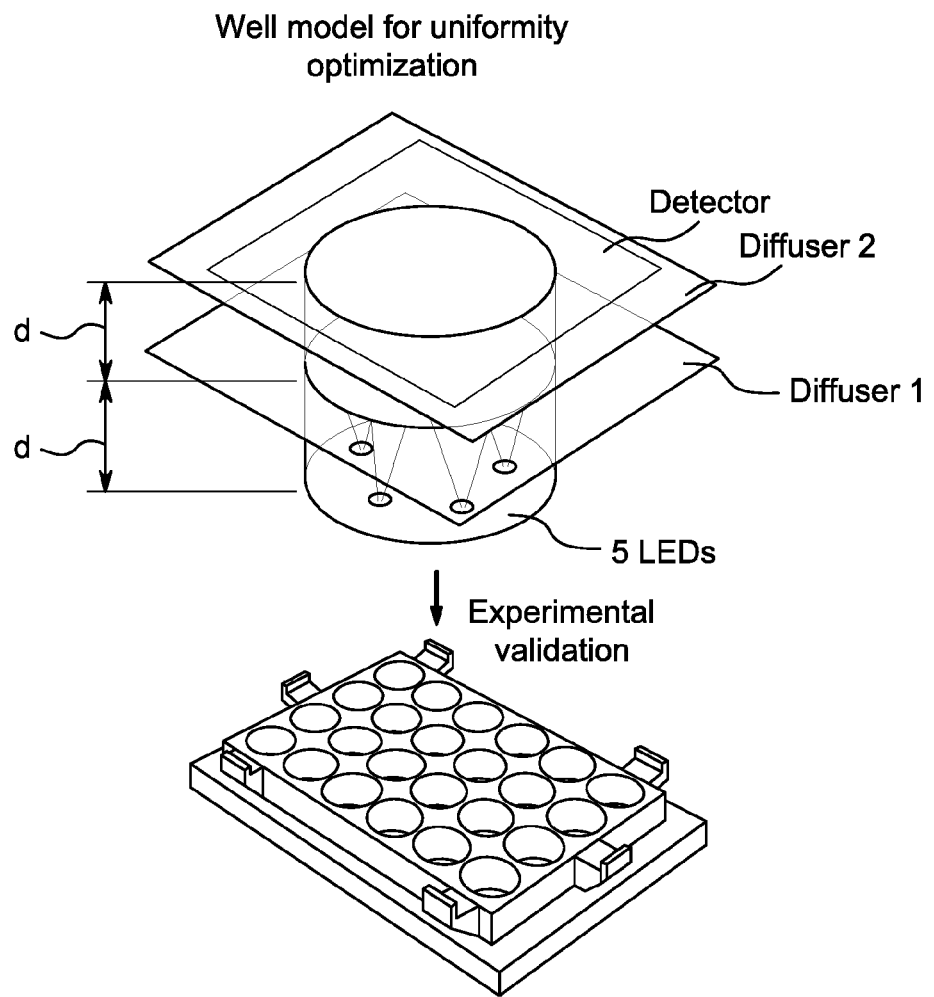
FIG. 2, Panels A-C. Optical design for illumination uniformity of tissue culture wells.

A "light guide plate" as used herein in its conventional sense, refers to a structure or material in which one or more light guides are positioned or formed therein.

A "light guide" as used herein in its conventional sense, refers to a structure or material that transmits illumination from a light source.

An "optical mask" as used herein in its conventional sense, refers to a substrate or material that selectively blocks a wavelength of light. However, an optical mask may have a region on the material in which light can pass through (e.g. aperture, core region, cut-out feature, etched feature).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs.

Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the optical mask" includes reference to one or more optical masks and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Provided are systems, devices, and methods for spatially and temporally controlling light with an illumination device comprising a light source operably connected to a circuit board, one or more light guide plates, one or more optical masks, a controller, and a computer readable medium, comprising instructions that, when executed by the controller, cause the controller to: illuminate a cell or a substrate with a light-based activation signal (e.g. light) from the light source, and spatially and temporally control illumination of light to the cell or the substrate with one or more illumination parameters, wherein the one or more light guide plates provides uniform illumination of the light. Also provided herein are methods of screening using the system and/or device of the present disclosure.

Systems and Devices

The present disclosure provides illumination devices and systems for spatially and temporally controlling light. According to aspects of the present disclosure, the illumination device includes a light source operably connected to a circuit board and configured to produce light; one or more light guide plates comprising one or more light guides; one or more optical masks positioned on a surface of one or more wells of a tissue culture plate; a controller, and a computer readable medium, that includes instructions that, when executed by the controller, cause the controller to illuminate the cell or the substrate with light from the light source; and spatially and temporally control illumination of light to the cell or the substrate in the one or more wells with one or more illumination parameters. In some aspects, the one or more light guides is configured to provide uniform illumination of the light in the one or more wells of the tissue culture plate. In some aspects, the illumination device is connected to a tissue culture plate comprising a cell or a substrate in one or more wells of the tissue culture plate.

Tissue Culture Plate

In some aspects, the illumination device is positioned adjacent to a culture plate. In some cases, the culture plate is a tissue culture plate (e.g. a cell culture plate or a multi-well plate). In some cases, the illumination device is reversibly connected to a tissue culture plate. By "adjacent", as used herein in its conventional sense to refer to be connected, linked, fastened, or positioned on a surface of the illumination device. In some cases, an illumination device positioned adjacent to a culture plate includes a gap or space between the tissue culture plate and the illumination device.

In some cases, the tissue culture plate includes one or more wells. In some cases, the tissue culture plate includes 24 wells. In some cases, the tissue culture plate includes % wells. In some cases, the tissue culture plate includes 384 wells.

In some cases, the tissue culture plate is made from an opaque polymer. In some cases, the tissue culture plate is made from a black polymer. In some cases, the tissue culture plate is made from a material that prevents light from bleeding through between the one or more wells.

In some cases, the tissue culture plate includes a coverglass bottom. In some cases, the one or more wells include a coverglass bottom. In some cases, the coverglass bottom has a thickness ranging from 150-200 µm. In some cases, the coverglass bottom has a thickness of about 150 µm, 160 µm, 170 µm, 180 µm, 190 µm, or 200 µm.

In some cases, the illumination device positioned adjacent to the tissue culture plate is configured to be placed in an incubator. In some cases, the illumination device positioned adjacent to the tissue culture plate placed in an incubator can be controlled wirelessly (e.g. controlled wirelessly without removing the illumination device positioned adjacent to the tissue culture plat from the incubator.

Light Source

In some cases, the illumination device includes a light source. In some cases, the light source is configured to product a light-based activation signal (e.g. light). In some cases, the light source is configured to be positioned adjacent to a circuit board. In some cases, the light source is operably adjacent to a circuit board. In some cases, the light source is configured to be connected to the circuit board.

In some cases, the light source can be a light emitting diode (LED). In some cases, the light source includes one or more LEDs. In some cases, the LED can generate white, blue, red, and/or green light. In some cases, the LED can generate amber and/or yellow light. In some cases, the LEDs are micro LEDs. In some cases, the LEDs are embedded into a circular array of the circuit board. In some embodiments, the light source is a solid state laser diode or any other means capable of generating light. The light generating means can generate light having an intensity sufficient to activate a cell, protein, and/or a substrate. In some cases, the light includes an irradiance (e.g. light after passing through the optics) having an intensity of any of about 0.005 $\mu W/mm^2$, 0.006 $\mu W/mm^2$, 0.0007 $\mu W/mm^2$, 0.008 $\mu W/mm^2$, 0.009 $\mu W/mm^2$, 0.01 $\mu W/mm^2$, 0.02 $\mu W/mm^2$, 0.03 $\mu W/mm^2$, 0.04 $\mu W/mm^2$, 0.05 $\mu W/mm^2$, 0.1 $\mu W/mm^2$, 0.2 $\mu W/mm^2$, 0.3 $\mu W/mm^2$, 0.4 $\mu W/mm^2$, 0.5 $\mu W/mm^2$, about 0.6 $\mu W/mm^2$, about 0.7 $\mu W/mm^2$, about 0.8 $\mu W/mm^2$, about 0.9 $\mu W/mm^2$, about 1.0 $\mu W/mm^2$, about 1.1 $\mu W/mm^2$, about 1.2 $\mu W/mm^2$, about 1.3 $\mu W/mm^2$, about 1.4 $\mu W/mm^2$, about 1.5 $\mu W/mm^2$, about 1.6 $\mu W/mm^2$, about 1.7 $\mu W/mm^2$, about 1.8 $\mu W/mm^2$, about 1.9 $\mu W/mm^2$, about 2.0 $\mu W/mm^2$, about 2.1 $\mu W/mm^2$, about 2.2 $\mu W/mm^2$, about 2.3 $\mu W/mm^2$, about 2.4 $\mu W/mm^2$, about 2.5 $\mu W/mm^2$, about 3 $\mu W/mm^2$, about 3.5 $\mu W/mm^2$, about 4 $\mu W/mm^2$, about 4.5 $\mu W/mm^2$, about 5 $\mu W/mm^2$, about 5.5 $\mu W/mm^2$, about 6 $\mu W/mm^2$, about 7 $\mu W/mm^2$, about 8 $\mu W/mm^2$, about 9 $\mu W/mm^2$, about 10 $\mu W/mm^2$, about 11 $\mu W/mm^2$, about 12 $\mu W/mm^2$, about 13 $\mu W/mm^2$, about 14 $\mu W/mm^2$, about 15 $\mu W/mm^2$, about 16 $\mu W/mm^2$, about 17 $\mu W/mm^2$, about 18 $\mu W/mm^2$, about 19 $\mu W/mm^2$, about 20 $\mu W/mm^2$, about 21 $\mu W/mm^2$, about 22 $\mu W/mm^2$, about 23 $\mu W/mm^2$, about 24 $\mu W/mm^2$, or about 25 $\mu W/mm^2$, inclusive, including values in between these numbers. In some cases, the light includes an irradiance having an intensity ranging from about 0.0001 to about 25 $\mu W/mm^2$, about 25 to 50 $\mu W/mm^2$, about 50-100 $\mu W/mm^2$, about 100-150 $\mu W/mm^2$, or 150-200 $\mu W/mm^2$. In other embodiments, the light-generating means produces light having a frequency of at least about 100 Hz. In some cases, the light source produces light having an intensity of any of about 0.05 $mW/mm^2$, 0.1 $mW/mm^2$, 0.2 $mW/mm^2$, 0.3 $mW/mm^2$, 0.4 $mW/mm^2$, 0.5 $mW/mm^2$, about 0.6 $mW/mm^2$, about 0.7 $mW/mm^2$, about 0.8 $mW/mm^2$, about 0.9 $mW/mm^2$, about 1.0 $mW/mm^2$, about 1.1 $mW/mm^2$, about 1.2 $mW/mm^2$, about 1.3 $mW/mm^2$, about 1.4 $mW/mm^2$, about 1.5 $mW/mm^2$, about 1.6 $mW/mm^2$, about 1.7 $mW/mm^2$, about 1.8 $mW/mm^2$, about 1.9 $mW/mm^2$, about 2.0 $mW/mm^2$, about 2.1 $mW/mm^2$, about 2.2 $mW/mm^2$, about 2.3 $mW/mm^2$, about 2.4 $mW/mm^2$, about 2.5 $mW/mm^2$, about 3 $mW/mm^2$, about 3.5 $mW/mm^2$, about 4 $mW/mm^2$, about 4.5 $mW/mm^2$, about 5 $mW/mm^2$, about 5.5 $mW/mm^2$, about 6 $mW/mm^2$, about 7 $mW/mm^2$, about 8 $mW/mm^2$, about 9 $mW/mm^2$, about 10 $mW/mm^2$, about 11 $mW/mm^2$, about 12 $mW/mm^2$, about 13 $mW/mm^2$, about 14 $mW/mm^2$, about 15 $mW/mm^2$, about 16 $mW/mm^2$, about 17 $mW/mm^2$, about 18 $mW/mm^2$, about 19 $mW/mm^2$. about 20 $mW/mm^2$, about 21 $mW/mm^2$, about 22 $mW/mm^2$, about 23 $mW/mm^2$, about 24 $mW/mm^2$. or about 25 $mW/mm^2$, inclusive, including values in between these numbers.

In some aspects, the light source can be externally activated by a controller. In some cases, the controller includes a processor. In some cases, the controller can include a power source which can be mounted to a transmitting coil. In some embodiments of the controller, a battery can be connected to the power source, for providing power thereto. A switch can be connected to the power generator, allowing an individual to manually activate or deactivate the power source.

In some cases, the controller is configured to independently illuminate each of the one or more wells of the tissue culture plate. In some cases, the one or more wells is independently illuminated by the one or more LEDs.

Circuit Board

In some aspects, the illumination device includes one or more circuit boards. In some cases, the light source is connected to the circuit board. In some cases, the light source includes one or more LEDs. In some cases, the circuit board is a printed circuit board (PCB). In some cases, the circuit board includes one or more circular arrays. In some cases, the illumination device includes a first circuit board (PCB1). In some cases, the PCB1 includes electronics for LED control. In some cases, the illumination device further comprises a power distribution board. In some cases, the illumination device includes a second circuit board (PCB2). In some cases, the PCB2 is a power distribution board. In some cases, the PCB1 contains solder pads for a circular array of 5 LEDs in order to emit light from the 5 LEDs to one well of the tissue culture plate (e.g. a 24 well tissue culture plate). In some cases, the 5 LEDs are positioned adjacent (e.g. connected to) to the circular array of the circuit board in series.

In some cases, the one or more LEDs (e.g. two or more, three or more, four or more, five or more, six or more, seven of more, eight or more, nine or more, or ten or more) are symmetrically and radially distributed on one or more circular arrays on the circuit board. In some cases, each of the one or more circular arrays has a radius ranging from about 2-10 mm (e.g. 2 mm, 3 mm, 4 mm, 5 mm, 6 mm, 7 mm, 8 mm, 9 mm, or 10 mm). In some cases, each of the one or more circular arrays has a radius of about 5 mm.

In some cases, the circuit board includes 5 LEDs symmetrically and radially distributed on each of the one or more circular arrays of the circuit board. In some cases, the circuit board includes 24 circular arrays. In some cases, the one or more circular arrays is positioned below the one or more wells of the tissue culture plate. In some cases, one or more LEDs (e.g. two or more, three or more, four or more, five or more, seven or more, eight or more, nine or more, or ten or more) on each of the one or more circular arrays are configured to illuminate one well of the one or more wells in the tissue culture plate. In some cases, the 5 LEDs on each of the one or more circular arrays are configured to illuminate one well of the one or more wells in the tissue culture plate. In some cases, five or more LEDs on each of the one or more circular arrays are configured to illuminate one well of the one or more wells in the tissue culture plate.

In some cases, the circuit board includes 1 LED symmetrically and radially distributed on each of the one or more circular arrays of the circuit board. In some cases, the circuit board includes 96 circular arrays. In some cases, the 1 LED is positioned at approximately the center of each circular array.

In some cases, the one or more LEDs on the circuit board are positioned below the one or more wells of the tissue culture plate.

In some aspects, the illumination device includes a heat sink mounted on the circuit board. In some cases, the heat sink is mounted on the circuit board with a thermally conductive adhesive. In some cases, the heat sink is mounted onto the bottom surface of the first circuit board (e.g. PCB1). In some cases, the heat sink is mounted using a thermally conductive adhesive. In some cases, the thermally conductive adhesive is Artic Silver, ASTA-7G. In some cases, the heat sink is mounted onto the circuit board (e.g. first circuit board) in a region without silk screen and thermally conductive electrical vias that draw heat away from the one or more LEDs.

In some cases, the illumination device includes a cooling fan. In some cases, the illumination device includes one or more cooling fans. In some cases, the illumination device includes two cooling fans. In some cases, the illumination device includes three cooling fans. In some cases, the one or more cooling fans is positioned on the outer edges of the circuit board. In some cases, the first circuit board includes headers for electrical connection to the one or more cooling fans.

In some aspects, the illumination device is connected to a power supply. In some cases, the illumination device is operably connected to the power supply. In some cases, the illumination device is electrically connected to the power supply. In some cases, the power supply connects to the second circuit board (e.g. PCB2) of the illumination device. In some cases, power is supplied to the one or more cooling fans and the controller through switching voltage regulators.

Controller

In some aspects, the illumination device includes a controller. In some cases, the controller is configured to independently illuminate each of the one or more wells.

In some cases, the controller is a microcontroller. In some cases, the controller is a Raspberry Pi microcontroller. In some cases, the tissue culture plate is mounted in a position on the illumination device such that the tissue culture plate is illuminated from the bottom.

In some cases, the controller further includes one or more LED drivers. In some cases, the LED driver includes one or more channels. In some cases, the LED driver is a 24-channel LED driver. In some cases, the LED driver is a 96-channel LED driver. In some cases, the LED driver is a 384-channel LED driver. In some cases, the illumination device includes two or more, three or more, four or more, five or more, six or more, seven or more, eight or more, nine or more, or ten or more LED drivers. In some cases, the illumination device includes four LED drivers. In some cases, the controller provides for independent control of each of the channels of the LED driver (e.g. a 24-channel LED driver, a 96 channel LED driver, or a 384-channel LED driver). In some cases, the controller is configured to independently illuminate each of the one or more wells of the tissue culture plate.

In some cases, the device is connected to a power supply. In some cases, the power supply is connected to the LED driver of the illumination device. In some cases, the power supply connects to the second circuit board through a barrel power jack to power the one or more LEDs through the LED driver.

In some cases, the LED driver is electrically connected to the circuit board. In some cases, the LED driver is mounted and electrically connected to the first circuit board of the illumination device. In some cases, the microcontroller is mounted and electrically connected to the first circuit board. In some cases, the second circuit board (e.g. PCB2) is mounted and electrically connected to the first circuit board (PCB1).

In some cases, the LED driver is a 24-channel LED driver. The LED driver is configured to control the one or more LEDs. In a non-limiting example, for 24-well illumination (e.g. illumination of 24 wells in a 24 tissue culture plate), a first circuit board includes 24 circular arrays containing 5 LEDs radially and symmetrically distributed on each of the 24 circular arrays. In some cases, the 24-channel LED driver can independently control illumination of each well in the 24 tissue culture plate, wherein each channel of the LED driver controls one well in the 24 well plate. Another non-limiting example includes 96-well illumination (e.g. illumination of 96 wells in a 96 tissue culture plate), a first circuit board includes 96 circular arrays containing 1 LED radially and symmetrically distributed on each of the 96 circular arrays. In some cases, the illumination device can illuminate 24 independent channels, wherein each channel controls 4 wells of the 96 well plate. In some cases, the illumination device includes four LED drivers, each containing 24 channels. In such cases, the four LED drivers, combined, include 96 independent channels, wherein each channel controls one well of the 96 wells in the tissue culture plate. In some cases, the four LED drivers are operatively connected together to provide independent control of each well in the 96 wells of the tissue culture plate.

In some cases, the illumination device positioned adjacent to the tissue culture plate is mounted onto a material through vibration-dampening mounts. A non-Limiting example of the material may include an acrylic, plastic, metal, or composite material or any material that is secure enough to constitute a base. In some cases, the acrylic material is an acrylic laser-cut base. In some cases, the vibration-dampening mounts include rubber footpegs. In some cases, the vibration-dampening mounts are configured to reduce static or electrical shorting with the tissue culture incubation racks.

Light Guide Plates

Aspects of the present disclosure include an illumination device including one or more light guide plates. In some cases, the light guide plates include one or more light guides. In some cases, the one or more light guides are configured to produce a spatial pattern. By "arc of light", as used herein, refers to the shape of the spatial pattern that is cut in the optical mask, used to illuminate the sample (e.g. cell or substrate). In some cases, the shape of the spatial pattern is a curved line (e.g., an arc) cut in the optical mask. In some cases, the one or more light guide plates comprises a first light guide plate and a second light guide plate. In some cases, the first light guide and the second light guide can include light guides that are the same form of each other (e.g. made from the same material, and/or have the same dimensions, etc.). In some cases, the first light guide and the second light guide can include light guides that are different forms of each other (e.g. made from different materials, and/or have different dimensions, etc.)

In some cases, the one or more light guide plates include one or more light guides. In some cases, the one or more light guides comprises 24 light guides, 96 light guides, or 384 light guides. In some cases, the illumination device has one or more light guides within each of the one or more light guide plates. For example, in some cases, the light guides within each of the one or more light guide plates are held in an array by a surrounding frame of the light guide plate. In some cases, the illumination device has 24 light guides held in an array by a surrounding frame of the light guide plate. In some cases, the illumination device has 96 light guides held in an array by a surrounding frame of the light guide plate. In some cases, the illumination device has 384 light guides held in an array by a surrounding frame of the light guide plate.

In some cases, the one or more light guides has a diameter of about 5 or more mm, about 6 or more mm, about 7 or more mm, about 8 or more mm, about 9 or more mm, about 10 or more mm, about 11 or more mm, about 12 or more mm, about 13 mm or more, about 15 mm or more, about 16 mm or more, about 17 mm or more about 18 mm or more, about 19 mm or more, or about 20 mm or more. In some cases, the one or more light guides has a diameter of about 16 or more mm. In some cases, the one or more light guides has a radius of about 8.25 mm. In some cases, the one or more light guides has a diameter of about 7 mm. In some cases, the one or more light guides has a diameter of about 16.5 mm.

In some cases, the one or more light guides has a thickness ranging from 0.5 cm to about 5 cm. In some cases, the one or more light guides has a thickness of about 0.5 cm, about 1 cm, about 1.5 cm, about 2 cm, about 2.5 cm, about 3 cm, about 3.5 cm, about 4 cm, about 4.5 cm, or about 5 cm. In some cases, the one or more light guides has a thickness ranging from 1 cm to 1.5 cm. In some cases, the one or more light guides has a thickness of about 1.5 cm.

In some cases, the one or more light guides can be of a circular shape and/or other shapes as required per conditions specific to its intended use. In some cases, the one or more light guides comprises a circular shape. In some cases, the one or more light guides comprises a cylindrical shape, a circular shape, a square shape, a spherical shape, a cone-shape, a prism-shape, or a rectangular shape. In some cases, each of the light guides is the same shape. In some cases, each of the light guides is a different shape. The light guides are not limited to the shapes and/or sizes as described herein and can be any shape and/or size as required per conditions specified to its intended use.

In some cases, the one or more light guide plates and/or light guides is transparent and made from a material selected from glass, acryl, plastic, polymethylmethacrylate (PMMA), poly-lactic acid (PLA), and epoxy. In some cases, the one or more light guide plates and/or light guides is opaque except for the region of the light guide through which light passes through (e.g. the center of the light guide). In some cases, the one or more light guide plates and/or light guides is only transparent in the center of the light guide through which light passes through.

In some cases, the one or more light guide plates is made from a polymer. In some cases, the polymer is acrylic or PLA. In some cases, the one or more light guides include a reflective coating.

In some cases, the one or more light guides is configured to directly receive only light that is generated from the one or more LEDs positioned in the one or more circular arrays of the circuit board. In some cases, each of one or more light guides is positioned to provide for selective illumination for each of the one or more wells of the tissue culture plate.

In some cases, the first light guide plate is connected to the circuit board (e.g. the first circuit board or the second circuit board).

In some cases, the illumination uniformity of the light beam from light emitted by the light source is proportional to the thickness of the one or more light guides. In some cases, increasing the thickness of the light guide. In some cases, increasing the thickness of the light guide from 1 cm to 1.5 cm decreases the difference between the edge and center intensities of the one or more wells of the one or more wells. In some cases, the one or more light guides improves the illumination uniformity by about 10% or more, 20% or more, 30% or more, 40% or more, 50% or more, 60% or more, or 70% or more as compared to an illumination device without a light guide.

In some cases, the light guide is configured to decrease the variability of light intensity of the light beam emitted from the light source between each of the one or more wells of the tissue culture plate.

Optical Diffusers

In some aspects, the illumination device includes one or more optical diffusers. In some cases, the one or more optical diffusers comprises a first optical diffuser and a second optical diffuser.

In some cases, the first light guide plate is positioned between the first and second optical diffuser. However, optical elements beside diffusers can also be used to collimate the light to make the light beam more uniform. A non-limiting example of an optical element other than a diffuser includes Fresnel lenses, which is a lens that takes the shape of a flat sheet and can be used instead of a diffuser to collimate the light.

In some cases, the one or more optical diffusers comprises one or more 80° circular optical diffusers. Optical diffusers can be any material that diffuses or scatters light. In some cases, the one or more optical diffusers and light guides control the uniformity and intensity of the signals being projected onto the cell or substrate. In some cases, the one or more diffusers include one or more 80° diffuser coatings (e.g. scatter coating, full width-half max). In some cases, the diffuser coating is coated on a polycarbonate material. In some cases, the polycarbonate has a thickness of about 0.1 inches. However, the one or more diffusers are not limited to 80° diffuser coatings and can be any known diffuser coating applied to different substrates.

In some cases, the first optical diffuser is positioned between the tissue culture plate and the first light guide plate. In some cases, the second optical diffuser is positioned between the first light guide plate and the second light guide plate. In some cases, the first optical diffuser and the second optical diffuser can include optical diffusers that are the same form of each other (e.g. made from the same material, and/or have the same dimensions, etc.). In some cases, the first optical diffuser and the second optical diffuser can include optical diffusers that are different forms of each other (e.g. made from different materials, and/or have different dimensions, etc.)

Optical Masks

In some cases, the illumination device includes one or more optical masks. In some cases, the one or more optical masks are configured to selectively block a wavelength of light outside of a core region of the one or more optical masks from reaching a detector to detect the light. In some cases, the one or more optical masks is configured to block a wavelength of light from reaching the illuminated sample or substrate.

In some cases, the one or more optical masks includes an aperture. In some cases, the one or more optical masks includes one or more cut-out features. In some cases, the one or more cut-out features includes a patterned cut-out feature.

In some cases, the one or more patterned cut-out features includes a core region. In some cases, the core region includes a pattern size ranging from 10-600 µm. In some cases, the core region includes a pattern size ranging from 50-500 µm. In some cases, the core region includes a pattern size of about 50 or more µm, 100 or more µm, 150 or more µm, 200 or more µm, 250 or more µm, 300 or more µm, 350 or more µm, 400 or more µm, 450 or more µm, 500 or more µm, 550 or more µm, or 600 or more µm.

In some cases, the one or more patterned cut-out features is a slit. In some cases, the one or more patterned cut-out features is a curved slit (e.g., an arc). In some cases, the one or more patterned cut-out features is a circle, rectangle, square, or triangle. In some cases, the patterned cut-out feature can be of a slit shape and/or other shapes as required per conditions specific to its intended use.

In some cases, the one or more optical masks is configured to selectively block the passage of light outside of the core region.

In some cases, the one or more optical masks are made of an opaque material. In some cases, the core region of the one or more optical masks does not include the opaque material from which the optical mask is made from (e.g. the core region includes an aperture or a patterned slit in the material). In some cases, the one or more optical masks include a combination of a transparent material and an opaque material. In some cases, the combination of a transparent material and an opaque material provides for greyscale modulation of the light pattern. In some cases, the core region of the optical mask includes a transparent material, and the material outside of the core region is an opaque material.

In some cases, the one or more optical masks is adhered to the one or more wells of the tissue culture plate. In some cases, the one or more optical masks is positioned on a surface of one or more wells of the tissue culture plate. In some cases, the one or more optical masks is positioned on a bottom surface of the one or more wells. In some cases, the one or more optical masks is positioned on a bottom outer surface of the one or more wells. In some cases, the core region of the one or more optical masks is positioned in the center of an outer surface of the one or more wells. In some cases, the one or more optical masks is positioned on the one or more wells of the tissue culture plate. In some cases, the one or more optical masks is positioned on an outer surface of the coverglass bottom. In some cases, the one or more optical masks is positioned at a distal end (e.g. the closed-ended outer surface of the one or more wells) of the one or more wells of the tissue culture plate relative to an open ended surface of the one or more wells. In some cases, the one or more optical masks is positioned on a surface of one or more wells of the tissue culture plate.

In some cases, the one or more optical masks includes an optical mask positioned on each of the one or more wells of the tissue culture plate. In some cases, the one or more optical masks comprises 24 optical masks, each mask positioned on each of the 24 wells of the tissue culture plate. In some cases, the one or more optical masks includes an optical mask positioned on each of the one or more wells of the tissue culture plate. In some cases, the one or more optical masks comprises 96 optical masks, each mask positioned on each of the 96 wells of the tissue culture plate. In some cases, the one or more optical masks includes an optical mask positioned on each of the one or more wells of the tissue culture plate. In some cases, the one or more optical masks comprises 384 optical masks, each mask positioned on each of the 384 wells of the tissue culture plate.

In some cases, the optical mask includes a photo mask or an intensity mask. An optical mask can include a material, coating, and/or plate with holes or transparencies that allow light to pass through in a defined pattern. In some cases, the optical mask absorbs light to varying degrees and can be patterned as required per conditions specific to its intended use. In some cases, the optical mask is an intensity mask. In some cases, the intensity mask is fully absorbing (e.g. opaque, dark), or not absorbing (e.g. transparent, bright), or a combination thereof. In some cases, the intensity mask is made from adhesive vinyl. In some cases, the adhesive vinyl is polyvinyl chloride (PVC). In some cases, the intensity mask is made from Biaxially Oriented Polypropylene.

In some cases, the optical mask is a phase mask. In some cases, the phase mask is a phase shift mask. A phase mask is used to modulate the phase of light in order to change the light intensity. The phase modulation results in constructive and destructive interference that generates a pattern of light intensity, which can be similar to a light pattern generated with an intensity mask. It can be used in combination with an intensity mask, which is then called a phase-shift mask. In some cases, the phase mask is made from glass (e.g. quartz).

In some cases, the illumination pattern when the light beam contacts the one or more wells includes a 0.5 mm diameter of light, 1.0 mm diameter of light, 1.5 mm diameter of light, or a 2 mm diameter of light emitted to the one or more wells. In some cases, the illumination pattern includes a 1.5 mm diameter of light emitted to the one or more wells.

Detector

In some aspects, the illumination device includes one or more detectors. In some aspects, the illumination device can be used in combination with a microscope, a spectrophotometer, a detector, or a robotic handler. Non-limiting examples of microscopes include a fluorescence microscope, a confocal laser scanning microscope, and/or a bright-field microscope), a spectrophotometer, or a detector. In some cases, the detector is a photomultiplier tube, a charged coupled device (CCD), or a complementary metal oxide semiconductor (CMOS) sensor. In some cases, the detectors of interest are configured to measure collected light at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths. In some embodiments, detectors are configured to measure collected light over a range of wavelengths (e.g., 200 nm to 1000 nm). In some embodiments, detectors are configured to collect spectra of light over a range of wavelengths. In some embodiments, an optical imaging system may include one or more detectors configured to collect spectra of light over one or more of the wavelength ranges of 200 nm to 1000 nm. In some embodiments, detectors are configured to measure light emitted by a cell or substrate in the one or more wells of a tissue culture plate at one or more specific wavelengths. For example, the one or more detectors are configured to measure light at one or more of 350 nm, 370 nm, 400 nm, 410 nm, 450 nm, 518 nm, 519 nm, 561 nm, 578 nm, 605 nm, 607 un, 625 nm, 650 nm, 660 nm, 667 nm, 670 nm, 668 nm, 695 nm, 710 nm, 723 nm, 780 nm, 785 nm, 647 nm, 617 un and any combinations thereof. In some embodiments, one or more detectors may be configured to be paired with specific fluorophores, such as those used in a fluorescence assay.

In some cases, the one or more detectors is positioned about 5 or more mm away from the light source. In some cases, the one or more detectors is positioned about 10 mm or more, 15 mm or more, 20 mm or more, or 25 mm or more away from the light source. In some cases, the one or more detectors is positioned 21 mm away from the light source.

Graphical User Interface (GUI)

In some cases, the illumination device can be controlled with a graphical user interface (GUI) to communicate wirelessly with the controller of the illumination device. In some cases, the GUI can be used to program the illumination parameters of the one or more wells. In some cases, the GUI can be used to wirelessly program the illumination intensity and temporal (e.g. time) sequences of each of the one or more wells. In some cases, the GUI provides for a user to input a desired illumination parameter for each of the one or more wells. In some cases, the GUI provides for wireless upload of the illumination parameters to the controller (e.g. the microcontroller and/or the LED driver) on the illumination device.

In some cases, the GUI allows the user to set each channel of the LED driver (e.g. in a 24 channel LED driver or a 96-channel LED driver) with one or more illumination parameters. In some cases, the GUI allows the user to set each channel to, for example, constant illumination at a specified intensity; blinking illumination at a specified intensity, duty cycle, and time period; and a series of linear or sinusoidal functions at specified illumination parameters.

In some cases, the GUI provides for multiple piecewise functions that can be programmed in a time sequence.

Illumination Parameters

In some cases, the illumination device can spatially and temporally control illumination of a cell or a substrate with one or more illumination patterns.

In some cases, the illumination parameters can include, but are not limited to, frequency of light emitted from the light source, duty cycle, duration of light emitted from the light source, and specific patterns of illumination (e.g. pulsed illumination). In some cases, the one or more illumination parameters is selected from an illumination intensity, an illumination duration, an illumination pattern, and a combination thereof.

In some cases, the illumination intensity ranges from about 0.005 $\mu W/mm^2$ to about 20 $\mu W/mm^2$. In some cases, the illumination intensity ranges from about 0.005 $\mu W/mm^2$ to about 10 $\mu W/mm^2$. In some cases, the illumination intensity ranges from about 0.005 $\mu W/mm^2$ to about 20 $mW/mm^2$.

In some cases, the illumination pattern is a pulsing pattern, where light is pulsed in a millisecond time frame. In some cases, an illumination duration ranges from about 0.5 or more ms, 1 or more ms, 2 or more ms, 3 or more ms, 4 or more ms, 5 or more ms, 6 or more ms, 7 or more ms, 8 or more ms, or 10 or more ms. In some cases, the pulsed illumination includes a pulse duration of 1 or more ms.

In some cases, the illumination pattern is a pulsing pattern, where light is pulsed in a millisecond time frame. In some cases, the illumination device further includes a pulse generator configured to pulse the light emitted from the light source.

In some cases, the illumination pattern includes a sinusoidal or linear pattern with a pulsing frequency of 1 or more Hz.

In some cases, the illumination pattern includes a blinking pattern with a pulsing frequency of about 1 or more Hz, 10 or more Hz, 20 or more Hz, 30 or more Hz, 40 or more Hz, 50 or more Hz, 60 or more Hz, 70 or more Hz, 80 or more Hz, 90 or more Hz, 100 or more Hz, 100 or more Hz, 110 or more Hz, 120 or more Hz, 130 or more Hz, 140 or more Hz, or 150 or more Hz. In some cases, the illumination pattern includes a blinking pattern with a pulsing frequency of about 100 Hz.

In some cases, the illumination pattern includes a 0.5 mm diameter of light, 1.0 mm diameter of light, 1.5 mm diameter of light, or a 2 mm diameter of light emitted to the one or more wells. In some cases, the illumination pattern includes a 1.5 mm diameter of light emitted to the one or more wells (e.g. the diameter of the light beam when it contacts the one or more wells).

In some cases, the illumination duration includes illumination of the one or more wells for 1 or more hours. In some cases, the illumination duration includes illumination of the one or more wells for 1 or more weeks. In some cases, the illumination duration ranges from about 0.5 or more ms, 1 or more ms, 2 or more ms, 3 or more ms, 4 or more ms, 5 or more ms, 6 or more ms, 7 or more ms, 8 or more ms, or 10 or more ms. In some cases, the illumination duration ranges from about 0.5 or more s, 1 or more s, 2 or more s, 3 or more s, 4 or more s, 5 or more s, 6 or more s, 7 or more s, 8 or more s, or 10 or more s. In some cases, the illumination duration ranges from about 1 or more minutes, 2 or more minutes, 3 or more minutes, 4 or more minutes, 5 or more minutes, 6 or more minutes, 7 or more minutes, 8 or more minutes, or 10 or more minutes.

In some cases, the one or more wells can be illuminated with red, amber, yellow, green, blue, or white light. In some cases, the GUI can set the color of light corresponding to a specific wavelength.

In some cases, the GUI allow the user to set a wavelength of light for which light can be emitted. In some cases, the light can have a wavelength ranging from 200 to 1000 nm. In some cases, the light can have a wavelength ranging from about 350 to about 410 nm. In some cases, the light can have a wavelength of about 470 nm and about 510 nm or can have a wavelength of about 490 nm. In some cases, the light can have a wavelength of about 470 nm. In some cases, the light can have a wavelength of about 445 nm. In some cases, the light can have a wavelength ranging from about 530 to about 595 nm. In some cases, the light can have a wavelength of about 530 nm. In some cases, the light can have a wavelength of about 560 nm. In some cases, the light can have a wavelength of about 542 nm. In some cases, the light can have a wavelength of about 546 nm. In some cases, the light can have a wavelength ranging from about 580 and 630 nm. In some cases, the light can be at a wavelength of about 589 nm or the light can have a wavelength greater than about 630 nm (e.g. less than about 740 nm). In another embodiment, the light has a wavelength of around 630 nm.

A device of the present disclosure can be part of a system that provides for spatial and temporal control of light using the illumination device. For example, in some cases, a system of the present disclosure includes: an illumination device of the present disclosure; a tissue culture plate including one or more wells; and one or more of: i) a microscope; ii) a spectrophotometer; iii) a detector; iv) a power source; v) a cooling fan; vi) a heat sink; vii) a graphical user interface; and viii) computer hardware and software for controlling the illumination device.

Methods

The present disclosure provides methods for spatially and temporally controlling light using the system and/or illumination devices of the present disclosure. According to aspects of the present disclosure, the method includes activating a cell or a substrate with light, wherein the cell or the substrate is within one or more wells of a tissue culture plate, wherein the light is generated by a system comprising: a light source operably adjacent to a circuit board and configured to produce light; one or more light guide plates comprising one or more light guides; one or more optical masks positioned on a surface of the one or more wells of the tissue culture plate; a controller; a computer readable medium, comprising instructions that, when executed by the controller, cause the controller to: illuminate the cell or the substrate in the one or more wells with the light from the light source; and spatially and temporally control illumination of the cell or the substrate in the one or more wells with one or more illumination parameters, wherein the one or more light guides is configured to provide uniform illumination of the light in the one or more wells of the tissue culture plate.

Tissue Culture Plate

In some aspects, method includes stimulating and/or activating a cell or a substrate in a tissue culture plate that is positioned adjacent to the illumination device. In some cases, the culture plate is a tissue culture plate (e.g. a cell culture plate or a multi-well plate). In some cases, the illumination device is reversibly connected to a tissue culture plate. By "adjacent", as used heroin in its conventional sense to refer to be in contact with, connected, linked, fastened, or positioned on a surface of the illumination device. In some cases, an illumination device positioned adjacent to a culture plate includes a gap or space between the tissue culture plate and the illumination device.

In some cases, the tissue culture plate includes one or more wells. In some cases, the tissue culture plate includes 24 wells. In some cases, the tissue culture plate includes 96 wells. In some cases, the tissue culture plate includes 384 wells.

In some cases, the tissue culture plate is made from an opaque polymer. In some cases, the tissue culture plate is made from a black polymer. In some cases, the tissue culture plate is made from a material that prevents light from bleeding through between the one or more wells.

In some cases, the tissue culture plate includes a coverglass bottom. In some cases, the one or more wells include a coverglass bottom. In some cases, the coverglass bottom has a thickness ranging from 150-200 µm. In some cases, the coverglass bottom has a thickness of about 150 µm, 160 µm, 170 µm, 180 µm, 190 µm, or 200 µm.

In some cases, the method includes placing the illumination device connected to the tissue culture plate in an incubator. In some cases, the method includes controlling the illumination device connected to the tissue culture plate placed in an incubator. In some cases, controlling the illumination device connected to the tissue culture plate includes controlling the illumination device wirelessly removing the illumination device connected to the tissue culture plate from the incubator.

Cells

In some cases, the tissue culture plate includes one or more wells. In some cases, the method includes placing (e.g. administering a cell via pipette, automated robotic grip, or any other means of administering) a cell in the one or more wells (e.g. one or more cells). In some cases, the method includes aspirating and/or replacing a fluid (e.g. cell culture media, a buffer, or any other solution within the one or more wells) from the one or more wells. In some cases, the cell is a mammalian cell, a bacterial cell, a yeast cell, or a plant cell. Non-limiting examples of mammalian cells include a stem cell, a progenitor cell, a neural cell, or a cardiac cell. In some cases, the cell is a stem cell or a progenitor cell. In some cases, the cell is a bacterial cell. In some cases, the cell is a green algeo. In some cases, the cell is a cyanobacteria. In some cases, the cell is *Spirulina*, or *Synechococcus elongatus*. Non-limiting examples of bacterial cells include *Bacillus subtilis, Escherichia coli, Streptomyces* and *Salmonella typhimuium* cells. In some cases, the cell is a yeast cell. A non-limiting example of a yeast cell is a yeast cell of the species *Saccharomyces cerevisiae*. In some cases, the cell is a plant cell.

In some cases, the method includes spatially and temporally controlling cell signaling and differentiation.

In some cases, the method further includes screening for phototoxicity of the cell in response to light. In some cases, the method further includes screening for a candidate agent to determine whether the candidate agent modulates an activity of the cell (e.g. activation, deactivation, signaling, differentiation).

In some cases, the method includes expressing a protein in the cell. In some cases, the protein is a light activated protein. In some cases, the method includes stimulating the light activated protein. In some cases, the method includes stimulating the light activated protein expressed in the cell.

In some cases, the protein is a fluorescent protein. In some cases, the method further comprises screening for a fluorescent sensor expressed in the cell. In some cases, the fluorescent protein is a yellow fluorescent protein, a red fluorescent protein, a green fluorescent protein, or a cyan fluorescent protein. In some cases, the method further includes screening for the fluorescent protein expressed in the cell in response to light. In some cases, the cell expresses a genetically encoded fluorescent sensor derived from a fluorescent protein. In some cases, the method further includes screening for the genetically encoded fluorescent sensor expressed in the cell.

Light-Activated Proteins

In some cases, the method includes expressing a light-activated protein (e.g. in the cell). In some cases, the method includes stimulating the light activated protein. In some cases, stimulating the light-activated protein activates the light-activated protein in response to light from the light source. In some cases, stimulating the light-activated protein activates the cell expressing the light-activated protein in response to light from the light source. In some cases, the method includes fusing the light activated protein to a c-terminal domain of a lipoprotein receptor-related protein 6 (LRP6).

In some aspects, the light activated protein induces protein interactions. For example, light activated proteins and portions thereof can change conformation upon light absorption, for example, using proteins such as rhodopsins, phytochromes, and cryptochromes, and LOV domains from phototropins and FKFI (Airan et al. (2009) Nature 458: 1025-1029; Inoue et al. (2005) Nat. Methods 2:415-418; Kennedy et al. (2010) Nat. Methods 7:973-975; Levskaya et al. (2009) Nature 461:997-1001; Szobota et al. (2007) Neuron 54:535-545; Wu et al. (2009) Nature 461:104-108; and Yazawa et al. (2009) Nat. Biotechnol. 27:941-945).

In some cases, the light activated protein is selected from a cryptochrome, which is a blue light-sensitive flavoprotein found in plants, animals and microbes; a photoactive yellow protein (PYP) photosensor, which is found in certain bacteria; a photoreceptor of blue-light using flavin adenine dinucleotide (BLUF) and Light, Oxygen, or Voltage sensing (LOV) types, which are plant and bacterial photoreceptors; and a phytochrome, which is used by plants and microbes and are sensitive to light in the red-to-NIR region.

In some cases, the light activated protein is a light-inducible dimerizer. In some cases, the dimerizer is the CRY2/CIB system, based on a light-dependent interaction between *Arabidopsis cryptochrome* 2 (AtCRY2) and an interacting partner, CIB1. In some cases, the dimerizer is the Phy/Pif system. In some cases, the dimerizer is the BphP1/PpsR2 system.

In some cases, the light activated protein is a caged protein domain. In some cases, the caging domain is a LOV domain isolated from the plant photosensor phototropin I (phot1). In some cases, the LOV domain is LOV2. In some cases, the light activated protein is a phytochrome. In some cases, the phytochrome contains a LOV domain, such as phototropin 1, white collar-1 (WC-1), white collar-2 (WC-2), photoactive yellow protein (PYP), Phy3, and VVD. In some cases, the phytochrome is phytochrome B (phyB). PhyB binds to a class of target transcription factors termed phytochrome-interacting factors (Pifs). This light-induced, reversible Phy/Pif dimerization is harnessed to optogenetically stimulate protein-protein interactions in mammalian cells. In some cases, the phytochrome is a bacterial bathyphytochrome BphP1 that interacts with its binding partner PpsR2.

In some cases, the light activated protein is a reactive oxygen species. In some cases, the light activated protein is a genetically encoded ROS-generating protein. In some cases, the light activated protein is a mini singlet oxygen generator (miniSOG), which is a 106 amino acid green fluorescent flavoprotein generated from *Arabidopsis* phototropin 2. In some cases, the light activated protein is KillerRed. KillerRed is a phototoxic fluorescent protein derived from a homolog of GFP, anm2CP.

In some cases, the light activated protein is a photoreceptor UVR8 (UV Resistance Locus 8) has been identified and characterized as a distinct plant photoreceptor that perceives light signals in the UV-B region using intrinsic Trp residues as chromophores In some cases, the light activated protein is CarH, a bacterial transcriptional regulator that controls the biosynthesis of carotenoids in response to light.

In some aspects, stimulating and/or activating the light activated proteins causes membrane depolarization of cell. In some cases, the light activated protein can include depolarizing light-activated proteins. Non-limiting examples of depolarizing light-activated proteins include, e.g., members of the Channelrhodopsin family of light activated protein proteins such as *Chlamydomonas rheinhardtii* channelrhodopsin 2 (ChR2); a step-function opsin (SFO); a stabilized SFO (SSFO); a chimeric opsin such as C1V1; a Volvox carteri-derived channelrhodopsin (VChR1), etc. Such light-responsive polypeptides can be used to promote neural cell membrane depolarization in response to a light stimulus.

In some aspects, the method includes deriving the light activated protein from *Chlamydomonas reinhardtii*, wherein the cation channel protein can be capable of transporting cations across a cell membrane when the cell is illuminated with light.

In some cases, the method includes activating the light activated protein with a wavelength between about 460 and about 495 nm or can have a wavelength of about 480 nm. In some cases, activating the light activated protein includes pulsing the light having a temporal frequency of about 100 Hz to activate the light-responsive protein. In some embodiments, activating the light activated protein by pulsing the light having a temporal frequency of about 100 Hz can cause depolarization of the neurons expressing the light activated protein. The light activated protein can additionally comprise substitutions, deletions, and/or insertions introduced into a native amino acid sequence to increase or decrease sensitivity to light, increase or decrease sensitivity to particular wavelengths of light, and/or increase or decrease the ability of the light activated protein to regulate the polarization state of the plasma membrane of the cell. Additionally, the light activated protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to transport cations across a cell membrane.

In some aspects, stimulating and/or activating the light activated proteins causes membrane hyperpolarization of cell. In some cases, the light-activated protein is a hyperpolarizing light-activated protein. Non-limiting examples of suitable light-responsive polypeptides to be expressed in a cell include, e.g., the Halorhodopsin family of light-responsive chloride pumps (e.g., NpHR, NpHR2.0, NpHR3.0, NpHR3.1). As another example, the GtR3 proton pump can be used to promote cell membrane hyperpolarization in response to light. As another example, eArch (a proton pump) can be used to promote neural cell membrane hyperpolarization in response to light. As another example, an ArchT opsin protein or a Mac opsin protein can be used to promote neural cell membrane hyperpolarization in response to light.

In some cases, the cell in the one or more wells of the tissue culture plate is a stem cell or a progenitor cell. In some cases, method includes expressing a light activated protein in the cell. In some cases, the method includes inducing Wnt/β-catenin signaling in the stem cell in response to light. In some cases, stimulating and/or activating the stem cell expressing the light-activated protein induces Wnt/β-catenin signaling in the stem cell in response to light. In some cases, the method includes fusing the light activated protein to a c-terminal domain of a lipoprotein receptor-related protein 6 (LRP6). In some cases, the method includes inducing differentiation of the stem cell into a mesenchymal stem cell via activation of the Wnt/β-catenin signaling. In some cases, activating and/or stimulating the stem cell, in response to light, expresses a brachyury (Bra) protein.

Substrates

Aspects of the present disclosure include stimulating and/or activating a substrate in one or more wells of the tissue culture plate. In some cases, the method includes polymerizing a substrate in response to light. In some cases, the method includes photopolymerizing the substrate in response to light. In some cases, the stimulating and/or activating the substrate photopolymerizes the substrate in response to light (e.g. light-based activatable signal). In some cases, the method includes spatially and temporally controlling the light as described in the present disclosure, wherein controlling the light provides for spatial and temporal control of photopolymerization of the substrate in response to the light.

In some cases, the method includes photopatterning of the substrate in response to light. In some cases, stimulating and/or activating the substrate provides for photopatterning of the substrate in response to light.

In some cases, the substrate is a polymer. In some cases, polymer is at least one of polylactic acid, poly(lactic-co-glycolic) acid, poly(caprolactone), polyglycolide, polylactide, polyhydroxobutyrate, polyhydroxyalcanoic acid, chitosan, hyaluronic acid (HA), a hydrogels, poly(2-hydroxyethyl-methacrylate), poly(ethylene glycol), poly(L-lactide) (PLA), poly(dimethysiloxane) (PDMS), poly (methylmethacrylate) (PMMA), poly(glycerol sebacate), poly(octamethylene maleate (anhydride) citrate) (POMaC), POMaC without citric acid, poly(.epsilon.-caprolactone), polyurethane, silk, a nanofabricated material, a co-polymer, a blended polymer, or a combination thereof.

In some cases, the polymer includes water-soluble polymer chains. In some cases, the polymer includes water-soluble polymer chains with a cross-linker group. In some cases, the method includes crosslinking polymer chains of the substrate in response to light. In some cases, the polymer chains include one or more methacrylate groups. In some cases, the method includes photopolymerizing the one or more methacrylate groups in response to the light. Methacrylated HA is widely used as scaffolds of extracellular matrix mimicking biomaterials, while the methacrylate groups can self-crosslink in the presence of a photoinitiator, lithium phenyl-2,4,6-trimethylbenzoylphosphinate (LAP). LAP has a broad adsorption band ranging from 350 nm to 410 nm. One molecule of LAP decomposes and dissociates into two radicals following photon adsorption, which further triggers the Michael Addition-type reaction between two methacrylate groups and thus forms crosslinks within the polymer chains. In some cases, the method includes administering (e.g. introducing, placing, applying, pipetting) a photoinitiator on the polymer.

In some cases, the substrate is a polymer. In some cases, the polymer is a hydrogel. In some cases, the substrate is a hydrogel. In some cases, the method includes crosslinking polymers within a hydrogel. In some cases, the substrate is a hydrogel made from hyaluronic acid. In some cases, the hydrogel includes an adhesion motif (protein or protein-derived peptide ligands), an antibody, a growth factors, and/or a gene-encoding nucleic acid, or other bioactive molecules to promote biocompatibility of the hydrogel. In some cases, the method includes introducing one or more of an adhesion motif, an antibody, a growth factors, and/or a gene-encoding nucleic acid, and other bioactive molecules into the hydrogel. In some cases, the hydrogel includes adhesion motifs, such as RGD peptics. In some cases, stimulating and/or activating the hydrogel provides for photopatterning of the hydrogel (e.g. stimulating and/or activating at a wavelength in the ultraviolet spectrum). In some cases, the method includes photopatterning the hydrogel with one or more an adhesion motif, an antibody, a growth factors, and/or a gene-encoding nucleic acid, or other bioactive molecules. In some cases, stimulating and/or activating the hydrogel provides for photopatterning of the hydrogel with one or more an adhesion motif, an antibody, a growth factors, and/or a gene-encoding nucleic acid, or other bioactive molecules.

Other non-limiting examples of hydrogels include hydrogels made from polyvinyl alcohol, sodium polyacrylate, an acrylate polymer, agarose, methylcellulose, or hyaluronan.

In some cases, the polymer includes one or more methacrylate groups. In some cases, the method includes introducing a photoinitiator to the polymer. In some cases, the photoinitiator is lithium phenyl-2,4,6-trimethylbenzoylphosphinate (LAP). In some cases, the method includes photopatterning the polymer in response to light. In some cases, stimulating and/or activating the hydrogel provides for photopatterning of the polymer in response to light. In some cases, the activating provides for crosslinkage of a first methacrylate group and a second methacrylate group within the polymer. In some cases, the method includes crosslinking a first methacrylate group and a second methacrylate group within the polymer. In some cases, the reaction rate between the one or more methacrylate groups is proportional to light intensity. In some cases, the number of crosslinks formed by the one or more methacrylate groups is proportional to light intensity. In some cases, the method includes modulating the stiffness of the polymer in response to light. In some cases, the stiffness of the polymer is proportional to the light intensity and/or the duration of light exposure of the light emitted by the light source.

In some cases, the hydrogel includes one or more cells. In some cases, the method further includes screening for interactions of the one or more cell with an extracellular matrix within the hydrogel.

Light Source

In some cases, the method includes illuminating the one or more wells of the illumination device using a light source. In some cases, the method includes producing or generating uniform light with the light source. In some cases, the method includes positioning the light source adjacent to a circuit board. In some cases, the method includes connecting light source to a circuit board. In some cases, the method includes operably connecting the light source to a circuit board.

In some cases, the light source can be a light emitting diode (LED). In some cases, the light source includes one or more LEDs. In some cases, the LED can generate white, blue, red, and/or green light. In some cases, the LED can generate amber and/or yellow light. In some cases, the LEDs are micro LEDs. In some cases, the LEDs are embedded into a circular array of the circuit board. In some embodiments, the light source is a solid state laser diode or any other means capable of generating light. The light generating means can generate light having an intensity sufficient to activate a cell, protein, and/or a substrate. In some cases, the light includes an irradiance (e.g. light after passing through the optics) having an intensity of any of about 0.005 $\mu W/mm^2$, 0.006 $\mu W/mm^2$, 0.0007 $\mu W/mm^2$, 0.008 $\mu W/mm^2$, 0.009 $\mu W/mm^2$, 0.01 $\mu W/mm^2$, 0.02 $\mu W/mm^2$, 0.03 $\mu W/mm^2$, 0.04 $\mu W/mm^2$, 0.05 $\mu W/mm^2$, 0.1 $\mu W/mm^2$, 0.2 $\mu W/mm^2$, 0.3 $\mu W/mm^2$, 0.4 $\mu W/mm^2$, 0.5 $\mu W/mm^2$, about 0.6 $\mu W/mm^2$, about 0.7 $\mu W/mm^2$, about 0.8 $\mu W/mm^2$, about 0.9 $\mu W/mm^2$, about 1.0 $\mu W/mm^2$, about 1.1 $\mu W/mm^2$, about 1.2 $\mu W/mm^2$, about 1.3 $\mu W/mm^2$, about 1.4 $\mu W/mm^2$, about 1.5 $\mu W/mm^2$, about 1.6 $\mu W/mm^2$, about 1.7 $\mu W/mm^2$, about 1.8 $\mu W/mm^2$, about 1.9 $\mu W/mm^2$, about 2.0 $\mu W/mm^2$, about 2.1 $\mu W/mm^2$, about 2.2 $\mu W/mm^2$, about 2.3 $\mu W/mm^2$, about 2.4 $\mu W/mm^2$, about 2.5 $\mu W/mm^2$, about 3 $\mu W/mm^2$, about 3.5 $\mu W/mm^2$, about 4 $\mu W/mm^2$, about 4.5 $\mu W/mm^2$, about 5 $\mu W/mm^2$, about 5.5 $\mu W/mm^2$, about 6 $\mu W/mm^2$, about 7 $\mu W/mm^2$, about 8 $\mu W/mm^2$, about 9 $\mu W/mm^2$, about 10 $\mu W/mm^2$, about 11 $\mu W/mm^2$, about 12 $\mu W/mm^2$, about 13 $\mu W/mm^2$, about 14 $\mu W/mm^2$, about 15 $\mu W/mm^2$, about 16 $\mu W/mm^2$, about 17 $\mu W/mm^2$, about 18 $\mu W/mm^2$, about 19 $\mu W/mm^2$, about 20 $\mu W/mm^2$, about 21 $\mu W/mm^2$, about 22 $\mu W/mm^2$, about 23 $\mu W/mm^2$, about 24 $\mu W/mm^2$, or about 25 $\mu W/mm^2$, inclusive, including values in between these numbers. In some cases, the light includes an irradiance having an intensity ranging from about 0.0001 to about 25 $\mu W/mm^2$, about 25 to 50 $\mu W/mm^2$, about 50-100 $\mu W/mm^2$, about 100-150 $\mu W/mm^2$, or 150-200 $\mu W/mm^2$. In other embodiments, the light-generating means produces light having a frequency of at least about 100 Hz. In some cases, the light source produces light having an intensity of any of about 0.05 $mW/mm^2$, 0.1 $mW/mm^2$, 0.2 $mW/mm^2$, 0.3 $mW/mm^2$, 0.4 $mW/mm^2$, 0.5 $mW/mm^2$, about 0.6 $mW/mm^2$, about 0.7 $mW/mm^2$, about 0.8 $mW/mm^2$, about 0.9 $mW/mm^2$, about 1.0 $mW/mm^2$, about 1.1 $mW/mm^2$, about 1.2 $mW/mm^2$, about 1.3 $mW/mm^2$, about 1.4 $mW/mm^2$, about 1.5 $mW/mm^2$, about 1.6 $mW/mm^2$, about 1.7 $mW/mm^2$, about 1.8 $mW/mm^2$, about 1.9 $mW/mm^2$, about 2.0 $mW/mm^2$, about 2.1 $mW/mm^2$, about 2.2 $mW/mm^2$, about 2.3 $mW/mm^2$, about 2.4 $mW/mm^2$, about 2.5 $mW/mm^2$, about 3 $mW/mm^2$, about 3.5 $mW/mm^2$, about 4 $mW/mm^2$, about 4.5 $mW/mm^2$, about 5 $mW/mm^2$, about 5.5 $mW/mm^2$, about 6 $mW/mm^2$, about 7 $mW/mm^2$, about 8 $mW/mm^2$, about 9 $mW/mm^2$, about 10 $mW/mm^2$, about 11 mW/mm$^2$, about 12 mW/mm$^2$, about 13 mW/mm$^2$, about 14 mW/mm$^2$, about 15 mW/mm$^2$, about 16 mW/mm$^2$, about 17 mW/mm$^2$, about 18 mW/mm$^2$, about 19 mW/mm$^2$, about 20 mW/mm$^2$, about 21 mW/mm$^2$, about 22 mW/mm$^2$, about 23 mW/mm$^2$, about 24 mW/mm$^2$, or about 25 mW/mm$^2$, inclusive, including values in between these numbers.

In some aspects, the method includes externally activating the light source by a controller. In some cases, the controller includes a processor. In some cases, the method includes supplying power to the controller via a power source. In some cases, the method includes mounting a power source to a transmitting coil. In some cases, the method includes, the method includes connecting a battery to the power source, for providing power thereto (e.g. to the controller). In some cases, the method includes connecting a switch to the power source, allowing an individual to manually activate or deactivate the power source.

In some cases, the method includes independently illuminating each of the one or more wells of the tissue culture plate. In some cases, the method includes illuminating each of the one or more wells of the tissue culture plate by the one or more LEDs.

Circuit Board

In some aspects, the illumination device includes one or more circuit boards. In some cases, the method includes positioning a light source adjacent to the circuit board. In some cases, the method includes connecting a light source to the circuit board. In some cases, the light source includes one or more LEDs. In some cases, the method includes generating a printed circuit board (PCB). In some cases, the illumination device includes one or more circuit boards. In some cases, the circuit board includes one or more circular arrays. In some cases, the illumination device includes a first circuit board (PCB1). In some cases, the PCB1 includes electronics for LED control. In some cases, the illumination device further comprises a power distribution board. In some cases, the illumination device includes a second circuit board (PCB2). In some cases, the PCB2 is a power distribution board. In some cases, the PCB1 contains solder pads for a circular array of 5 LEDs in order to emit light from the 5 LEDs to one well of the tissue culture plate (e.g. a 24 well tissue culture plate). In some cases, the 5 LEDs are connected to the circular array of the circuit board in series.

In some cases, the one or more LEDs are symmetrically and radially distributed on one or more circular arrays on the circuit board. In some cases, each of the one or more circular arrays has a radius ranging from about 2-10 mm (e.g. 2 mm, 3 mm, 4 mm, 5 mm, 6 mm, 7 mm, 8 mm, 9 mm, or 10 mm). In some cases, each of the one or more circular arrays has a radius of about 5 mm.

In some cases, the method includes distributing 5 LEDs symmetrically and radially on each of the one or more circular arrays of the circuit board. In some cases, the circuit board includes 24 circular arrays. In some cases, the method includes positioning one or more circular arrays below the one or more wells of the tissue culture plate. In some cases, the method includes illuminating one well of the one or more wells in the tissue culture plate with 5 LEDs on the circular array.

In some cases, the method includes distributing 1 LED symmetrically and radially on each of the one or more circular arrays of the circuit board. In some cases, the circuit board includes 96 circular arrays. In some cases, the method includes positioning 1 LED at approximately the center of each circular array.

In some cases, the method includes positioning one or more LEDs on the circuit board below the one or more wells of the tissue culture plate.

In some aspects, the method includes reducing heat and/or moving heat away from the illumination device and/or tissue culture plate through a heat sink mounted on the circuit board.

In some cases, the method includes mounting a heat sink on the circuit board with a thermally conductive adhesive. In some cases, the method includes mounting a heat sink onto the bottom surface of the first circuit board (e.g. PCB1). In some cases, the method includes mounting a heat sink using a thermally conductive adhesive. In some cases, the thermally conductive adhesive is Artic Silver, ASTA-7G. In some cases, the method includes mounting the heat sink onto the circuit board (e.g. first circuit board) in a region without silk screen and thermally conductive electrical vias that draw heat away from the one or more LEDs.

In some cases, the method includes cooling the illumination device and/or tissue culture plate. In some cases, the method includes cooling the illumination device and/or tissue culture plate with one or more cooling fans. In some cases, the illumination device includes two cooling fans. In some cases, the illumination device includes three cooling fans. In some cases, the method includes positioning one or more cooling fans on the outer edges of the circuit board. In some cases, the method includes electrically connecting the first circuit board to the one or more cooling fans.

In some aspects, the method includes connecting the illumination device to a power supply. In some cases, the method includes operably connecting the illumination device to the power supply. In some cases, the method includes electrically connecting the illumination device to the power supply. In some cases, the method includes connecting the power supply to the second circuit board (e.g. PCB2) of the illumination device. In some cases, method includes supplying power to the one or more cooling fans and the controller through switching voltage regulators.

Contoller

In some aspects, the method includes controlling the illumination device with a controller. In some cases, controlling the illumination device with a controller provides for independently illuminating each of the one or more wells of the tissue culture plate.

In some cases, the controller is a microcontroller. In some cases, the controller is a Raspberry Pi microcontroller. In some cases, the method includes mounting a tissue culture plate in a position on the illumination device such that the method provides for illuminating the tissue culture plate from the bottom.

In some cases, the method includes controlling the illumination device with a controller, wherein the controller includes an LED driver. In some cases, the method includes controlling the illumination device with an LED driver. In some cases, the LED driver includes one or more channels. In some cases, the LED driver is a 24-channel LED driver. In some cases, the LED driver is a 96-channel LED driver. In some cases, the LED driver is a 384-channel LED driver. In some cases, the method includes controlling two or more, three or more, four or more, five or more, six or more, seven or more, eight or more, nine or more, or ten or more LED drivers. In some cases, the illumination device includes four LED drivers. In some cases, the method includes controlling, independently, of each of the channels of the LED driver (e.g. a 24-channel LED driver, a 96 channel LED driver, or a 384-channel LED driver). In some cases, the method includes independently illuminating each of the one or more wells of the tissue culture plate with the controller.

In some cases, the method includes connecting the illumination device to a power supply. In some cases, the method includes connecting the power supply to the LED driver of the illumination device. In some cases, the method includes connecting the power supply to the second circuit board through a barrel power jack to power the one or more LEDs through the LED driver. In some cases, the method includes powering the second circuit board to power the one or more LEDs through the LED driver.

In some cases, the method includes electrically connecting the LED driver to the circuit board. In some cases, the method includes mounting the LED driver and electrically connecting the LED driver to the first circuit board of the illumination device. In some cases, the method includes mounting the microcontroller and electrically connecting the microcontroller to the first circuit board. In some cases, the method includes mounting the second circuit board (e.g. PCB2) and electrically connecting the first circuit board to the first circuit board (PCB1).

In some cases, the method includes controlling the one or more wells of the tissue culture plate with one or more channels of the LED driver. In some cases, the LED driver is a 24-channel LED driver. In some cases, the method includes controlling one or more LEDs with the LED driver. In a non-limiting example, for 24-well illumination (e.g. illumination of 24 wells in a 24 tissue culture plate), a first circuit board includes 24 circular arrays containing 5 LEDs radially and symmetrically distributed on each of the 24 circular arrays. In some cases, the method includes independently controlling illumination of each well in the 24 tissue culture plate with the 24-channel LED driver, wherein each channel of the LED driver controls one well in the 24 well plate. Another non-limiting example includes 96-well illumination (e.g. illumination of 96 wells in a 96 tissue culture plate), a first circuit board includes 96 circular arrays containing 1 LED radially and symmetrically distributed on each of the 96 circular arrays. In some cases, the method includes illuminating 24 independent channels, wherein each channel controls 4 wells of the 96 well plate. In some cases, the illumination device includes four LED drivers, each containing 24 channels. In such cases, the four LED drivers, combined, include 96 independent channels, wherein each channel controls one well of the 96 wells in the tissue culture plate. In some cases, the four LED drivers are chained together to provide independent control of each well in the 96 wells of the tissue culture plate.

In some cases, the method includes reducing static or electrical shorting of the illumination device. In some cases, the method includes mounting the illumination device connected to the tissue culture plate onto a material through vibration-dampening mounts. A non-limiting example of the material may include an acrylic, plastic, metal, or composite material or any material that is secure enough to constitute a base. In some cases, the acrylic material is an acrylic lascar-cut base. In some cases, the vibration-dampening mounts include rubber footpegs. In some cases, the vibration-dampening mounts are configured to reduce static or electrical shorting with the tissue culture incubation racks.

Light Guide Plates

Aspects of the present disclosure include contacting light from the light source with one or more one or more light guide plates to illuminate the cell or the substrate in the one or more wells. In some cases, the light guide plates include one or more light guides. In some cases, contacting light with one or more light guides produces an arc-shaped light beam from the light source emitted by the light source. In some cases, the light beam from the light source includes 100 or more μm, 200 or more μm, 300 or more μm, 400 or more μm, 500 or more μm, or 600 or more μm arc of light. In some cases, the light beam from includes 500 μm arc of light.

In some cases, the one or more light guide plates comprises a first light guide plate and a second light guide plate. In some cases, the first light guide and the second light guide can include light guides that are the same form of each other (e.g. made from the same material, and/or have the same dimensions, etc.). In some cases, the first light guide and the second light guide can include light guides that are different forms of each other (e.g. made from different materials, and/or have different dimensions, etc.)

In some cases, the one or more light guide plates include one or more light guides. In some cases, the one or more light guides comprises 24 light guides, % light guides, or 384 light guides. In some cases, the illumination device has one or more light guides within each of the one or more light guide plates. For example, in some cases, the light guides within each of the one or more light guide plates are held in an array by a surrounding frame of the light guide plate. In some cases, the illumination device has 24 light guides held in an array by a surrounding frame of the light guide plate. In some cases, the illumination device has 96 light guides held in an array by a surrounding frame of the light guide plate. In some cases, the illumination device has 384 light guides held in an array by a surrounding frame of the light guide plate.

In some cases, the one or more light guides has a diameter of about 5 or more mm, about 6 or more mm, about 7 or more mm, about 8 or more mm, about 9 or more mm, about 10 or more mm, about 11 or more mm, about 12 or more mm, about 13 mm or more, about 15 mm or more, about 16 mm or more, about 17 mm or more about 18 mm or more, about 19 mm or more, or about 20 mm or more. In some cases, the one or more light guides has a diameter of about 7 or more mm. In some cases, the one or more light guides has a diameter of about 16.5 or more mm. In some cases, the one or more light guides has a radius of about 8.25 mm. In some cases, the one or more light guides has a diameter of about 16.5 mm. In some cases, the one or more light guides has a thickness ranging from 0.5 cm to about 5 cm. In some cases, the one or more light guides has a thickness of about 0.5 cm, about 1 cm, about 1.5 cm, about 2 cm, about 2.5 cm, about 3 cm, about 3.5 cm, about 4 cm, about 4.5 cm, or about 5 cm. In some cases, the one or more light guides has a thickness ranging from 1 cm to 1.5 cm. In some cases, the one or more light guides has a thickness of about 1.5 cm.

In some cases, the one or more light guides can be of a circular shape and/or other shapes as required per conditions specific to its intended use. In some cases, the one or more light guides comprises a circular shape. In some cases, the one or more light guides comprises a cylindrical shape, a circular shape, a square shape, a spherical shape, a cone-shape, a prism-shape, or a rectangular shape. In some cases, each of the light guides is the same shape. In some cases, each of the light guides is a different shape. The light guides are not limited to the shapes and/or sizes as described herein and can be any shape and/or size as required per conditions specified to its intended use.

In some cases, the one or more light guide plates and/or light guides is transparent and made from a material selected from glass, acryl, plastic, polymethylmethacrylate (PMMA), poly-lactic acid (PLA), and epoxy. In some cases, the one or more light guide plates and/or light guides is opaque except for the region of the light guide through which light passes through (e.g. the center of the light guide). In some cases, the one or more light guide plates and/or light guides is transparent in the center of the light guide through which light passes through.

In some cases, the one or more light guide plates is made from a polymer. In some cases, the polymer is acrylic or PLA. In some cases, the one or more light guides includes a reflective coating.

In some cases, the one or more light guides is configured to directly receive only light that is generated from the one or more LEDs positioned in the one or more circular arrays of the circuit board. In some cases, each of one or more light guides is positioned to provide for selective illumination for each of the one or more wells of the tissue culture plate.

In some cases, the method includes positioning a first light guide plate adjacent (e.g. connected to) to the circuit board (e.g. the first circuit board or the second circuit board).

In some cases, the illumination uniformity of the light beam from light emitted by the light source is proportional to the thickness of the one or more light guides. In some cases, increasing the thickness of the light guide decreases the difference between the edge and center intensities of the one or more wells. In some cases, increasing the thickness of the light guide from 1 cm to 1.5 cm decreases difference between the edge and center intensities of the one or more wells. In some cases, the one or more light guides improves the illumination uniformity by about 10% or more, 20% or more, 30% or more, 40% or more, 50% or more, 60% or more, or 70% or more as compared to an illumination device without a light guide.

In some cases, the light guide is configured to decrease the variability of light intensity of the light beam emitted from the light source between each of the one or more wells of the tissue culture plate.

Optical Diffusers

In some aspects, the illumination device includes one or more optical diffusers. In some cases, the one or more optical diffusers comprises a first optical diffuser and a second optical diffuser. In some cases, the first light guide plate is positioned between the first and second optical diffuser. However, optical elements beside diffusers can also be used to collimate the light to make the light beam more uniform. A non-limiting example of an optical element other than a diffuser includes Fresnel lenses, which is a lens that takes the shape of a flat sheet and can be used instead of a diffuser to collimate the light.

In some cases, the one or more optical diffusers comprises one or more 80° circular optical diffusers. Optical diffusers can be any material that diffuses or scatters light. In some cases, the one or more optical diffusers and light guides control the uniformity and intensity of the signals being projected onto the cell or substrate. In some cases, the one or more diffusers include one or more 80° diffuser coatings. (e.g. scatter coating, full width-half max). In some cases, the diffuser coating is coated on a polycarbonate material. In some cases, the polycarbonate has a thickness of about 0.1 inches. However, the one or more diffusers are not limited to 80° diffuser coatings and can be any known diffuser coating applied to different substrates.

In some cases, the first optical diffuser is positioned between the tissue culture plate and the first light guide plate. In some cases, the second optical diffuser is positioned between the first light guide plate and the second light guide plate. In some cases, the first optical diffuser is positioned between the tissue culture plate and the first light guide plate. In some cases, the second optical diffuser is positioned between the first light guide plate and the second light guide plate. In some cases, the first optical diffuser and the second optical diffuser can include optical diffusers that are the same form of each other (e.g. made from the same material, and/or have the same dimensions, etc.). In some cases, the first optical diffuser and the second optical diffuser can include optical diffusers that are different forms of each other (e.g. made from different materials, and/or have different dimensions, etc.)

Optical Masks

In some cases, the method includes selectively blocking a wavelength of light outside of a surface (e.g. core region, aperture, cut-out feature, slit, etc.) of one or more optical masks. In some cases, the method includes selectively blocking a wavelength of light outside of a core region of one or more optical masks. In some cases, the illumination device includes one or more optical masks. In some cases, the one or more optical masks are configured to selectively block a wavelength of light outside of a core region of the one or more optical masks from reaching a detector to detect the light. In some cases, the one or more optical masks is configured to block a wavelength of light from reaching the illuminated sample or substrate.

In some cases, the one or more optical masks includes an aperture. In some cases, the method includes cutting (e.g. removing, extracting, laser cutting, die-cutting, etching, puncturing, etc.) a portion of an optical mask to obtain a core region. In some cases, the one or more optical masks includes one or more cut-out features. In some cases, the one or more cut-out features includes a patterned cut-out feature.

In some cases, the one or more patterned cut-out features includes a core region. In some cases, the core region includes a pattern size ranging from 10-600 μm. In some cases, the core region includes a pattern size ranging from 50-500 μm. In some cases, the core region includes a pattern size of about 50 or more μm, 100 or more μm, 150 or more μm, 200 or more μm, 250 or more μm, 300 or more μm, 350 or more μm, 400 or more μm, 450 or more μm, 500 or more μm, 550 or more μm, or 600 or more μm.

In some cases, the one or more patterned cut-out features is a slit. In some cases, the one or more patterned cut-out features is a curved slit (e.g., an arc). In some cases, the one or more patterned cut-out features is a circle, rectangle, square, or triangle. In some cases, the patterned cut-out feature can be of a slit shape and/or other shapes as required per conditions specific to its intended use.

In some cases, the method includes selectively blocking the passage of light outside of the core region of the optical mask.

In some cases, the one or more optical masks are made of an opaque material. In some cases, the core region of the one or more optical mask does not include the opaque material from which the optical mask is made from (e.g. the core region includes an aperture or a patterned slit in the material). In some cases, the one or more optical masks include a combination of a transparent material and an opaque material. In some cases, the combination of a transparent material and an opaque material provides for greyscale modulation of the light pattern. In some cases, the core region of the optical mask includes a transparent material, and the material outside of the core region is an opaque material.

In some cases, the method includes adhering the one or more optical masks to the one or more wells of the tissue culture plate. In some cases, the method includes positioning the one or more optical masks on a surface of one or more wells of the tissue culture plate. In some cases, the method includes positioning the one or more optical masks on a surface of the one or more wells. In some cases, the method includes positioning the one or more optical masks on a bottom outer surface of the one or more wells. In some cases, the method includes positioning a core region of the one or more optical masks in the center of an outer surface of the one or more wells. In some cases, the method includes positioning the one or more optical masks on the one or more wells of the tissue culture plate. In some cases, the method includes positioning the one or more optical masks on an outer surface of the coverglass bottom. In some cases, the method includes positioning the one or more optical masks at a distal end (e.g. the closed-ended outer surface of the one or more wells) of the one or more wells of the tissue culture plate relative to an open ended surface of the one or more wells. In some cases, the method includes positioning the one or more optical masks on a surface of one or more wells of the tissue culture plate.

In some cases, the method includes positioning the one or more optical masks includes on each of the one or more wells of the tissue culture plate. In some cases, the one or more optical masks comprises 24 optical masks, each mask positioned on each of the 24 wells of the tissue culture plate. In some cases, the one or more optical masks includes an optical mask positioned on each of the one or more wells of the tissue culture plate. In some cases, the one or more optical masks comprises 96 optical masks, each mask positioned on each of the 96 wells of the tissue culture plate. In some cases, the one or more optical masks includes an optical mask positioned on each of the one or more wells of the tissue culture plate. In some cases, the one or more optical masks comprises 384 optical masks, each mask positioned on each of the 384 wells of the tissue culture plate.

In some cases, the optical mask includes a photo mask or an intensity mask. A "photo mask", as used herein in its conventional sense, refers to a material, coating, and/or plate with holes or transparencies that allow light to pass through in a defined pattern. In some cases, the photo mask absorbs light to varying degrees and can be patterned as required per conditions specific to its intended use. In some cases, the photo mask is an intensity mask. In some cases, the intensity mask is fully absorbing (e.g. opaque, dark), or not absorbing (e.g. transparent, bright), or a combination thereof. In some cases, the intensity mask is made from adhesive vinyl. In some cases, the adhesive vinyl is polyvinyl chloride (PVC). In some cases, the intensity mask is made from Biaxially Oriented Polypropylene.

In some cases, the optical mask is a phase mask. In some cases, the phase mask is a phase shift mask. A phase mask is used to modulate the phase of light in order to change the light intensity. The phase modulation results in constructive and destructive interference that generates a pattern of light intensity, which can be similar to a light pattern generated with an intensity mask. It can be used in combination with an intensity mask, which is then called a phase-shift mask. In some cases, the phase mask is made from glass (e.g. quartz).

In some cases, the illumination pattern when the light beam contacts the one or more wells includes a 0.5 mm diameter of light, 1.0 mm diameter of light, 1.5 mm diameter of light, or a 2 mm diameter of light emitted to the one or more wells. In some cases, the illumination pattern includes a 1.5 mm diameter of light emitted to the one or more wells.

In some cases, the one or more wells includes one or more cells. In some cases, the cell migrates a distance beyond the boundary of the core region. In some cases, the distance is 50 μm or more beyond the boundary of the core region. In some cases, the distance is 500 μm beyond the boundary of the core region.

Detector

In some aspects, the method includes detecting light emitted from the cell or substrate with one or more detectors. In some aspects, the illumination device can be used in combination with a microscope, a spectrophotometer, a detector, or a robotic handler. Non-limiting examples of microscopes include a fluorescence microscope. a confocal laser scanning microscope, and/or a bright-field microscope), a spectrophotometer, or a detector. In some cases, the detector is a photomultiplier tube, a charged coupled device (CCD), or a complementary metal oxide semiconductor (CMOS) sensor. In some cases, the detectors of interest are configured to measure collected light at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths. In some embodiments, the method includes measuring collected light over a range of wavelengths (e.g., 200 nm to 1000 nm). In some embodiments, measuring includes measuring absorbance, reflectance, emission intensity, and/or fluorescence of the light signals. In some embodiments, detectors are configured to collect spectra of light over a range of wavelengths. In some embodiments, an optical imaging system may include one or more detectors configured to collect spectra of light over one or more of the wavelength ranges of 200 nm to 1000 nm. In some embodiments, detectors of are configured to measure light emitted by a cell or substrate in the one or more wells of a tissue culture plate at one or more specific wavelengths. For example, the one or more detectors are configured to measure light at one or more of 350 nm, 370 nm, 400 nm, 410 nm, 450 nm, 518 nm, 519 nm, 561 nm, 578 nm, 605 nm, 607 un, 625 nm, 650 nm, 660 nm, 667 nm, 670 nm, 668 nm, 695 nm, 710 nm, 723 nm, 780 nm. 785 nm, 647 nm, 617 nm and any combinations thereof. In some embodiments, one or more detectors may be configured to be paired with specific fluorophores, such as those used in a fluorescence assay.

In some cases, the method includes positioning the one or more detectors about 5 or more mm away from the light source. In some cases, the method includes positioning the one or more detectors about 10 mm or more, 15 mm or more, 20 mm or more, or 25 mm or more away from the light source. In some cases, the method includes positioning the one or more detectors is about 21 mm away from the light source.

Graphical User Interface (GUI)

In some cases, the method includes controlling the illumination device with a graphical user interface (GUI) to communicate wirelessly with the controller of the illumination device. In some cases, the method includes programming, with the GUI, the illumination parameters of the one or more wells. In some cases, the GUI can be used to wirelessly program the illumination intensity and temporal (e.g. time) sequences of each of the one or more wells. In some cases, the GUI provides for a user to input a desired illumination parameter for each of the one or more wells. In some cases, the method includes wirelessly uploading the illumination parameters to the controller (e.g. the microcontroller and/or the LED driver) on the illumination device through the GUI.

In some cases, the method includes modulating the illumination parameters of the illumination device through the GUI. In some cases, the method includes setting each channel of the LED driver (e.g. in a 24 channel LED driver or a 96-channel LED driver) with one or more illumination parameters through the GUI. In some cases, the GUI allows the user to set each channel to, for example, constant illumination at a specified intensity; blinking illumination at a specified intensity, duty cycle, and time period; and a series of linear or sinusoidal functions at specified illumination parameters.

In some cases, the GUI provides for multiple piecewise functions that can be programmed in a time sequence.

Illumination Parameters

In some cases, the method includes spatially and temporally controlling light from the illumination device to spatially and temporally control illumination of a cell or a substrate with one or more illumination patterns. The term "spatial control" as used herein, refers to controlling (e.g. modulating or varying) a spatial distribution of light waves in space (e.g. controlling the intensity, amplitude, frequency, and/or phase of the light waves emitted to a targeted area; controlling the distance of the light beam; controlling the distribution of the light beam). The term "temporal control" as used herein, refers to controlling (e.g. modulating or varying) a distribution (e.g. intensity, amplitude, frequency, and/or phase) of light waves over time.

In some cases, the illumination parameters can include, but are not limited to, frequency of light emitted from the light source, duty cycle, duration of light emitted from the light source, and specific patterns of illumination (e.g. pulsed illumination). In some cases, the one or more illumination parameters is selected from an illumination intensity, an illumination duration, an illumination pattern, and a combination thereof.

In some cases, the illumination parameter is an amplitude of light. In some cases, the illumination parameter is a light frequency. In some cases, the illumination parameter is a phase of light.

In some cases, the illumination intensity ranges from about 0.005 µW/mm$^2$ to about 20 µW/mm$^2$. In some cases, the illumination intensity ranges from about 0.005 µW/mm$^2$ to about 10 µW/mm$^2$. In some cases, the illumination intensity ranges from about 0.005 µW/mm$^2$ to about 20 mW/mm$^2$.

In some cases, the method includes illuminating the cell or the substrate of the one or more wells of the tissue culture plate with an illumination pattern. In some cases, the illumination pattern is a pulsing pattern, where light is pulsed in a millisecond time frame. In some cases, an illumination duration ranges from about 0.5 or more ms, 1 or more ms, 2 or more ms, 3 or more ms, 4 or more ms, 5 or more ms, 6 or more ms, 7 or more ms, 8 or more ms, or 10 or more ms. In some cases, the pulsed illumination includes a pulse duration of 1 or more ms.

In some cases, the method includes illuminating the cell or the substrate with a pulsed illumination. In some cases, the illumination pattern is a pulsing pattern, where light is pulsed in a millisecond time frame. In some cases, the illumination device further includes a pulse generator configured to pulse the light emitted from the light source.

In some cases, the illumination pattern includes a sinusoidal or linear pattern with a pulsing frequency of 1 or more Hz.

In some cases, the illumination pattern includes a blinking pattern with a pulsing frequency of about 1 or more Hz, 10 or more Hz, 20 or more Hz, 30 or more Hz, 40 or more Hz, 50 or more Hz, 60 or more Hz, 70 or more Hz, 80 or more Hz, 90 or more Hz, 100 or more Hz, 100 or more Hz, 110 or more Hz, 120 or more Hz, 130 or more Hz, 140 or more Hz, or 150 or more Hz. In some cases, the illumination pattern includes a blinking pattern with a pulsing frequency of about 100 Hz.

In some cases, the illumination pattern includes a 0.5 mm diameter of light, 1.0 mm diameter of light, 1.5 mm diameter of light, or a 2 mm diameter of light emitted to the one or more wells. In some cases, the illumination pattern includes a 1.5 mm diameter of light emitted to the one or more wells.

In some cases, the illumination duration includes illumination of the one or more wells for 1 or more hours. In some cases, the illumination duration includes illumination of the one or more wells for 1 or more weeks. In some cases, the illumination duration ranges from about 0.5 or more ms, 1 or more ms, 2 or more ms, 3 or more ms, 4 or more ms, 5 or more ms, 6 or more ms, 7 or more ms, 8 or more ms, or 10 or more ms. In some cases, the illumination duration ranges from about 0.5 or more s, 1 or more s, 2 or more s, 3 or more s, 4 or more s, 5 or more s, 6 or more s, 7 or more s, 8 or more s, or 10 or more s. In some cases, the illumination duration ranges from about 1 or more minutes, 2 or more minutes, 3 or more minutes, 4 or more minutes, 5 or more minutes, 6 or more minutes, 7 or more minutes, 8 or more minutes, or 10 or more minutes.

In some cases, the one or more wells can be illuminated with red, amber, yellow, green, blue, or white light. In some cases, the GUI can set the color of light corresponding to a specific wavelength.

In some cases, the method includes modulating the wavelength through the GUI to allow the user to set a wavelength of light for which light can be emitted. In some cases, the method includes illuminating, stimulating, and/or activating the cell or the substrate with a light having a wavelength ranging from 200 to 1000 nm. In some cases, the light can have a wavelength ranging from about 350 to about 410 nm. In some cases, the light can have a wavelength of about 470 nm and about 510 nm or can have a wavelength of about 490 nm. In some cases, the light can have a wavelength of about 470 nm. In some cases, the light can have a wavelength of about 445 nm. In some cases, the light can have a wavelength ranging from about 530 to about 595 nm. In some cases, the light can have a wavelength of about 530 nm. In some cases, the light can have a wavelength of about 560 nm. In some cases, the light can have a wavelength of about 542 nm. In some cases, the light can have a wavelength of about 546 nm. In some cases, the light can have a wavelength ranging from about 580 and 630 nm. In some cases, the light can be at a wavelength of about 589 nm or the light can have a wavelength greater than about 630 nm (e.g. less than about 740 nm). In another embodiment, the light has a wavelength of around 630 nm.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-30 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A system for spatially and temporally controlling light, the system comprising:
a tissue culture plate comprising one or more wells, wherein the one or more wells comprises a cell or a substrate; an illumination device positioned adjacent to the tissue culture plate, wherein the illumination device comprises: a light source operably connected to a circuit board and configured to produce light; one or more light guide plates comprising one or more light guides; one or more optical masks positioned adjacent to the one or more wells of the tissue culture plate; a controller; a computer readable medium, comprising instructions that, when executed by the controller, cause the controller to: illuminate the cell or the substrate in the one or more wells with light from the light source; and spatially and temporally control illumination of the cell or the substrate with one or more illumination parameters, wherein the one or more light guides is configured to provide uniform illumination of the light in the one or more wells of the tissue culture plate.

2. The system of Aspect 1, wherein the cell is a stem cell or a progenitor cell.

3. The system of Aspect 1, wherein the system further comprises a microscope, a spectrophotometer, or a detector.

4. The system of Aspect 1, wherein the one or more optical masks is a photo mask, intensity mask, or a phase mask.

5. The system of Aspect 1, wherein the one or more optical masks is positioned on a bottom surface of the one or more wells of the tissue culture plate.

6. The system of Aspect 1, wherein the illumination device further comprises one or more optical diffusers.

7. The system of Aspect 1, wherein the one or more illumination parameters is selected from an illumination intensity, an illumination duration, and an illumination pattern, and a combination thereof.

8. The system of Aspect 1, wherein the system further comprises a graphical user interface (GUI) configured to communicate wirelessly with the controller.

9. The system of Aspect 1, wherein the one or more optical masks comprises one or more patterned cut-out features comprising a core region.

10. The system of Aspect 9, wherein the core region comprises a pattern size ranging from 50-600 μm.

11. The system of Aspect 9, wherein the one or more optical masks is configured to selectively block the passage of light outside of the core region.

12. The system of Aspect 9, wherein the core region of the one or more optical masks is positioned in the center of an outer surface of the one or more wells.

13. The system of Aspect 1, wherein the light source comprises one or more light-emitting diodes (LEDs).

14. The system of Aspect 13, wherein the one or more wells is independently illuminated by the one or more LEDs.

15. The system of Aspect 13, wherein the one or more LEDs is symmetrically and radially distributed on one or more circular arrays on the circuit board.

16. The system of Aspect 15, wherein the circuit board comprises 5 LEDs symmetrically and radially distributed on each of the one or more circular arrays of the circuit board.

17. The system of Aspect 15, wherein each of the one or more circular arrays has a radius of about 5 mm.

18. The system of Aspect 15, wherein the one or more light guides is configured to directly receive only light that is generated from the one or more LEDs positioned in the one or more circular arrays of the circuit board.

19. The system of Aspect 1, wherein the illumination uniformity of the light beam from light emitted by the light source is proportional to the thickness of the one or more light guides.

20. The system of Aspect 1, wherein the light guide is configured to decrease the variability of light intensity of the light beam emitted from the light source between each of the one or more wells of the tissue culture plate.

21. An illumination device for spatially and temporally controlling light, the device comprising: an illumination device connected to a tissue culture plate comprising a cell or a substrate in one or more wells of the tissue culture plate, wherein the illumination device comprises: a light source operably adjacent to a circuit board and configured to produce light; one or more light guide plates comprising one or more light guides; one or more optical masks positioned on a surface of the one or more wells of the tissue culture plate; a controller; a computer readable medium, comprising instructions that, when executed by the controller, cause the controller to: illuminate the cell or the substrate with light from the light source; and spatially and temporally control illumination of light to the cell or the substrate in the one or more wells with one or more illumination parameters, wherein the one or more light guides is configured to provide uniform illumination of the light in the one or more wells of the tissue culture plate.

22. The device of Aspect 21, wherein the one or more light guides has a thickness ranging from 0.5 cm to 5 cm.

23. The device of Aspect 21, further comprising one or more optical diffusers.

24. The device of Aspect 21, further comprising a heat sink mounted on the circuit board.

25. The device of Aspect 21, further comprising a cooling fan.

26. The device of Aspect 21, wherein the one or more illumination parameters is selected from an illumination intensity, an illumination duration, an illumination pattern, and a combination thereof.

27. The device of Aspect 21, wherein the illumination uniformity of the light beam from light emitted by the light source is proportional to the thickness of the one or more light guides.

28. The device of Aspect 21, wherein the light guide is configured to decrease the variability of light intensity of the light beam emitted from the light source between each of the one or more wells of the tissue culture plate.

29. A method for selectively spatially and temporally controlling light, the method comprising: activating a cell or a substrate with light, wherein the cell or the substrate is within one or more wells of a tissue culture plate, wherein the light is generated by a system comprising: a light source operably connected to a circuit board and configured to produce light; one or more light guide plates comprising one or more light guides; one or more optical masks positioned on a surface of the one or more wells of the tissue culture plate; a controller, a computer readable medium, comprising instructions that, when executed by the controller, cause the controller to: illuminate the cell or the substrate in the one or more wells with the light from the light source; and spatially and temporally control illumination of the cell or the substrate in the one or more wells with one or more illumination parameters, wherein the one or more light guides is configured to provide uniform illumination of the light in the one or more wells of the tissue culture plate.

30. The method of Aspect 29, wherein the cell is a stem cell or a progenitor cell.
31. The method of Aspect 30, wherein the method is configured to spatially and temporally control stem cell or progenitor cell signaling and differentiation.
32. The method of Aspect 29, wherein the method further comprises screening for phototoxicity of the cell in response to light.
33. The method of Aspect 29, wherein the method further comprises screening for a candidate agent to determine whether the candidate agent modulates an activity of the cell.
34. The method of Aspect 29, wherein the cell expresses a light-sensitive protein.
35. The method of Aspect 34, wherein the method further comprises screening for the fluorescent protein expressed in the cell in response to light.
36. The method of Aspect 29, wherein the method is configured to photopolymerize the substrate.
37. The method of Aspect 29, wherein the substrate is a polymer.
38. The method of Aspect 29, wherein the substrate is a hydrogel.
39. The method of Aspect 38, wherein the hydrogel comprises one or more methacrylate groups.
40. The method of Aspect 39, wherein the hydrogel further comprises a photoinitiator.
41. The method of Aspect 40, wherein the photoinitiator is lithium phenyl-2,4,6-trimethylbenzoylphosphinate (LAP).
42. The method of Aspect 38, wherein said activating provides for photopatterning of the hydrogel in response to the light-activatable signal.
43. The method of Aspect 40, wherein said activating provides for crosslinkage of a first methacrylate group and a second methacrylate group within the hydrogel.
44. The method of Aspect 38, wherein the method is configured to modulate the stiffness of the hydrogel in response to light.
45. The method of Aspect 44, wherein the stiffness of the hydrogel is proportional to the light intensity of the light emitted by the light source.
46. The method of Aspect 44, wherein the hydrogel comprises one or more cells.
47. The method of Aspect 46, wherein the method further comprises screening for interactions of the one or more cell with an extracellular matrix within the hydrogel.
48. The method of Aspect 29, wherein the illumination uniformity of the light beam from light emitted by the light source is proportional to the thickness of the one or more light guides.
49. The method of Aspect 29, wherein the light guide is configured to decrease the variability of light intensity of the light beam emitted from the light source between each of the one or more wells of the tissue culture plate.

UTILITY

Example applications of the methods, devices, and systems of the present disclosure include use in high-throughput assays, such as high-throughput illumination and simultaneous recordings of various substrates or samples (e.g. light-responsive bacterial or mammalian cells grown in tissue culture, hydrogels, dyes) with user-defined patterns. The illumination device of the present disclosure can be combined with a robotic handler, a microscope, a spectrophotometer, or other conventional light detector to measure absorption, image fluorescence, or optical signals from the sample. Additional applications include high-throughput screens, directed evolution of light sensors and fluorescent proteins, phototoxicity screens, photopatterning of hydrogels, and cell signaling and differentiation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); hp, base pair(s); nt, nucleotide(s); i.m., intramuscular(ly); i.p., intraperitoneal (ly); s.c., subcutaneous(ly); and the like.

Example 1: Illumination Device for Spatial and Temporal Control of Morphogen Signaling in Embryonic Stem Cell Cultures Morphogen gradients are present throughout development and orchestrate the dynamic, coordinated movement and differentiation of cell populations. Spatially and temporally varying patterns of morphogens localize signaling to specific subpopulations of cells. Genetic perturbation and biomolecular treatment with pathway agonists or inhibitors have given immense insight into the key regulators of developmental progression, yet spatially-varying interactions between cell subpopulations and time-varying signal dynamics and thresholds remain largely unstudied, since such patterns of signaling are difficult to perturb and control in model developmental systems.

Light-responsive proteins from plants or bacteria have been adapted to control signaling and protein interactions in mammalian cells, enabling the optical techniques to stimulate signaling in a specific location, at a specific time. Following the discovery of light-gated ion channels, a great variety of light-responsive domains have been discovered, optimized, and repurposed for optogenetic control of cell signaling. Using the heterodimerizing system iLID 3 for optogenetic control of developmental ERK signaling, the spatiotemporal limits of ERK have been elucidated in the drosophila embryo. Also in drosophila, optogenetic clustering with Cryptochrome was used to inhibit Bcd transcription and Wnt signaling, or activate migration through Rho signaling or cell contractility. Optogenetics has also been applied to zebrafish development, for light-induced transcriptional activation of Nodal target genes and Rac-mediated cell migration.

Canonical Wnt/B-catenin signaling under optogenetic control using the illumination device of the present provided for mesendoderm differentiation and cell migration in embryonic stem cells.

The present disclosure provides a robust, programmable illumination system that can be easily incorporated into the workflow of routine tissue culture and allow spatial and temporal control of light intensity.

Design
Programmable Illumination Devices for hESC Optogenetic Stimulation

Figure 6:
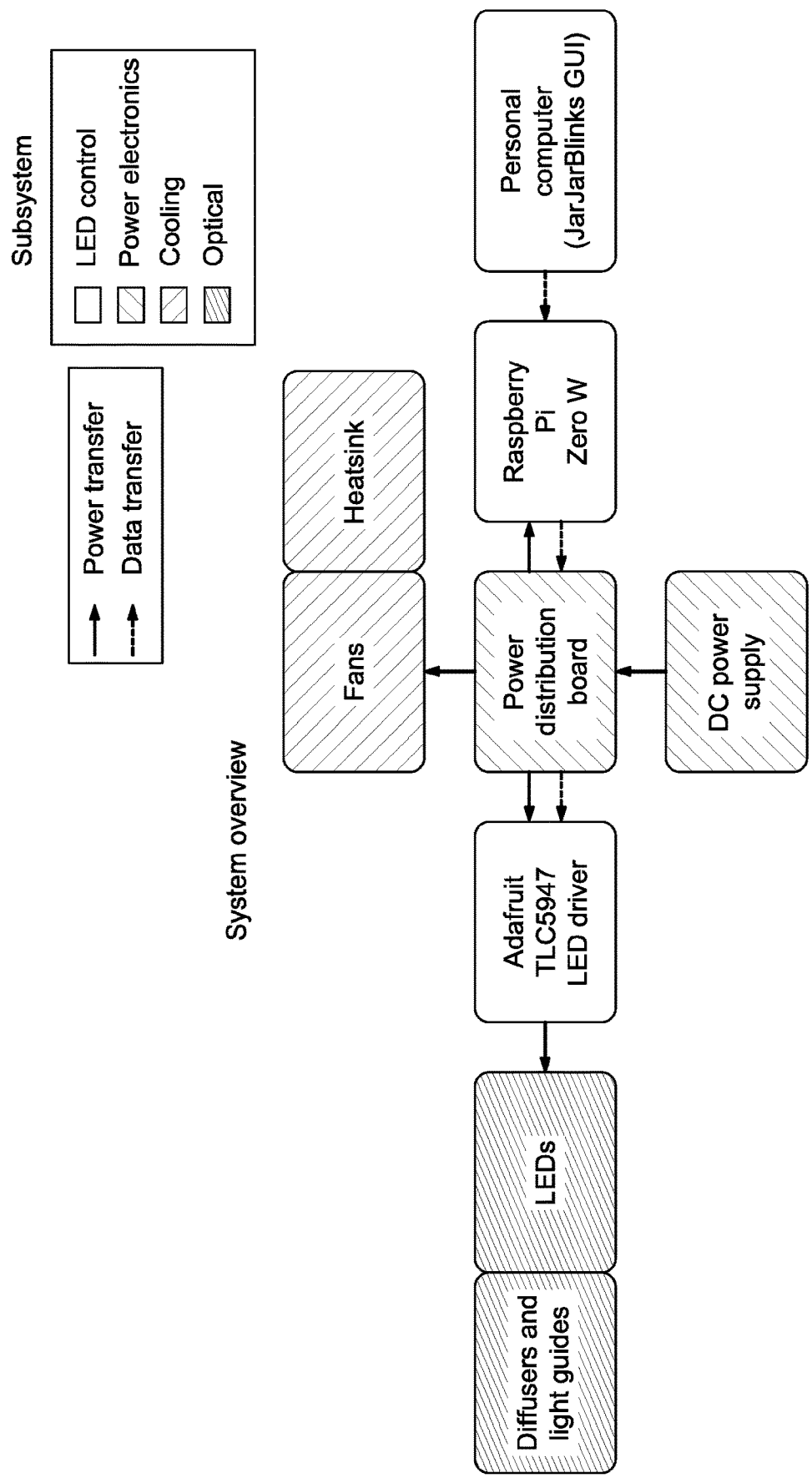
FIG. 6. System block diagram of LAVA device.

To enable precise control over the intensity, timing, and location of optoWnt stimulation in hESC cultures, illumination devices were engineered that incorporate into the workflow of stem cell culture, termed LAVA devices (light activation at variable amplitude; e.g. illumination device of the present disclosure). (FIG. 1, Panel A). LAVA devices project user-defined light patterns onto 24-well or 96-well tissue culture plate kept inside a tissue culture incubator (FIG. 1, Panels B-C, FIG. 6). In brief, light from LEDs passes through optical elements that ensure uniform illumination of the multiwell plate. For stimulation of optoWnt, blue LEDs emitting at a central wavelength of 470 nm was chosen to match the Cry2 absorption spectrum (FIG. 7), though LEDs of other colors can be easily substituted for use with other optogenetic systems. An electronics subsystem allows programmed control of illumination intensity and temporal sequences, with independent control of each well. Spatial precision is conveyed through an intensity mask attached to the culture plate. The hardware design also includes a cooling system and vibration isolation to ensure cell viability. Lastly, for ease of use, a graphical user interface (GUI) was developed to wirelessly program the illumination intensity and temporal sequences for each well (FIG. 8, Panels A-B). A detailed protocol was provided for LAVA assembly, as well as design considerations, characterization, and proof of concept applications in spatiotemporal control of Wnt activation.

Optimization and Characterization of Illumination Uniformity

Figure 2B:
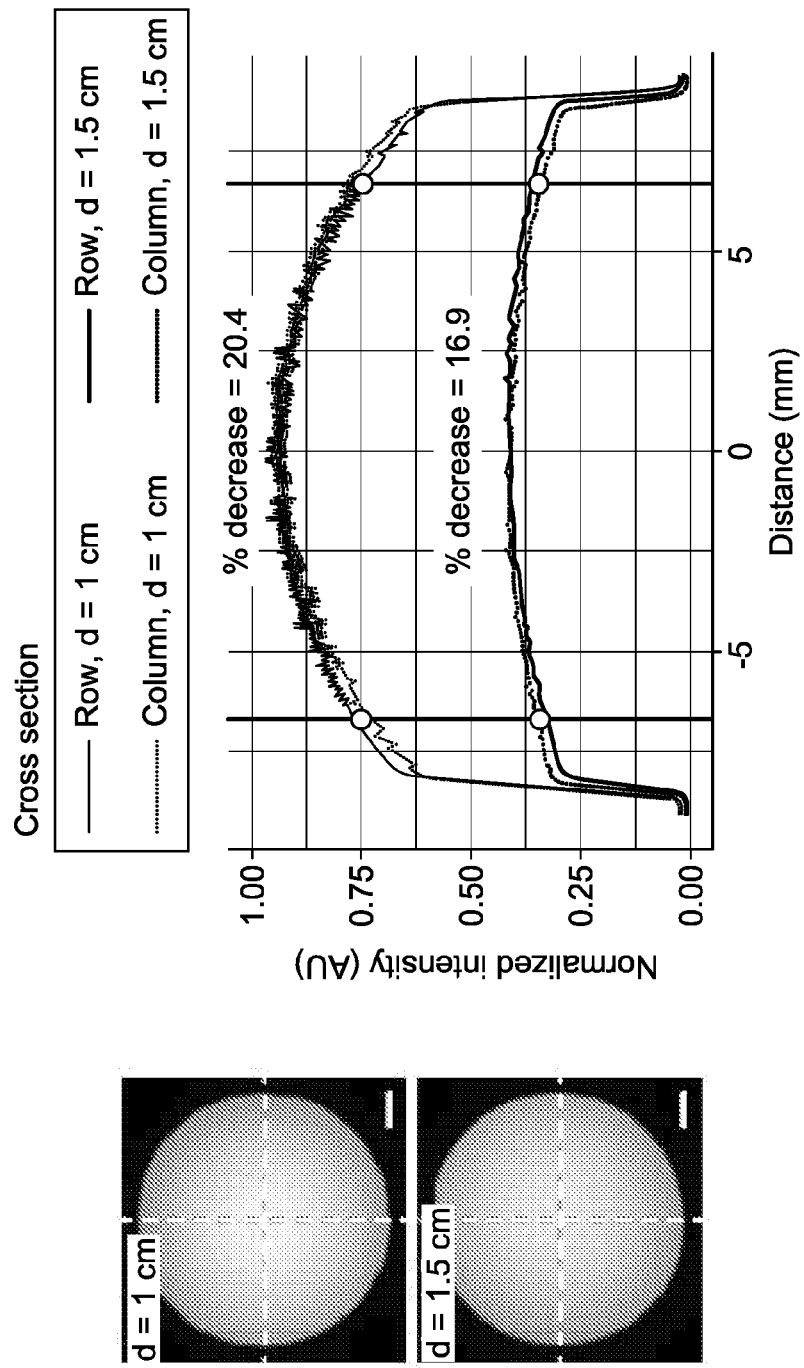
Figure 2C:
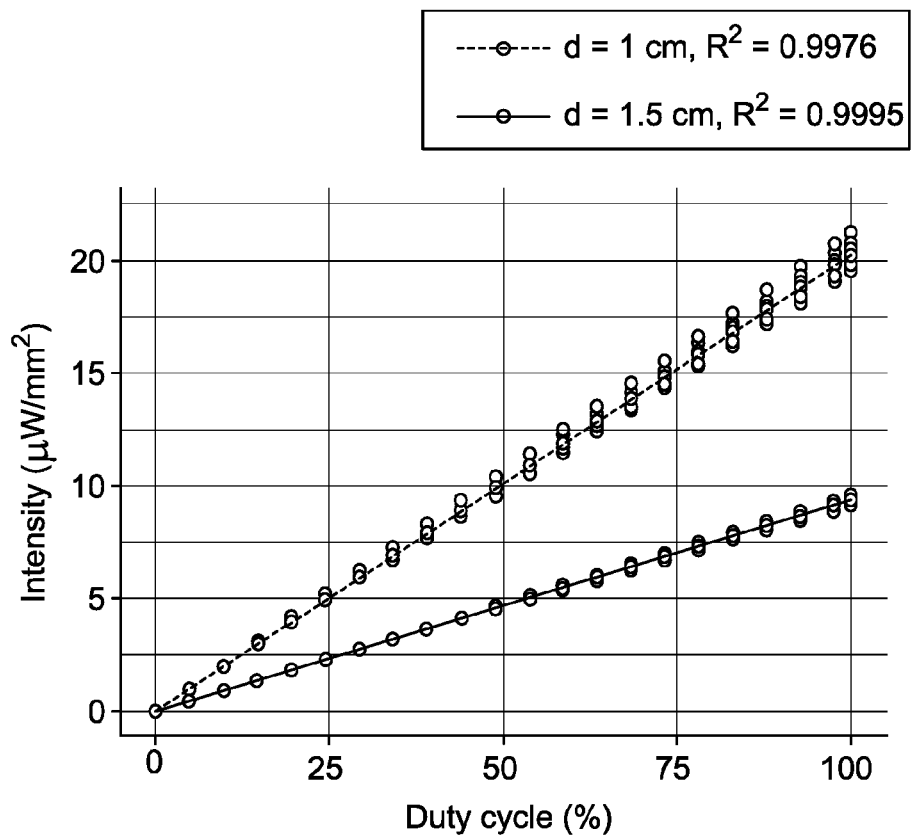
Figure 3A:
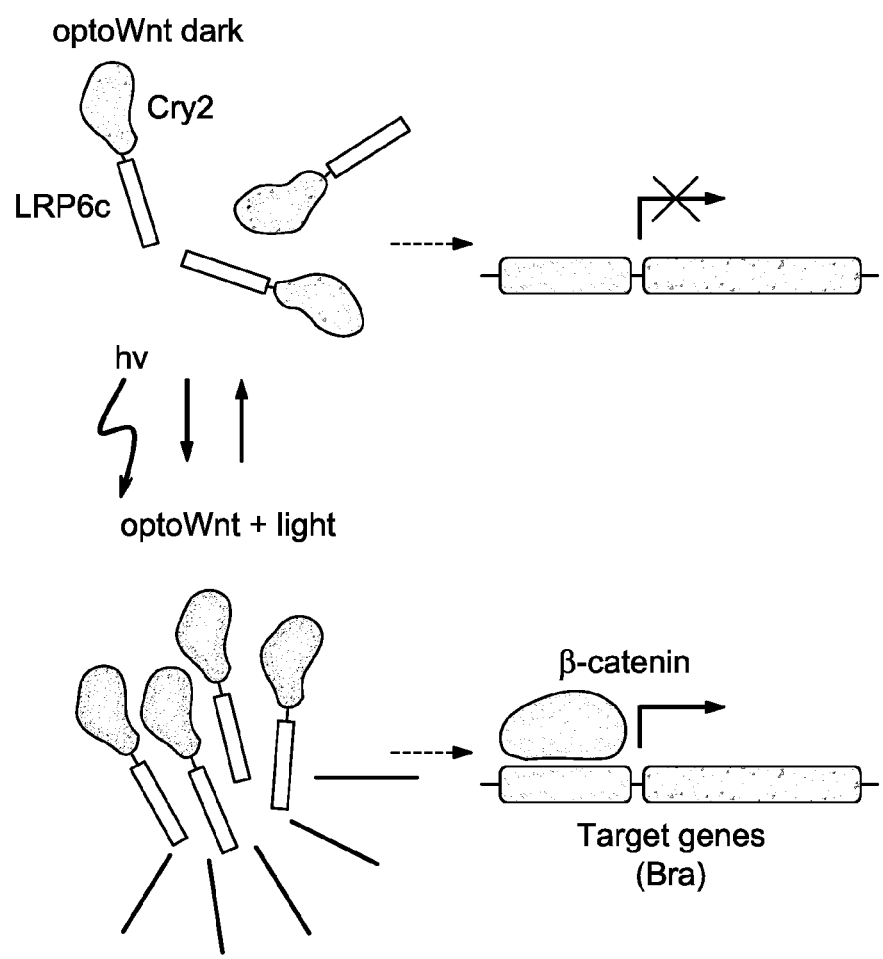
FIG. 3, Panels A-D. Optogenetic induction of Bra expression is light-dose responsive.
Figure 3B:
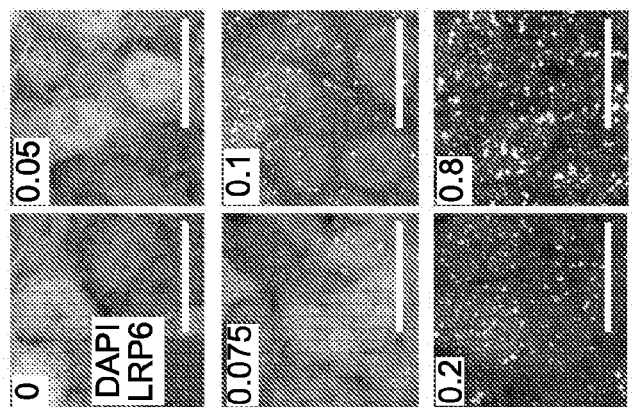
Figure 3B:
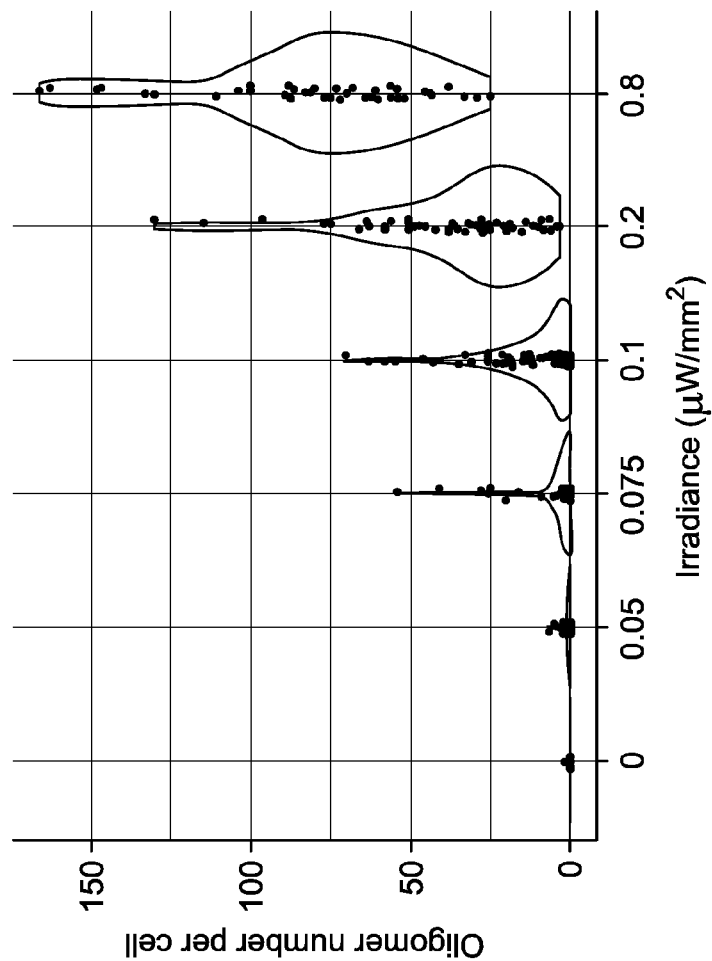
Figure 3C:
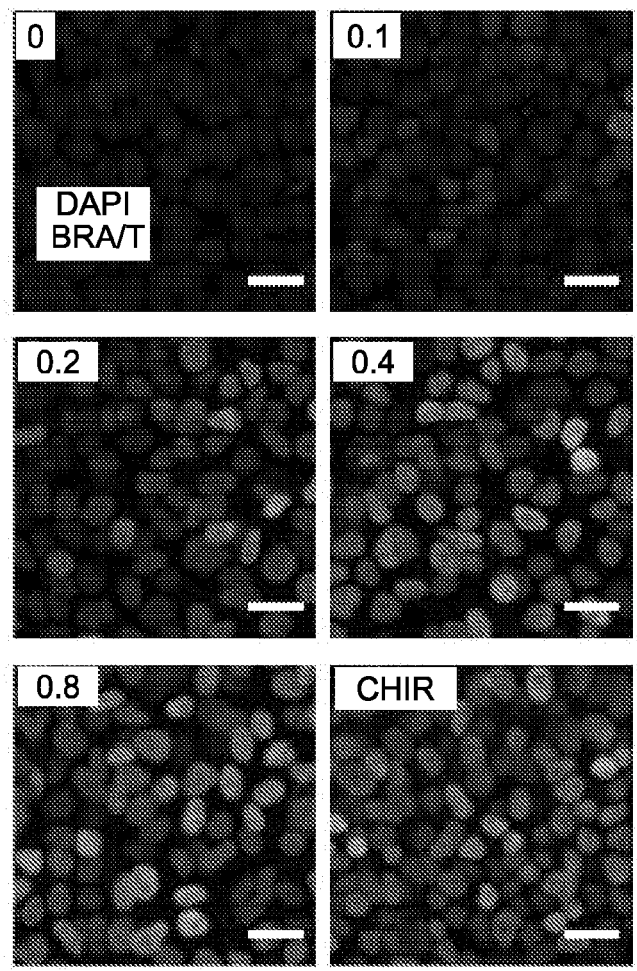
Figure 3D:
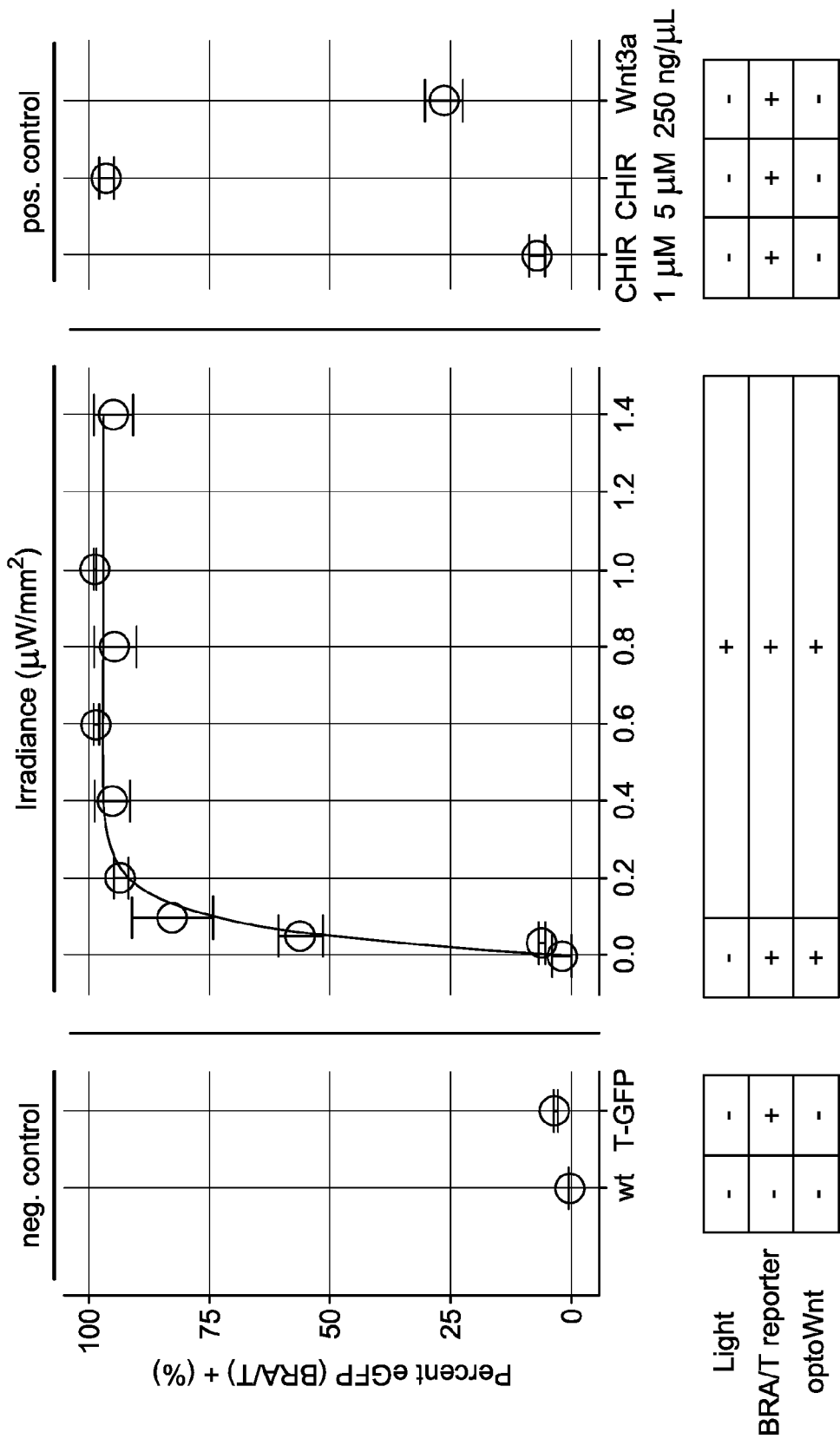
Figure 11:
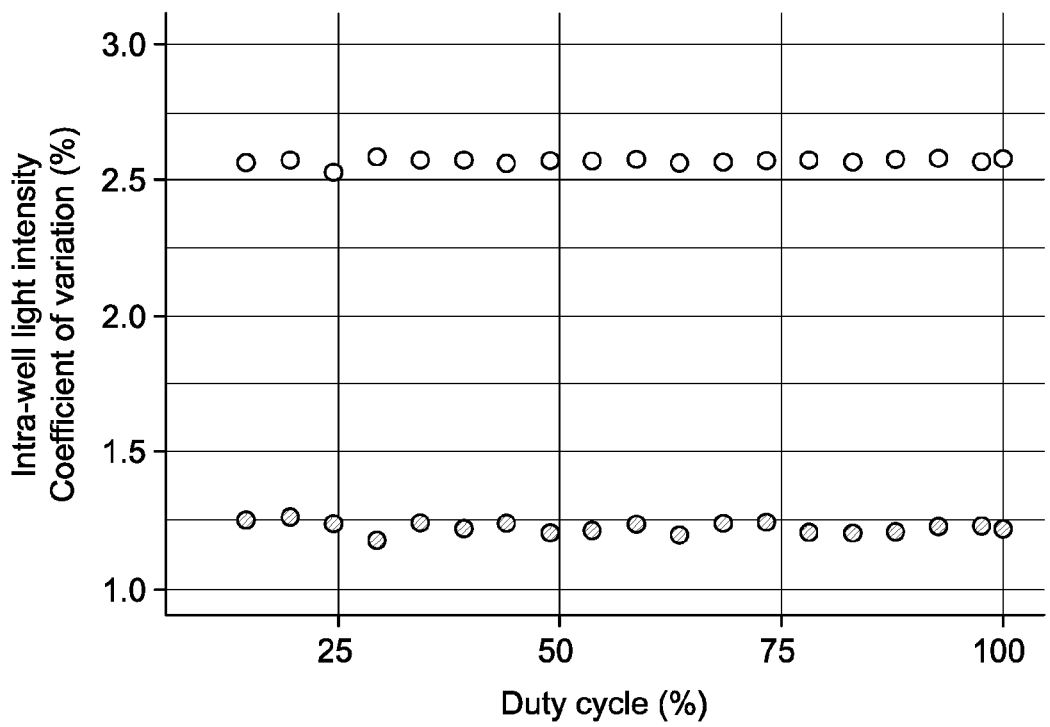
FIG. 11. Coefficient of variation of light intensity between the 24 independent light channels measured at different programmed intensities. Green points correspond to optical configuration with d=1 cm, violet points show optical configuration with d=1.5 cm.

The LAVA optical system design was established by modeling LAVA in the optical ray tracing software Zemax OpticStudio and optimizing for uniform well illumination (FIG. 2a). For simplicity and compactness, optical diffusers and scattering from the 3D-printed light guides were used to improve illumination uniformity instead of lenses. In the Zemax model, parameters such as LED position on the circuit board, diffuser strength, and light guide dimensions were optimized to reduce intensity drop-off at the edges of the tissue culture well (FIG. 4, Panels A-H, FIG. 5, Panels A-E). Modeling results showed that the parameter with strongest effect on uniformity was the axial thickness, d, of the two 3D-printed light guides (labelled in FIG. 1, Panel B). Based on the modeling results, LAVA devices were fabricated and experimentally verified well uniformity by imaging LAVA wells under a low-magnification microscope (FIG. 2, Panel B). Measurement of light intensity as a function of radial distance confirmed relatively uniform illumination which improved with increasing d at the expense of maximum light intensity. Increasing d from 1 cm to 1.5 cm improved the intensity decrease at the well edge from 20.4% to 16.9%, i.e. a roughly 20% improvement in uniformity. A larger d also resulted in a two-fold improvement in well-to-well variability between the 24 independent wells (2.6% versus 1.2% coefficient of variation) (FIG. 11). Considering there are many experimental applications where intensity of illumination is paramount to well uniformity, the two hardware configurations for LAVA can be summarized as follows: (1) a low-intensity, high-precision configuration at d=1.5 cm where intensity can be programmed 0 to 10 $\mu W/mm^2$ in 0.0024 $\mu W/mm^2$ increments with improved illumination uniformity and well-to-well variability and (2) a high-intensity, low precision configuration at d=1 cm where well intensity resolution, variability, and uniformity are sacrificed for a doubling in light intensity (FIG. 2c).

Results
Intensity Control of Optogenetic Stimulation Reveals Brachyury Expression Level is Dependent on LRP6 Oligomer Number and Size During mammalian embryonic development, gradients in Wnt signal intensity control the progression of cell lineage commitment and axis patterning. In hESCs, the intensity of Wnt signaling similarly modulates cell lineage commitment and differentiation potential. Equipped with a method for optogenetic stimulation of cell cultures, LAVA and a previously-established clonal optoWnt knock-in line was used for activation of canonical Wnt signaling in hESCs. In contrast to simple on/off control of Wnt signaling.

Figure 12A:
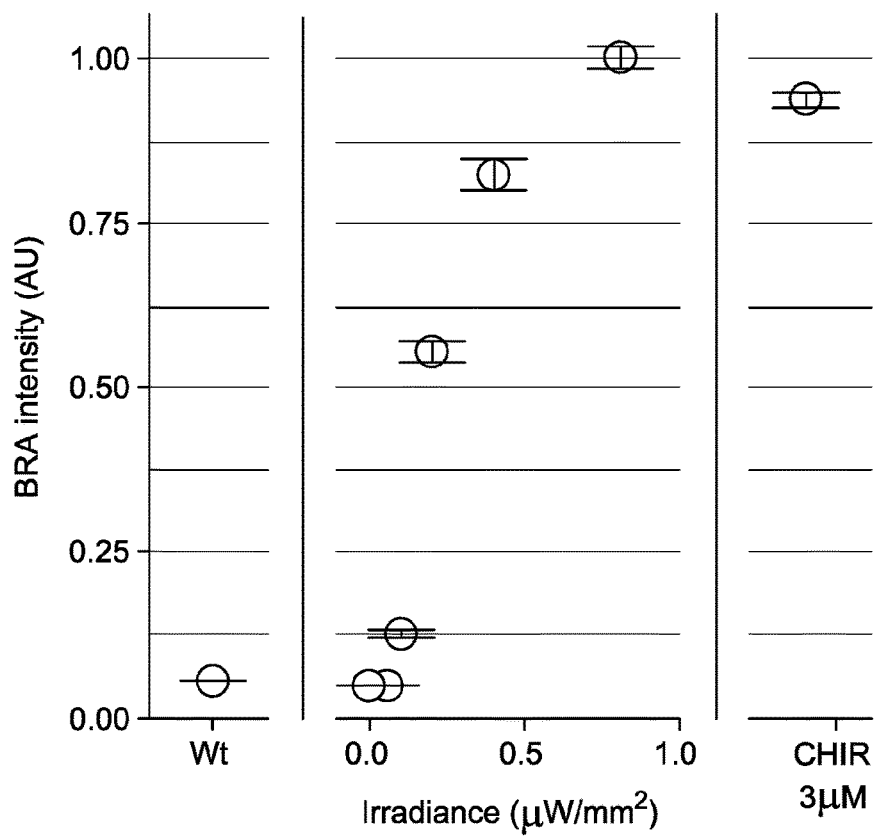
FIG. 12, Panels A-B. Panel A) Immunostaining quantification for average Bra intensity per hESC in response to increasing light intensity after 24 hr illumination or 3 μM CHIR treatment. Graph shows mean±1 s.d. n=3 replicates. Panel B) Flow cytometry histograms of optoWnt hESCs expressing eGFP reporter for Bra after 24 hr illumination at varying light intensities. Graph shows sum of n=3 replicates.
Figure 12B:
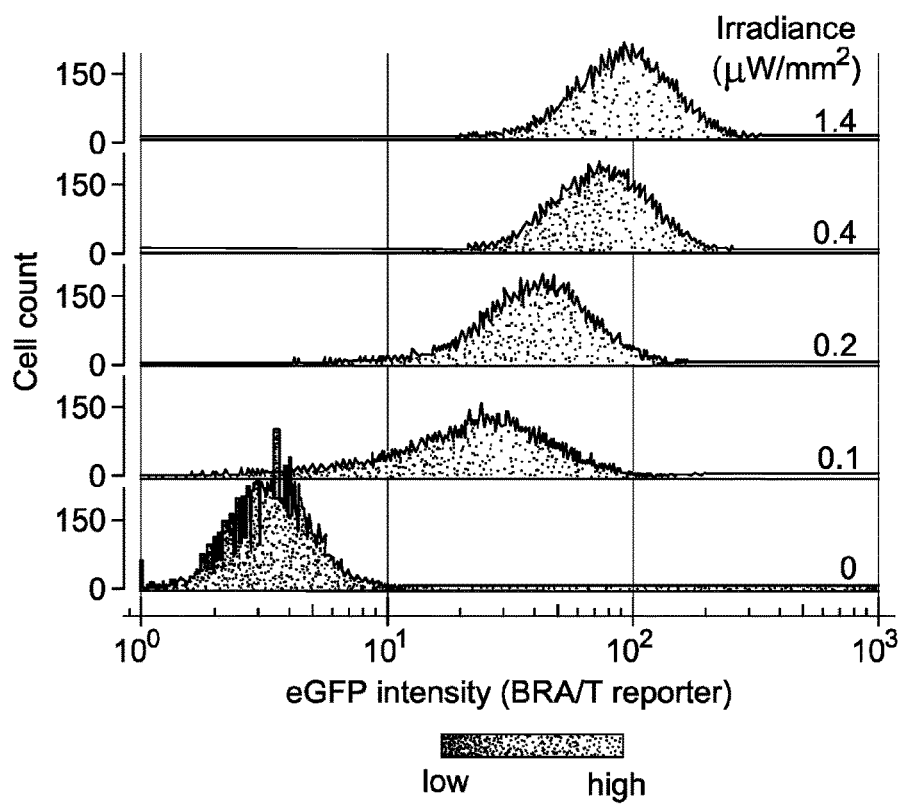
Figure 13A:
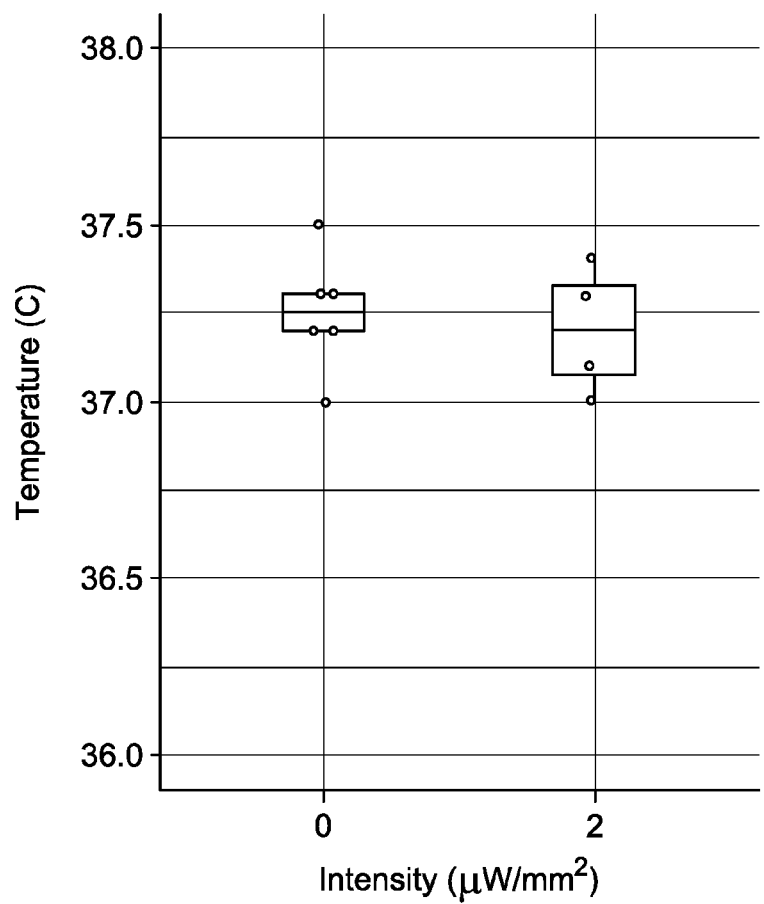
FIG. 13, Panels A-D. Phototoxicity during continuous optogenetic stimulation of hESC cultures.
Figure 13B:
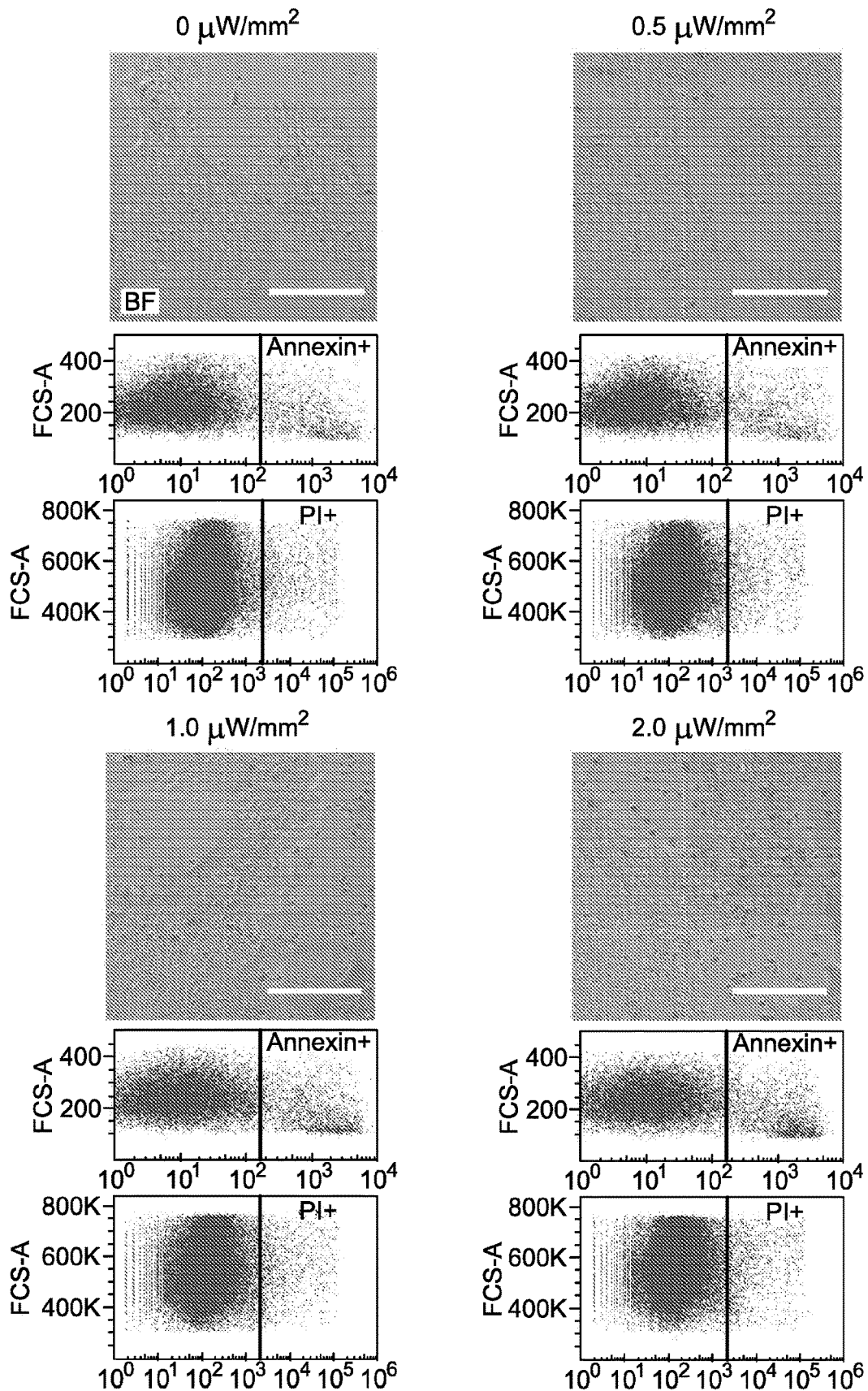
Figure 13D:
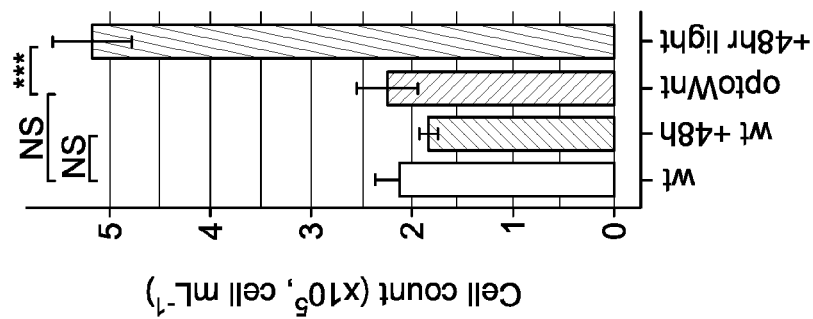
Figure 13C:
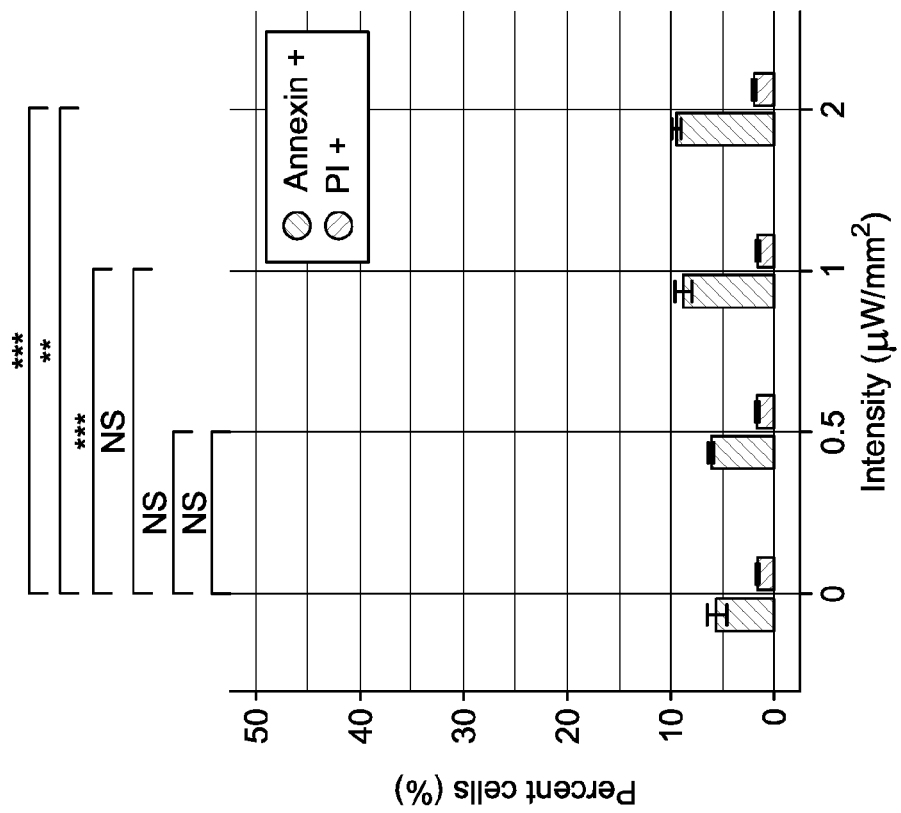

Since Cry2 oligomerization is a dynamic, reversible process where clustering is triggered upon photon absorption, it was hypothesized that the fraction of 'activated' Cry2 proteins in a cell can be controlled with light intensity (FIG. 3, Panel A). Indeed, the number and size of visible LRP6 oligomers in a cell increased monotonically with light intensity (FIG. 3b). To determine whether increased Cry2 oligomerization translated to a stronger Wnt/i-catenin signal intensity, expression of Brachyury (Bra, also known by its gene name, T) was probed, a target of Wnt signaling and regulator of mesendoderm and primitive streak differentiation. Following a similar trend to Cry2 oligomerization, the mean intensity of Bra immunostaining increased with light intensity, showing that an increased number and size of LRP6 clusters induces a stronger differentiation signal (FIG. 3, Panel C; FIG. 12, Panel A).

To better quantify the variability of Bra expression at a single-cell level, a clonal hESC cell line co-expressing the optoWnt system and an cGFP reporter was generated for endogenous Bra expression. Live-cell analysis with flow cytometry showed a heterogeneous response to Wnt stimulation at low light intensities (median, Q) and a more homogenous, higher eGFP expression at higher intensities (median, Q) (FIG. 12, Panel B). Maximal light-induced activation increased Bra expression by ~33-fold over uniluminated optoWnt hESCs, which notably showed no detectable activation in the dark. Quantification of the percentage cGFP-positive cells showed an exponential increase with light intensity that greatly exceeded activation achieved with high concentrations of pathway agonist Wnt3a (FIG. 3, Panel D). Fitting to an increasing exponential decay function showed a very rapid increase in Bra expression at low light intensities (time constant τ=0.07, see methods), with saturation reached at ~0.4 µW/mm2. The high sensitivity at lower light intensities shows a binary switch for onset of Bra expression above a signaling threshold, followed by a monotonic increase in Bra expression levels in a light dose-dependent manner.

Analysis of Phototoxicity Reveals No Detectable Effects on hESC Health Below a 1 µW/mm2 Illumination Intensity Threshold Since high intensity light can induce phototoxicity in cells, the phototoxicity threshold was analyzed for hESC cultures using the illumination devices of the present disclosure. Continuous operation of high-intensity LEDs can cause heating at high intensities (FIG. 13, Panel A). For all optogenetic stimulation an intensity range of under 1 $\mu W/mm^2$ was used (specifically, 0.8 $\mu W/mm^2$). Under this condition, no decrease in pluripotency markers Sox2, Nanog, and Oct4 were observed after 48 hrs of illumination of wild-type hESCs, as well as no spontaneous Bra+ mesendoderm differentiation (FIG. 13, Panel D). Notably, since saturation of percentage Bra+ optoWnt cells occurred at ~0.4 µW/mm², the operating range of optoWnt stimulation falls below the 1 µW/mm² phototoxicity threshold.

Temporal Control of optoWnt Shows that Sustained Wnt Signaling is Necessary for Bra Activation In addition to intensity control, LAVA enables temporal control of illumination patterns (FIG. 4, Panel A). Oscillatory Wnt signals regulate mesoderm segmentation while local pulses of Wnt signaling are present during primitive streak patterning and neural tube development. Given the reversible oligomerization of Cry2, it was concluded that the optoWnt system can be readily applied to studying temporal dynamics of Wnt signaling.

Figure 4C:
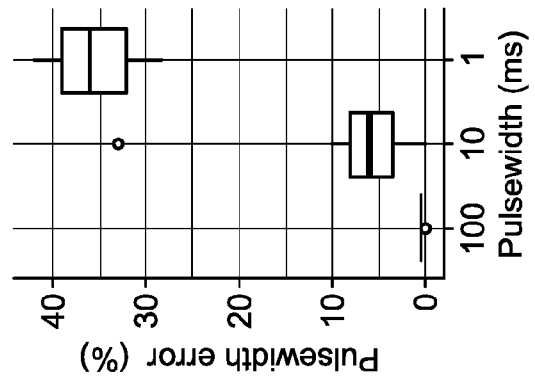
FIG. 4, Panels A-D. Characterization of temporal control using LAVA devices.
Figure 4B:
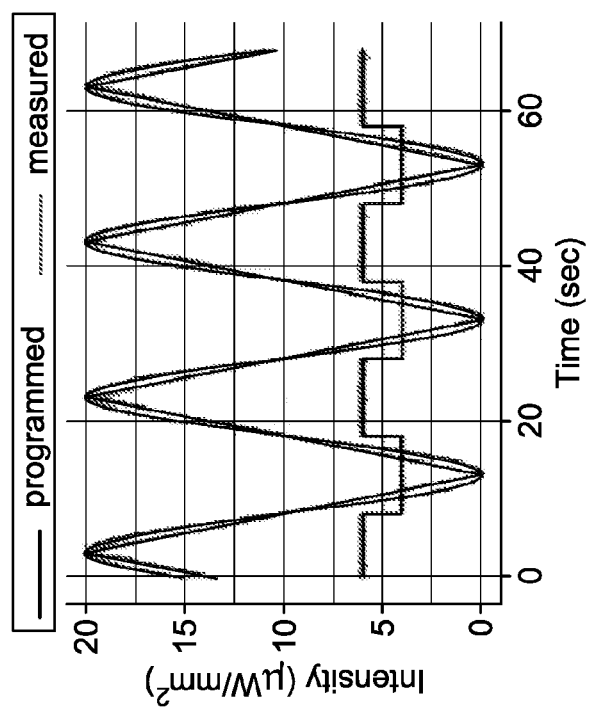
Figure 4A:
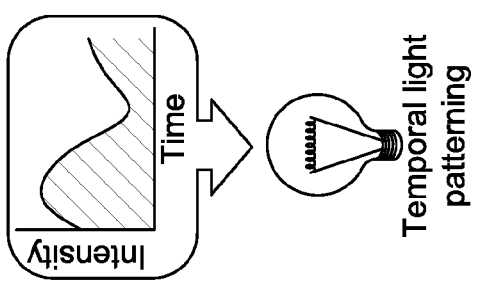
Figure 4D:
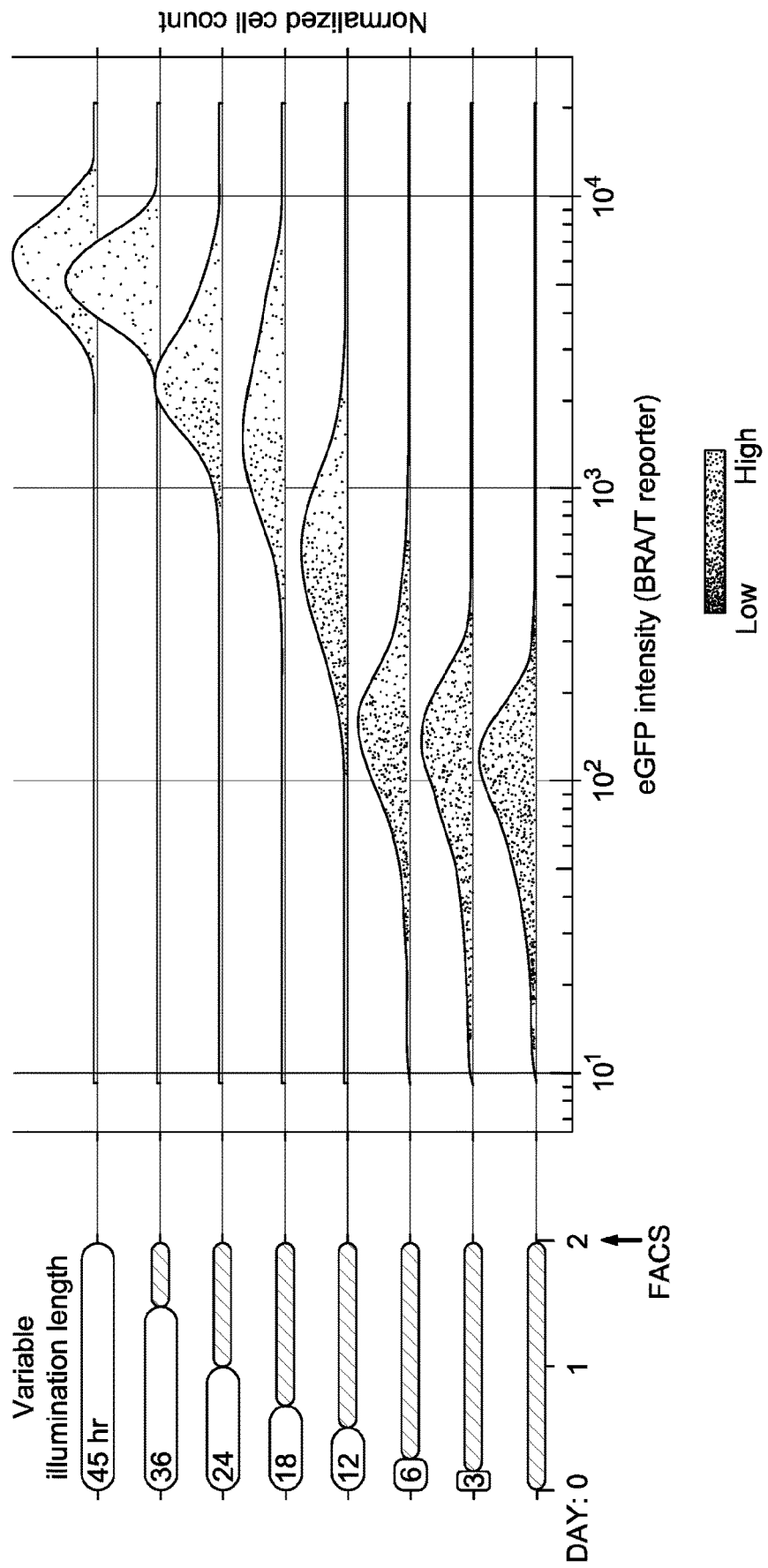
Figure 5A:
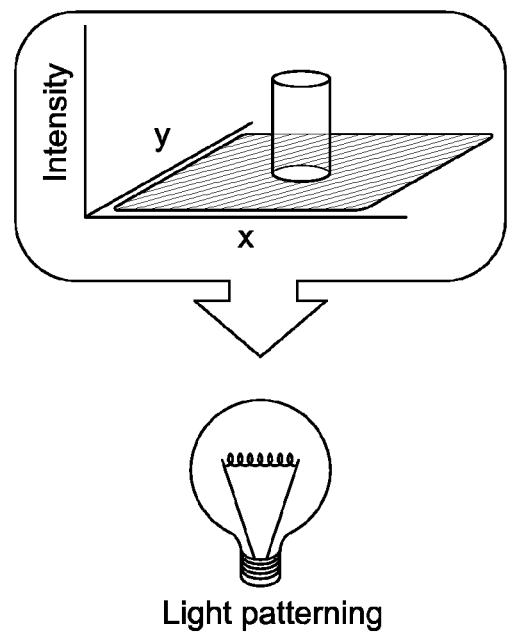
FIG. 5, Panels A-F. OptoWnt induces epithelial to mesenchymal transition and primitive streak-like behavior.
Figure 5B:
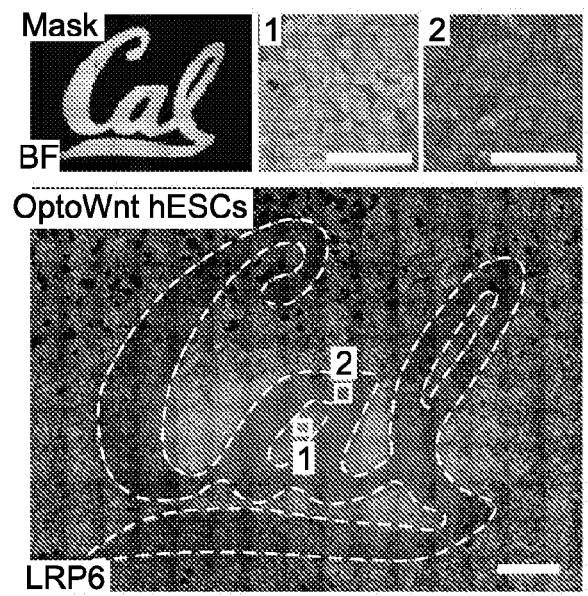
Figure 5C:
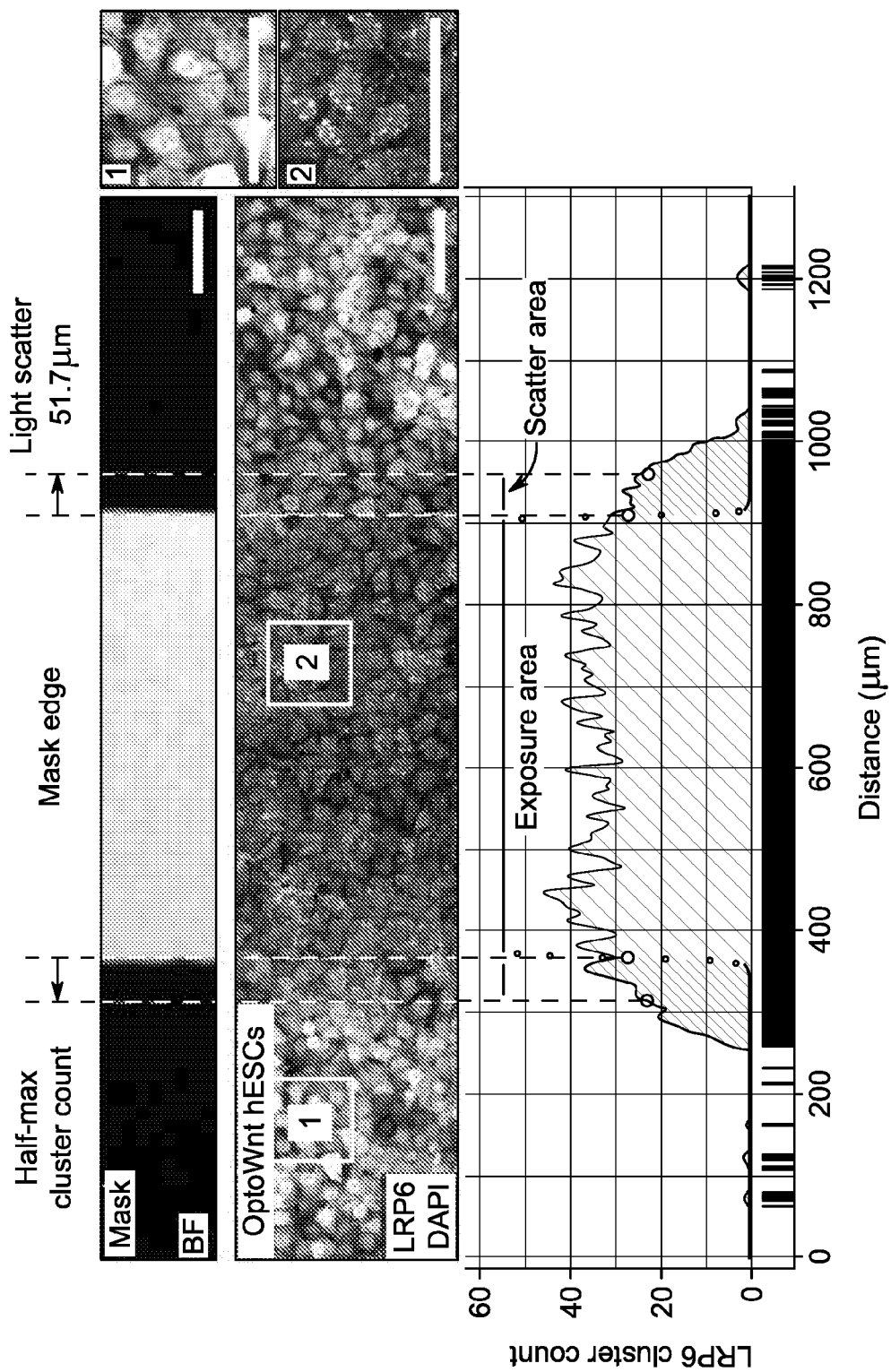
Figure 5D:
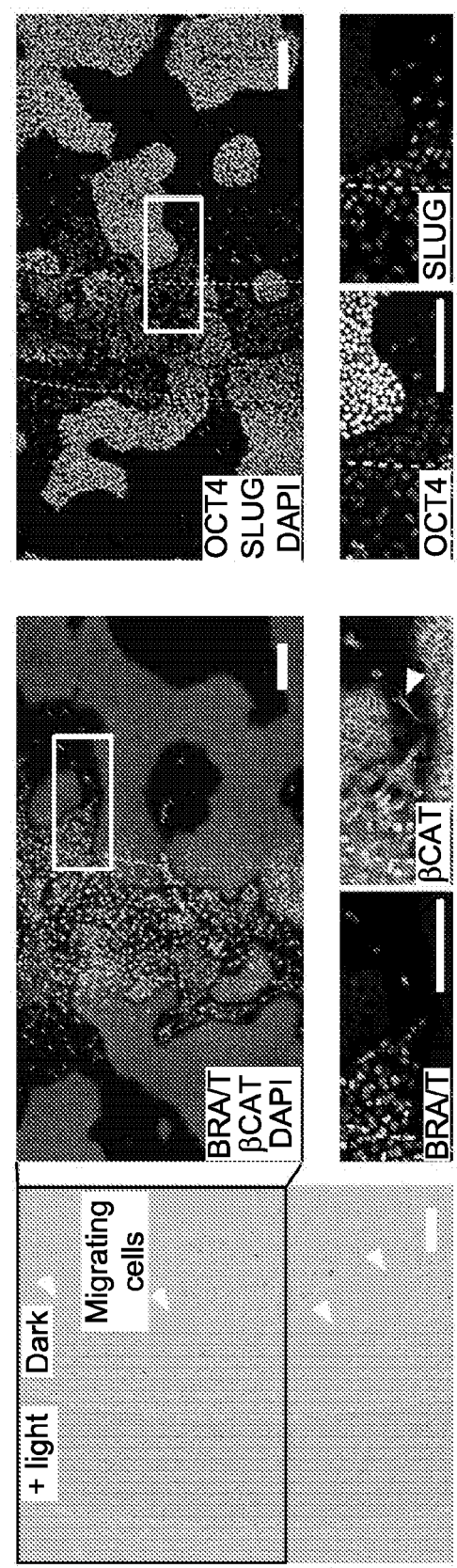
Figure 5E:
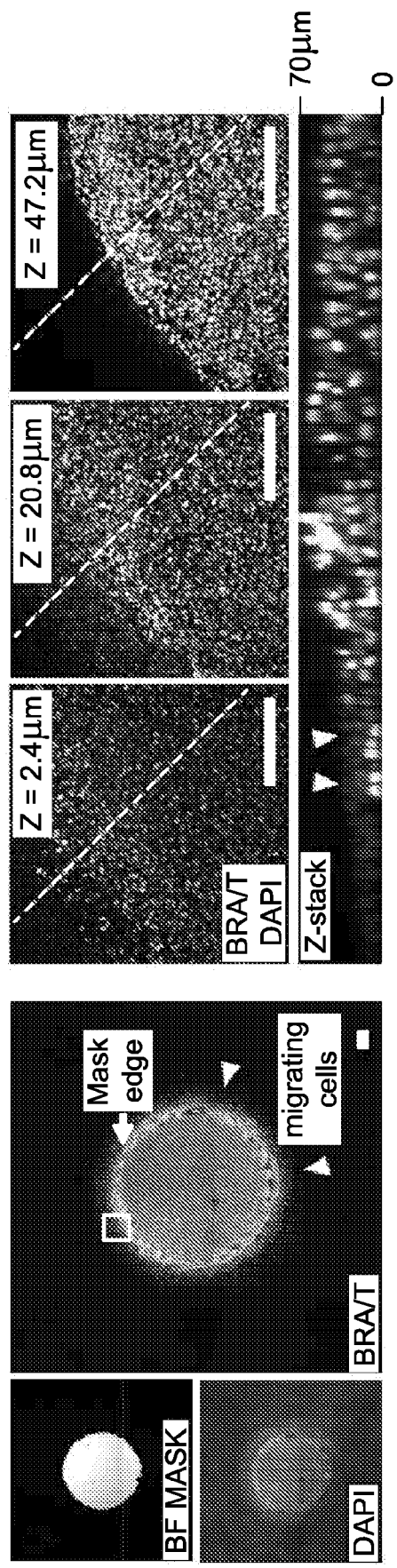
Figure 5F:
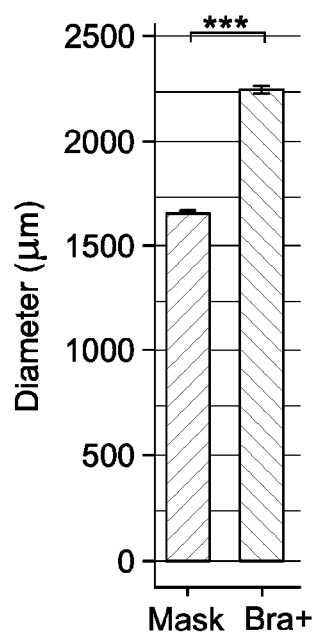
Figure 14:
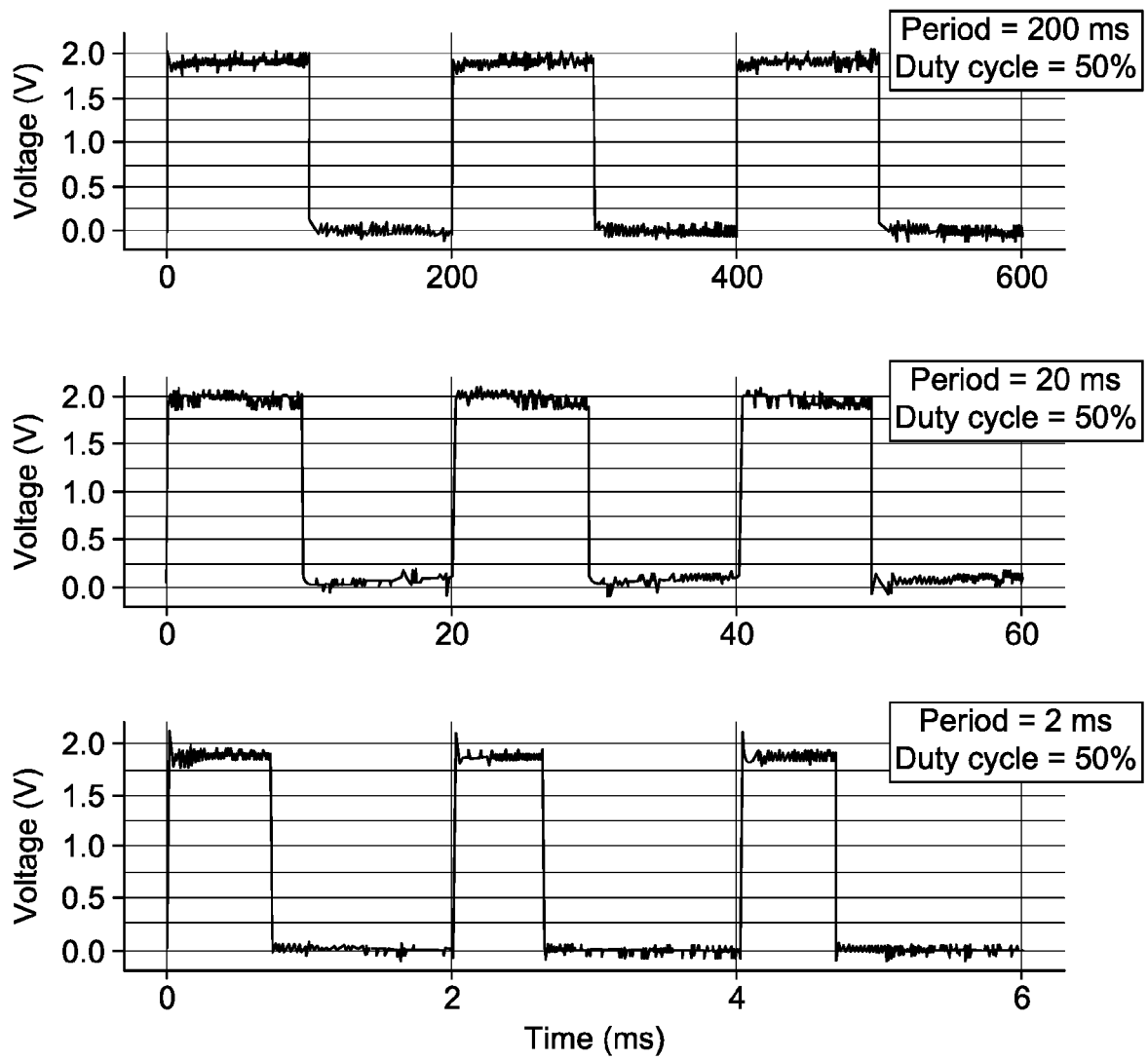
FIG. 14. Illumination power meter measurements of programmed blinking sequences show signal inaccuracy at 1 ms pulses. Voltage signal from power meter measured with oscilloscope and is proportional to irradiance.

A LAVA GUI was designed to allow users to input the desired temporal light pattern for each well. The GUI wirelessly communicates with the LAVA board to set the illumination patterns for the duration of the experiment. The user can set each of the 24 channels to one of three modes: (1) constant illumination at a specified intensity; (2) blinking at a specified intensity, duty cycle, and period; and (3) a series of linear or sinusoidal functions at specified function parameters. Multiple piecewise functions can be programmed in sequence, enabling a variety of complex temporal light patterns (FIG. 4, Panel B). The shortest possible blink, i.e. the temporal resolution of the device, was set to 1 ms in firmware, though it was observed a significant drop in the accuracy and precision of stimulation at pulsewidths below 10 ms (FIG. 4c, FIG. 14)

The next step was to determine whether sustained Wnt activation is required for hESC mesendoderm differentiation. With the presence of autoregulatory feedback loops and the potential for sustained Wnt signaling following a 24 hr pulse of CHIR treatment in mESC gastruloids, it sought to determine whether sustained Wnt activation is necessary for Bra expression in hESCs, or whether shorter activation durations are sufficient for inducing a differentiation program. OptoWnt cultures expressing a T/eGFP reporter were illuminated with varying durations of light and quantified eGFP fluorescence with flow cytometry. After withdrawal of illumination, T/cGFP levels decreased showing that sustained illumination and optoWnt activation is necessary for a sustained Bra transcriptional response in our hESC culture system.

Figure 15A:
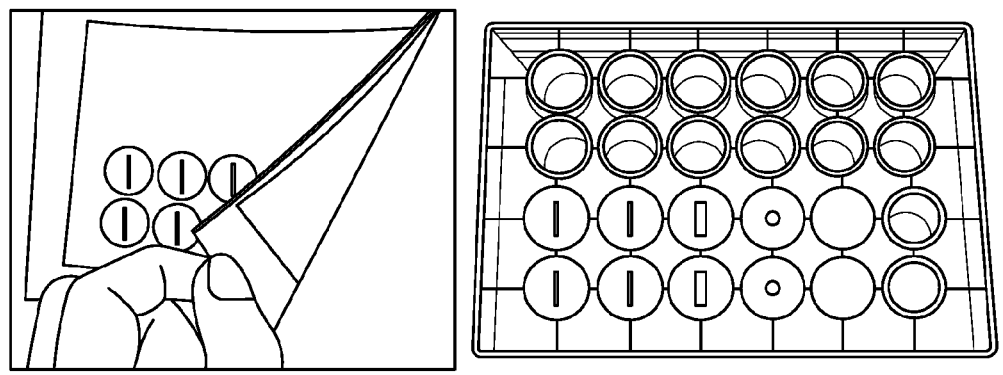
FIG. 15, Panels A-C. Panel A) Images of adhesive die-cut masks applied using transfer tape (top) onto 24-well cell culture plate (bottom). Panel B) Brightfield images of die-cut mask illustrate resolution limit of cutter. Scale bar 3 mm. Panel C) Schematic of light scattering from photomask.
Figure 15B:
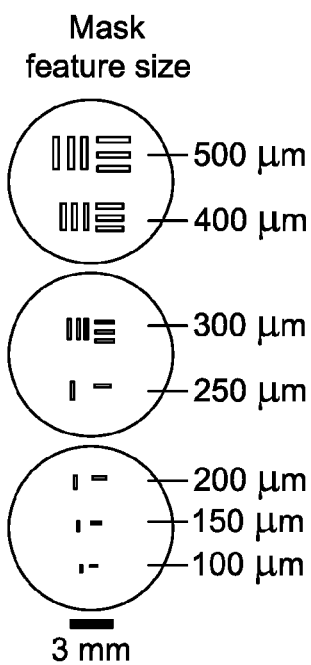
Figure 15C:
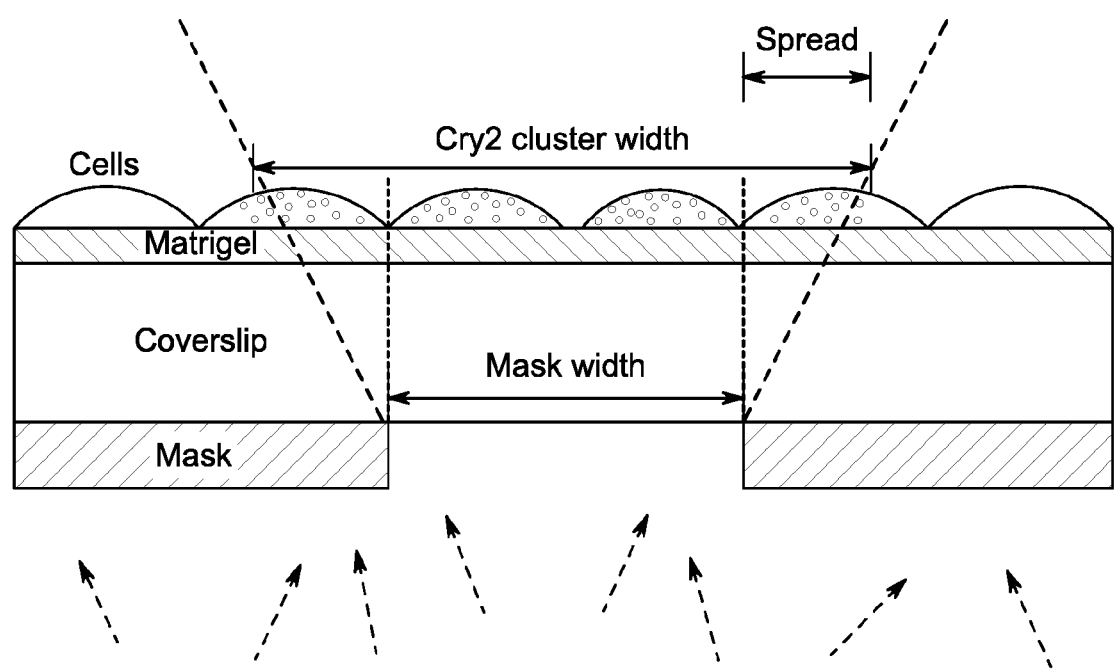

Spatial Localization of Wnt Signaling and hESC Differentiation as a Model for Early Embryonic Wnt Patterning An additional advantage of optogenetic control is the ability to manipulate the spatial location of signal activation (FIG. 5, Panel A). Though precise patterned illumination can be achieved with confocal scanning or the use of spatial light modulators, the cost and complexity of such microscope systems are restrictive when low-resolution light patterns are sufficient. To more easily incorporate spatial light patterning during cell culture, die-cut intensity masks were designed that can be adhered to the tissue culture plate during illumination (FIG. 15, Panel A). The mask feature size was limited by the cutting resolution of the die cutter to ~150 µm (FIG. 15, Panel B). In this way, wells of the 24-well plate were illuminated with arbitrary light patterns and induce optoWnt clustering only in illuminated regions (FIG. 5, Panel B). Since the mask is placed underneath the tissue culture plate, it was anticipated that there would be light scattering through the plate bottom (170 µm-thick coverglass) that would compromise the mask resolution (FIG. 15, Panel C). To quantify the extent of light scattering, the number of LRP6 clusters was measured as a function of distance beyond the mask edge and found that clusters were induced ~50 µm from the mask edge. corresponding to a ~100 µm patterning resolution (see methods for calculation) (FIG. 5, Panel C).

During development, cells migrating through the primitive streak break away from the epithelial cell layer. scattering as single cells and adopting a mesenchymal morphology that initiates spatial patterning of the epiblast. To visualize the interaction between epithelial cells and differentiating mesendoderm, the spatial light patterning capability of LAVA was used to illuminate optoWnt hESC cultures with an arc of light (FIG. 4, Panel E). Cells in the illuminated are broke away from hESC colonies, adopted a mesenchymal morphology, and migrated up to ~500 µm beyond the boundary of the light pattern. Given the 100 µm resolution of patterning, the possibility that cells were activated by light scattering outside of the mask pattern was excluded. Immunostaining confirmed that these migratory cells expressed Bra, while surrounding unilluminated cells retained epithelial morphology with no detectable Bra expression. In addition, migratory cells showed a decrease in Oct4 expression, a shift in pi-catenin localization away from the plasma membrane, and an increase in Slug expression, all consistent with cells undergoing an epithelial-to-mesenchymal transition.

Illumination with a 1.5 mm-diameter circle of light allowed to better quantify migration outside the area of illumination (FIG. 4f). When confined by a higher seeding density, illuminated cells grew vertically upwards, stacking 4 to 6 cell diameters in height (~70 µm). Axial slicing with confocal imaging showed that cells in the illuminated region stained positive for Bra and migrated up to ~300 µm outside of the illuminated region by diving underneath the epithelial cell layer. Taken together, these data show that optogenetic Wnt activation is sufficient for inducing a migratory cell phenotype and that patterned illumination can be used as a tool to further study Wnt patterning and gastrulation-like events in culture.

Discussion

Optogenetic control of Wnt signaling, optoWnt, and the LAVA system were used to dynamically control morphogen signaling in hESCs. Through extensive characterization of the LAVA board light patterning, precise manipulation of stem cell signaling was demonstrated to be achieved in space and time. Applications for LAVA devices can be extended to other biological systems and signal pathways for mechanistic spatiotemporal studies or high-throughput optogenetic screens.

Design of LAVA Beards for Quantitative Control of Cell Signaling

A number of challenges exist for robust, long-term illumination of cell cultures. Cell toxicity from photodamage or overheating is a significant drawback during optogenetic stimulation and can cause cell death or non-specific activation of signaling pathways. Illumination uniformity across a region of interest is critical as well, since optogenetic signaling is dependent on light dosage (FIG. 3, Panel D). Because of this, a minimal intensity drop-off toward edges of the well is essential for uniform optogenetic activation within a well.

The illumination device of the present disclosure allows defined and high-throughput control of optogenetic signaling in cell cultures. In designing the LAVA boards, the optical system was optimized for uniform well illumination (<17 drop-off) and designed electronics that enable 16-hit control of intensity for 24 independent channels with arbitrary temporal patterns (1 ms resolution) and spatial patterns through use of a photomask (100 µm resolution). In this manner, two versions of the LAVA boards were that can illuminate 24-well or 96-well tissue culture plates. Heating and vibration control were incorporated, characterized the phototoxicity threshold for hESCs under continuous illumination, and developed a user interface to easily upload desired intensity patterns for each channel to LAVA devices kept in a 37° C. tissue culture incubator.

Efficiency and Dose-Responsiveness of Optogenetic Wnt/B-Catenin Signaling

OptoWnt stimulation using the LAVA devices had high efficiency of Cry2 clustering and Bra expression in hESCs. Following 24 hrs of continuous illumination at 0.4 µW/mm2, Bra expression was evident in >98% cells, a cell percentage comparable to CHIR treatment and higher than Wnt3a treatment (FIG. 3, Panel D). Given that optoWnt modulates signaling at a node high in the Wnt signaling cascade, i.e. at the Wnt-specific co-receptor LRP6, this high optoWnt efficiency is a significant advantage—optoWnt is thus as efficient as the commonly used CHIR small-molecule agonist with the added advantage of high Wnt pathway specificity given the potential non-specific effects of GSK3B inhibition.

Additionally, the strength of optoWnt pathway activation was dose-responsive to light intensity. The size and number of detectable LRP6c clusters per hESC increased with light intensity and correlated with increased Bra expression (FIG. 3, Panel B). This is likely due to an increased fraction of photoactivated Cry2 molecules at higher illumination intensities and suggests a role for LRP6 cluster size or abundance in regulating B-catenin destruction complex dissociation 38 or saturation. Analysis of the single-cell expression profiles in response to varying light doses also elucidated signaling thresholds for Wnt pathway activation. While the percentage of Bra+ cells increased sharply with light intensity and saturates at 0.4 µW/mm2, Bra expression levels increased more gradually and saturate at ~0.8 µW/mm2, which suggests a binary switch for the onset of Bra expression above a certain signaling threshold followed by a light dose-dependent increase in expression level (FIG. 3, Panel D; FIG. 12, Panel A). Such signaling thresholds can be further studied through super-resolution imaging and quantification of cluster properties. This operating range for optoWnt activation (0-0.8 µW/mm$^2$) falls below the measured phototoxicity threshold of 1 µW/mm$^2$ (FIG. 13).

Spatial and Temporal Control of Wnt Signaling Dynamics

The LAVA boards and optoWnt system open a wide range of possibilities for studying the role of Wnt dynamics in ESC signaling. The reversibility of Cry2 clustering and Bra expression (FIG. 4, Panel D) combined with case of temporal pattern generation with LAVA boards enables intricate studies of Wnt signaling thresholds and timing of signaling oscillations during development.

The resolution of LAVA board spatial patterning and spatially localized mesendoderm differentiation were quantified and used to mimic the Wnt morphogen gradients present in the early mammalian embryo. Patterned illumination allows for studying how the shape, size, and intensity of spatial patterns influences differentiation and morphogenesis.

Materials & Methods

LAVA Device Construction

LAVA devices are constructed using two custom printed circuit boards (PCB) designed in EAGLE (Autodesk). PCB1 contains electronics for LED control while PCB2 is the power distribution board. For 24-well illumination, PCB1 contains solder pads for a circular array of 5 LEDs per well, which are connected in series and illuminate each well through two 3D-printed light guides and a series of diffusers (optical configuration optimized in Zemax, see below). For 96-well illumination, PCB1 contains solder pads for 1 LED per well of a 96-well plate; given the 24-channel LED driver, independent illumination control is possible for each group of 4 wells. For each channel, the ground wire connects to TLC5947 driver and is modulated with pulse-width modulation, while the positive terminal connects to the power plane of PCB1. PCB1 also contains headers for electrical connection to cooling fans. A heatsink mounts onto the bottom of PCB1, using thermally conductive adhesive (Arctic Silver, ASTA-7G), in a region without silk screen and thermally conductive electrical vias that draw heat away from surface-mount LEDs.

In PCB2, a power supply connects through a barrel power jack to power the LEDs through an LED driver (TLC5947, Adafruit). Power is also supplied to three fans and the Raspberry Pi microcontroller through switching voltage regulators.

On top of PCB1, optical assembly and tissue culture plate is mounted in such a way that tissue culture plate is illuminated from the bottom. It is critical that tissue culture plate is made of black, opaque plastic a thin, 170 µm coverslip bottom (Eppendorf Cell Imaging Plate, 24-well) to avoid light bleed-through between wells and high spatial patterning resolution. The LED driver, PCB2, and the Raspberry Pi microcontroller are all mounted and electrically connected to PCB1, and the entire assembly is mounted onto an acrylic laser-cut base through vibration-dampening mounts. The base contains rubber footpegs to reduce static or electrical shorting with the tissue culture incubator racks.

Zemax Modeling and Optimization of LAVA Well

The ray-tracing software Zemax OpticStudio was used in Non-Sequential mode to model illumination of a 24-well plate. Based on modeling results, the optimized configuration parameters are as follows: 5 surface-mount LEDs are symmetrically radially distributed around a 5 mm-radius circle; diameter of each light guide is 16.5 mm; one 80° circular optical diffusers placed between the two light guides, another placed onto the top light guide (i.e. between light guide and tissue culture plate); thickness of each light guide is 1.5 cm; light guides are manufactured from black 3D-printed acrylic.

Software Control and Graphical User Interface

The LEDs are controlled by an Adafruit 24-Channel 12-bit PWM LED driver with an SLI interface to a Raspberry Pi Zero W. The 12-bit PWM results in LEDs that are capable of 4096 unique illumination levels over their given operating range. For ease of use, a GUI has been written in Java and is conveniently packed into an executable application file. This interface allows for independent control of each of the 24 channels. To accommodate for the variety of experimental conditions, each LED can be programmed to a constant illumination, a blinking pattern, or a series of linear and sinusoidal patterns. Since each board has slightly different intensity characteristics, the intensity to PWM calibration parameters are input at runtime. Sinusoidal and linear functions are interpolated at a frequency of 1 Hz whereas blinking patterns have been tested up to 100 Hz. Since the LED board's USB port may be inaccessible during certain experiments, it is possible to wirelessly upload new illumination settings from any WIFI capable computer.

Upon booting the Raspberry Pi, a C++ script executes, checking the device for previous illumination settings and resumes the patterned illumination. The Pi polls for new illumination settings every few seconds, so the changes of a newly uploaded pattern will be reflected without an additional reboot. It should be noted that the decision to use C++ was motivated by a desire to break through certain speed limitations posed by an interpreted language's rate of execution. A Python implementation was completed, but only the compiled C++ version is able drive all 24 channels at the desired refresh rate.

FIG. 1, Panels A-C. Overview of illumination device, LAVA, for optogenetic stimulation of hESC cultures. Panel A) Schematic of optogenetic typical experiment, where spatiotemporal control is conferred through patterning of light Panel B) Diagram of illumination device design. LEDs illuminate a tissue culture plate placed on top of device, with light passing through a series of two light guides, two optical diffusers, and a die-cut mask. LEDs are programmed through a Raspberry Pi and LED driver, and cooled with a heatsink and cooling fans. Panel C) Image of assembled device, with optical, cooling, and electronics subsystems highlighted.

FIG. 2, Panels A-C. Optical design for illumination uniformity of tissue culture wells. Panel A) Schematic of Zemax model used for system optimization Panel B) Brightfield images of well (left) and graph of intensity linescans along indicated cross-sections (right) characterize the intensity uniformity of the illumination device under two configurations, where light guide thickness d is either (1) 1 cm, top green or (2) 1.5 cm, bottom purple. Percent decrease is calculated between intensity at center of well and intensity at highlighted red point, which indicates location of well edge of a 24-well culture plate (average of 4 independent wells). Scale bar 2.5 mm. Panel C) Light intensity (irradiance, µW/mm) in response to the programmed duty cycle of the pulse-width modulation signal. Graph shows intensity measured from each of the 24 channels, as well as the curve fitting to a linear regression model.

FIG. 3, Panels A-D. Optogenetic induction of Bra expression is light-dose responsive. Panel A) Schematic of optoWnt system. In the dark, Cry2 molecules are diffuse, while light illumination induces clustering of LRP6c, stabilizing β-catenin and transcription of target genes. Panel B) Immunostaining for LRP6 (left) and quantification of cluster number per hESC in response to increasing light intensity after 1 hr illumination. Graph shows individual cell quantification (black dot) and violin plot of distribution (blue). Scale bar 25 µm. Panel C) Immunostaining for Brachyury in response to increasing light intensity after 24 hr illumination or 3 µM CHIR treatment. Scale bar 25 µm. Panel D) Flow cytometry of optoWnt hESCs expressing eGFP reporter for Bra in response to light stimulation or treatment with Wnt pathway agonists (Wnt3a recombinant protein or CHIR). Graph shows percent cGFP positive cells and nonlinear least squares fit to increasing exponential decay curve. Graph shows mean±1 s.d., n=3 replicates.

FIG. 4, Panels A-D. Characterization of temporal control using LAVA devices. Panel A) Schematic of temporal light patterning. Panel B) Well intensity as a function of time of various waveforms programmed through LAVA GUI. Programmed values shown in black, measured intensity in green. Panel C) Error in measured pulsewidths relative to programmed pulsewidth. Panel D) OptoWnt hESCs were illuminated for varying lengths of time followed by flow cytometry as fixed endpoint. Graph shows histograms of eGFP reporter for endogenous Bra/T activity for each illumination condition. Cell count histograms normalized to total cells per condition (~30,000 cells).

FIG. 5, Panels A-F. OptoWnt induces epithelial to mesenchymal transition and primitive streak-like behavior Panel A) Schematic of spatial light patterning Panel B) Stitched brightfield and fluorescence images of OptoWnt hESCs illuminated with UC Berkeley (Cal) logo mask and immunostained for LRP6. Clusters of LRP6 are observed in illuminated region (orange inset) but not in masked region (yellow inset). Scale bar 100 µm (top), 1 mm (bottom). c) Quantification of light scattering through bottom of tissue culture plate shows a ~50 µm spread (full width at half max, red line) of hESC OptoWnt clusters outside of projected pattern (orange line). Brightfield image of mask (top), fluorescence image of immunostaining for LRP6 (middle), and quantification of LRP6 cluster count (bottom). Insets (1) and (2) show masked, unclustered and illuminated, clustered regions, respectively. Scale bars 100 µm. Panel D) Patterned illumination with 500 µm are of light. Brightfield image (left panel) with overlay of light pattern shows migratory cells with mesenchymal morphology outside of region of illumination (white arrows). Immunostaining for Bra and total β-catenin (middle panel) and Oct4 and Slug (right panel) with overlay of light pattern (yellow line). Greyscale zoom-in of highlighted region (white box) shows migratory cells. Scale bars 200 µm. e) Patterned illumination with 1.5 mm diameter circle of light. Immunostaining for Bra shows expression in region of mask (left panel). Confocal z-stacks (middle panel) of bottom cell layer (Z=2.4 µm), middle (Z=20.8) and top (Z=47.2) show migrating cells diving beneath epithelial cell layer. Z-slice through along highlighted line (green). Panel F) Quantification of cell migration beyond region of mask illumination in (Panel E). Graph shows mean±1 s.d., n=3 replicates. Student's t-test (two-tail). Scale bars 200 µm.

FIG. 6. System block diagram of LAVA device.

Figure 7:
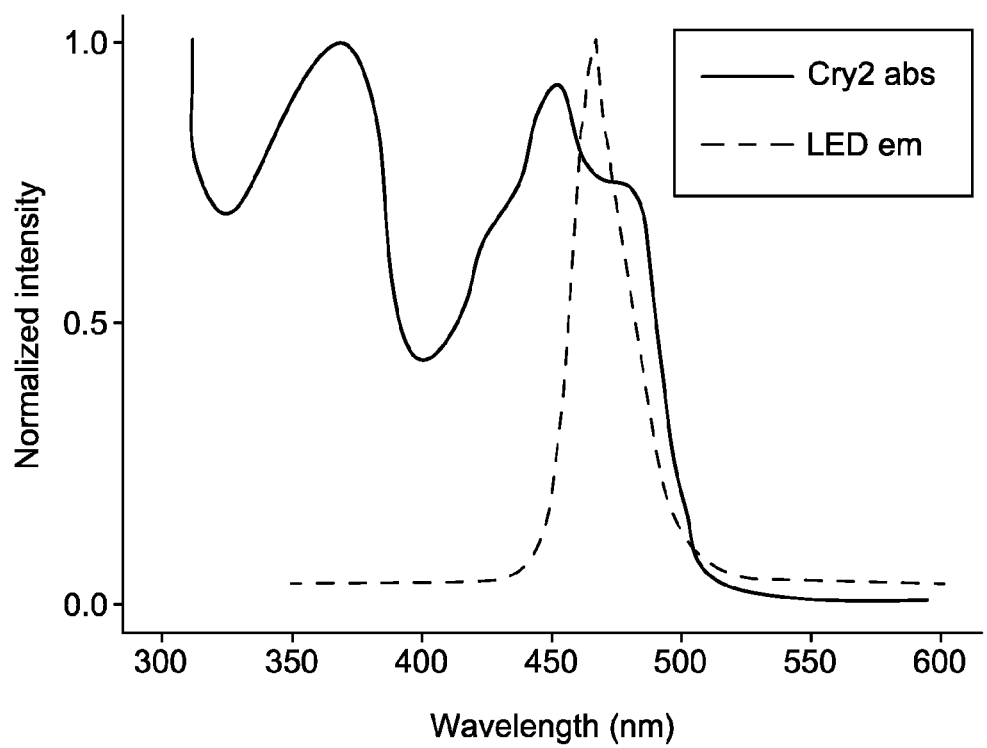
FIG. 7. Emission spectrum of 470 nm blue LEDs matches absorption spectrum of Cry2. Cry2 spectrum adapted from reference.
Figure 8B:
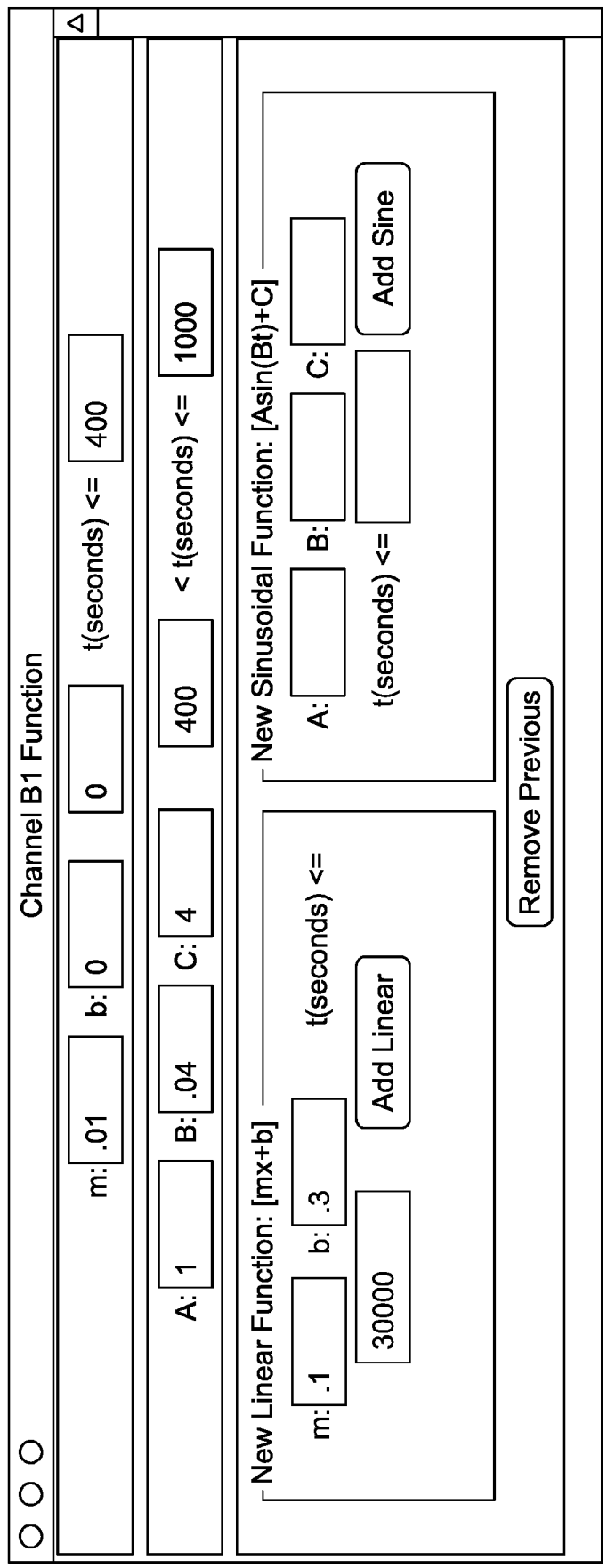
FIG. 8, Panels A-B. Screenshot of GUI for illumination device control. User can input parameters for desired intensities, blinking sequences, or temporal functions for each individual well and upload settings wirelessly to the device.
Figure 9C:
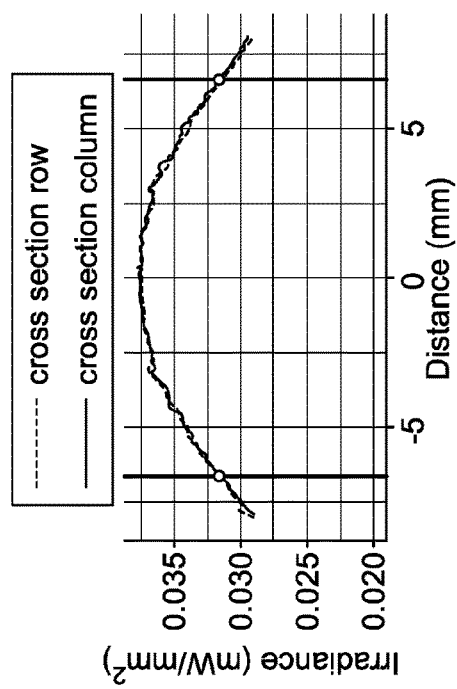
FIG. 9, Panels A-H. Validation of Zemax ray tracing model.
Figure 9C:
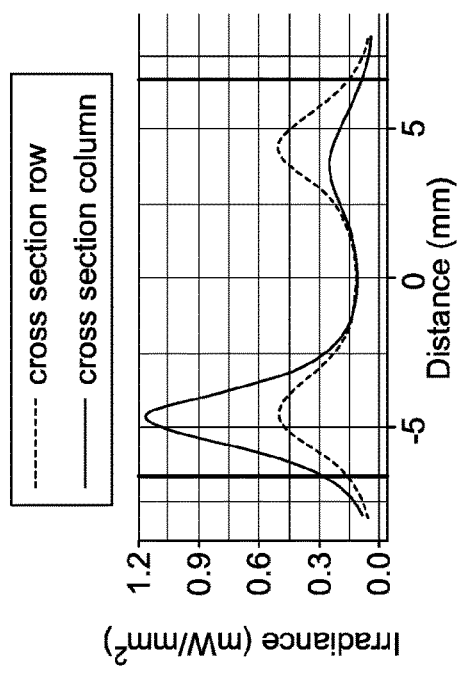
Figure 9C:
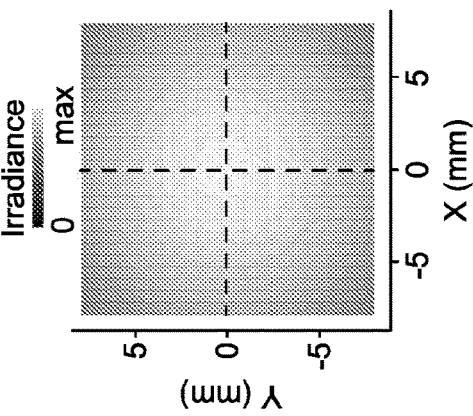
Figure 9C:
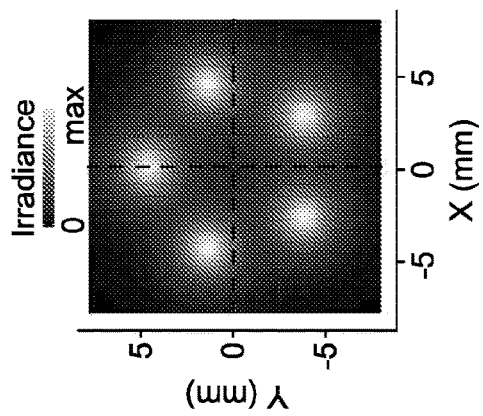
Figure 9D:
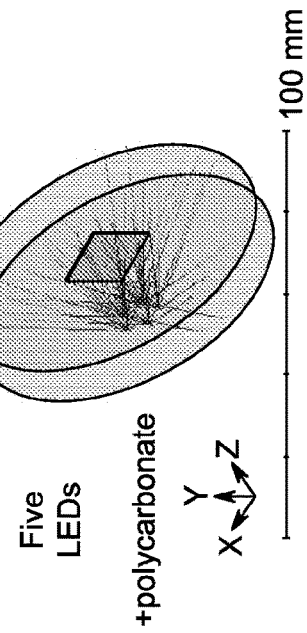
Figure 9D:
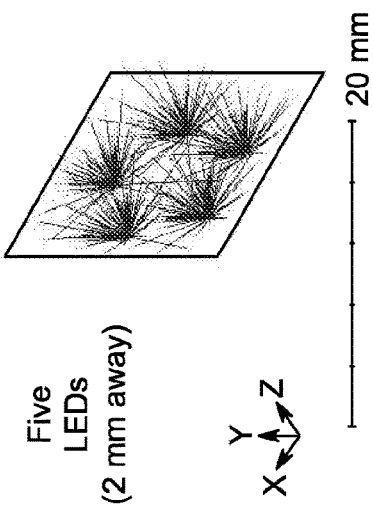
Figure 9E:
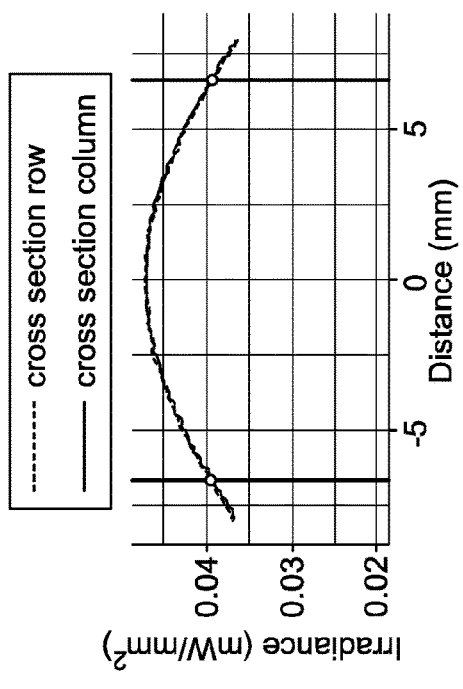
Figure 9E:
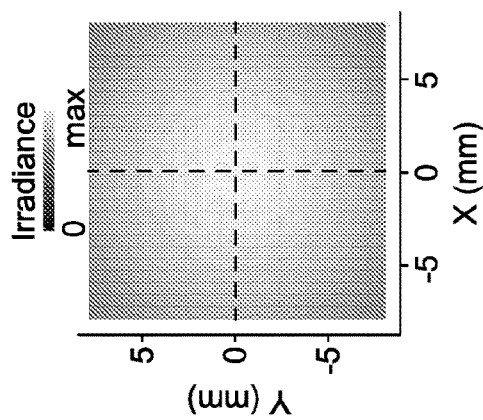
Figure 9F:
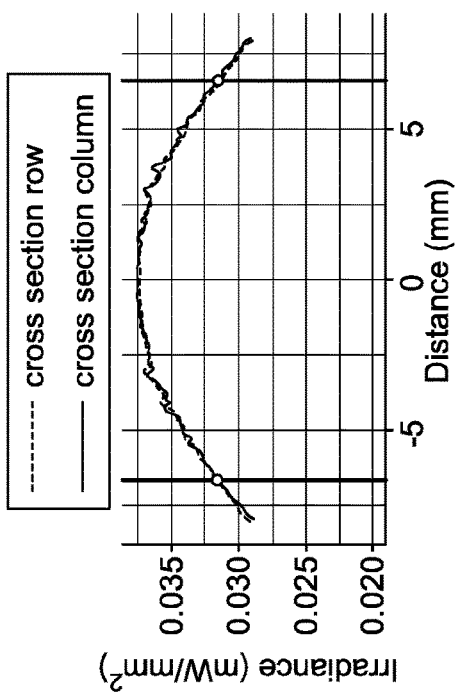
Figure 9F:
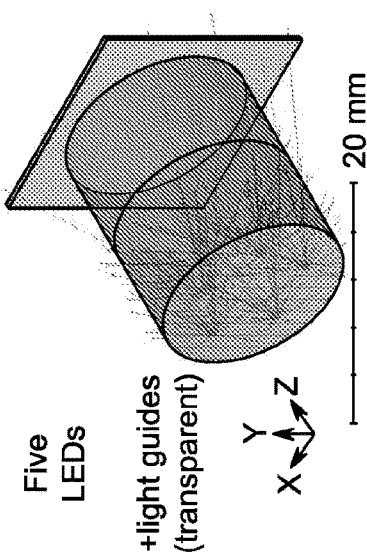
Figure 9G:
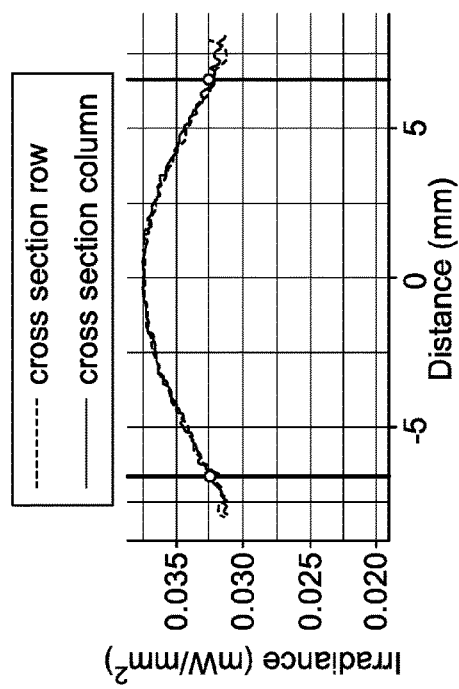
Figure 9G:
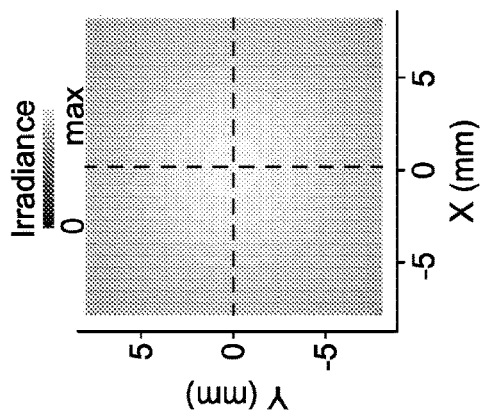
Figure 9G:
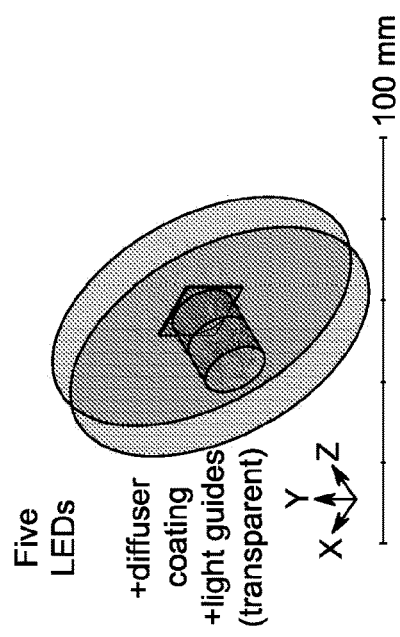
Figure 9H:
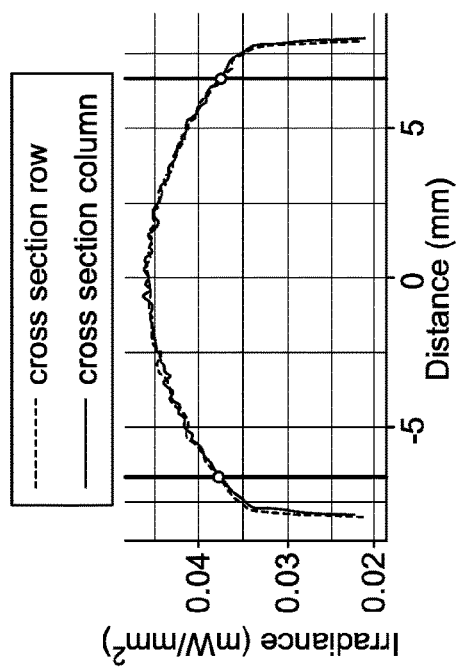
Figure 9H:
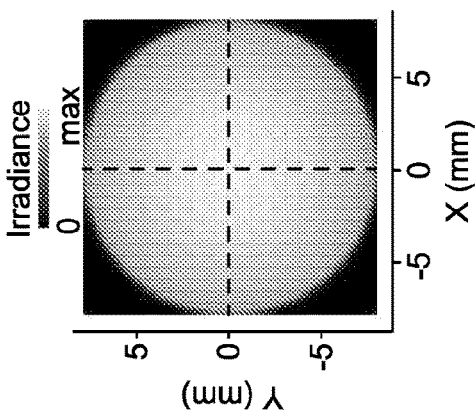
Figure 9H:
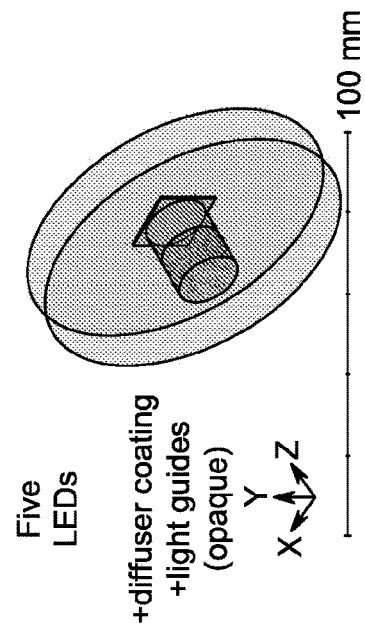
Figure 10A:
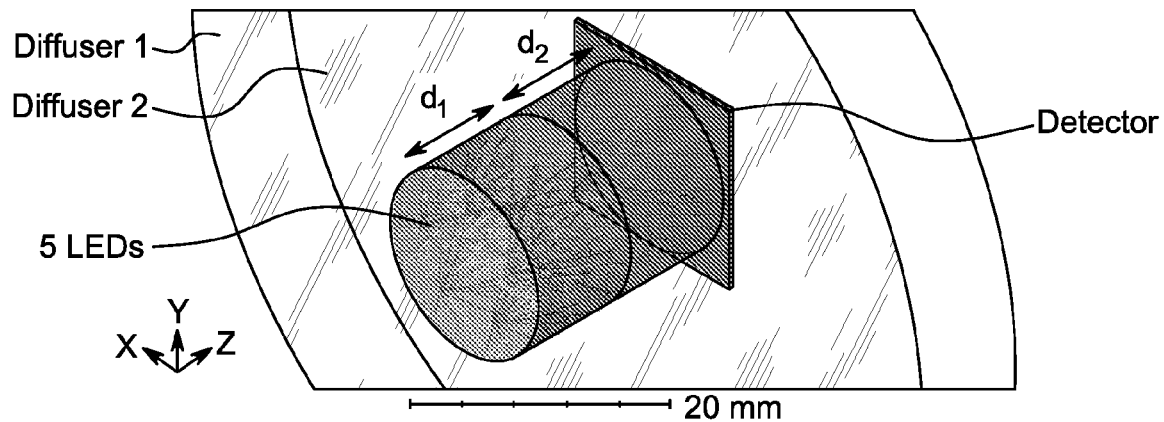
FIG. 10, Panels A-E. Results of Zemax modeling at variable light guide thicknesses, $d_1$ and $d_2$.
Figure 10B:
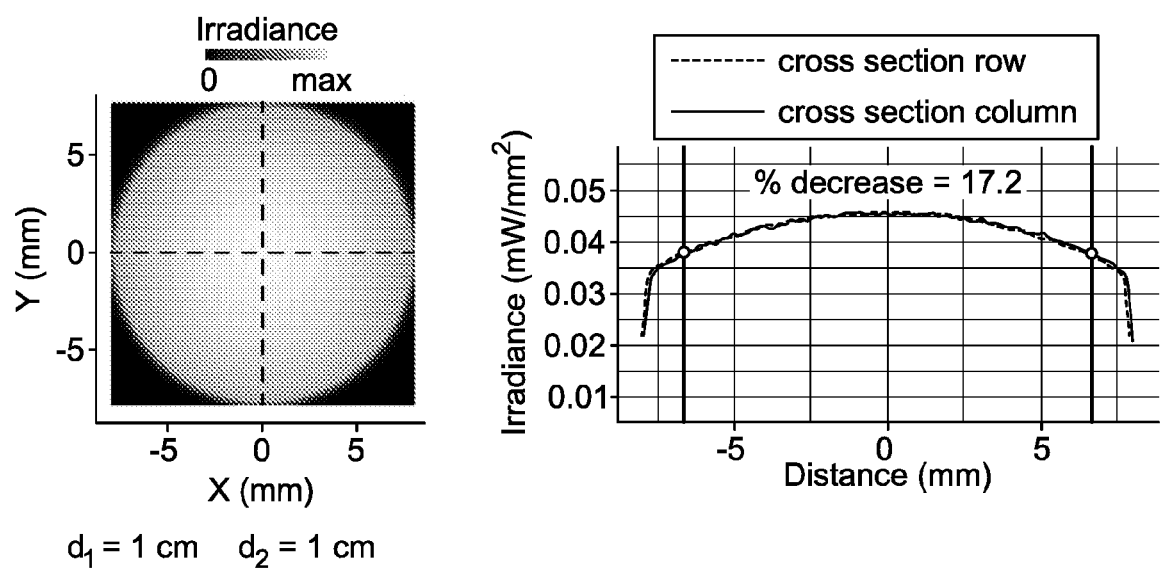
Figure 10C:
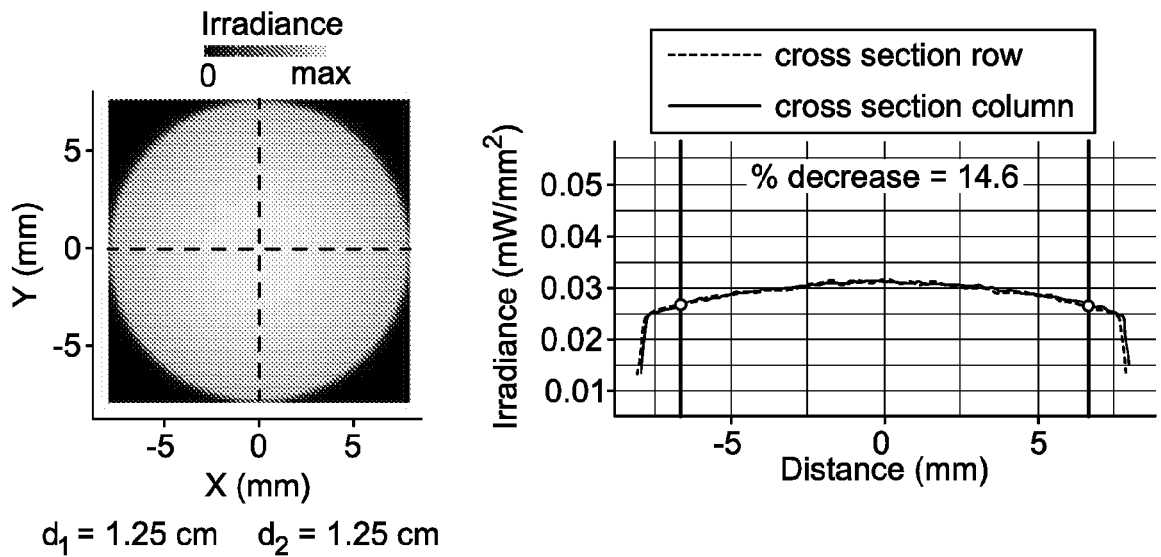
Figure 10D:
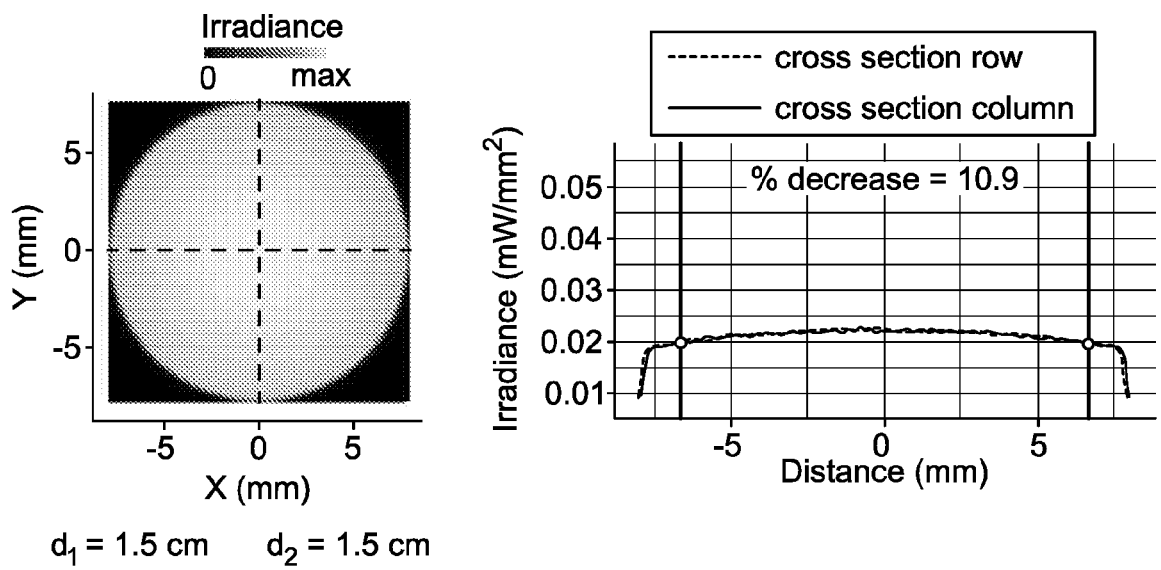
Figure 10E:
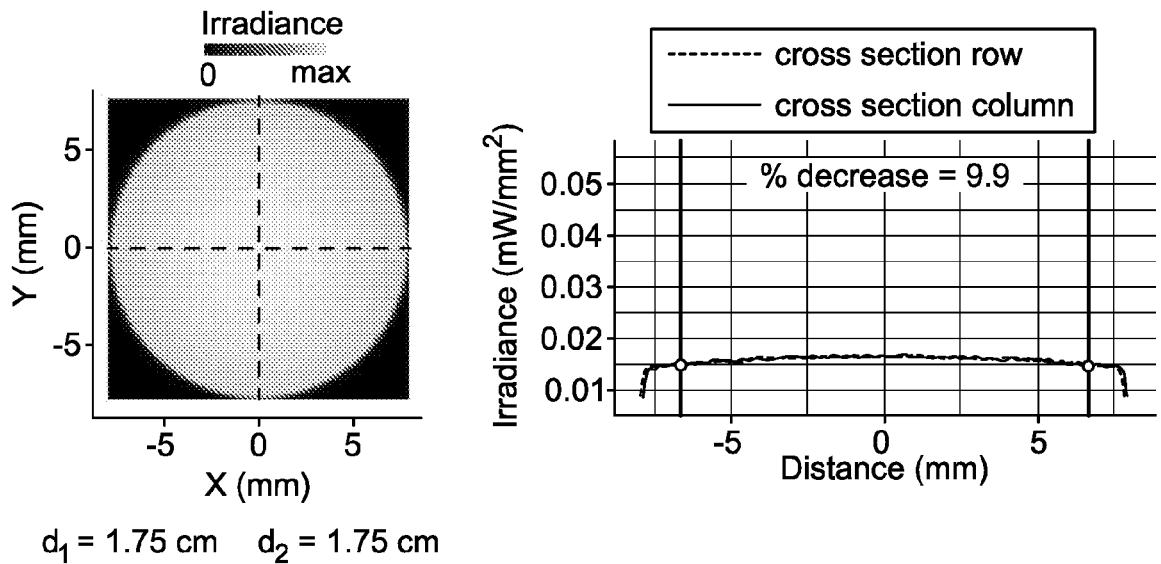

FIG. 7. Emission spectrum of 470 nm blue LEDs matches absorption spectrum of Cry2.

FIG. 8, Panels A-B. Screenshot of GUI for illumination device control. User can input parameters for desired intensities, blinking sequences, or temporal functions for each individual well and upload settings wirelessly to the device.

FIG. 9, Panels A-H. Validation of Zemax ray tracing model. Schematic of LED configuration (left), modeling result at detector plane (middle), and column and row cross-sections (right) with well edge of 24-well plate indicated with red points. Panel A) Single LED illuminating detector 21 mm away. Panel B) Five LEDs, distributed along 1 cm diameter circle, illuminating detector 21 mm away. Panel C) Five LEDs illuminating detector 2 mm away. Panel D) Five LEDs illuminating detector 21 mm away through two 0.01" thick sheets of polycarbonate. Panel E) Five LEDs illuminating detector 21 mm away through two 10 mm transparent light guides. Panel F) Five LEDs illuminating detector 21 mm away through two 0.01" thick sheets of polycarbonate and two 10 mm transparent light guides. Panel G) Five LEDs illuminating detector 21 mm away through two 0.01" thick sheets of polycarbonate with 80° diffuser coating and two 10 mm transparent light guides. Panel H) Five LEDs illuminating detector 21 mm away through two uncoated 0.01" thick sheets of polycarbonate and two 10 mm reflective light guides with Lambertian scattering.

FIG. 10, Panels A-E. Results of Zemax modeling at variable light guide thicknesses, $d_1$ and $d_2$. Panel A) Schematic of modeling setup. Five LEDs illuminate detector through two 0.01" thick sheets of polycarbonate with 80° diffuser coating (red) and two reflective light guides with Lambertian scattering (grey cylinder). Panel B-E) Modeling results at indicated values of $d_1$, $d_2$. Image at detector plane (left) and column and row cross-sections (right) with well edge of 24-well plate indicated with red points show improved illumination uniformity at expense of light intensity with increasing light guide thickness.

FIG. 11. Coefficient of variation of light intensity between the 24 independent light channels measured at different programmed intensities. Green points correspond to optical configuration with d=1 cm, violet points show optical configuration with d=1.5 cm.

FIG. 12, Panels A-B. Panel A) Immunostaining quantification for average Bra intensity per hESC in response to increasing light intensity after 24 hr illumination or 3 µM CHIR treatment. Graph shows mean±1 s.d., n=3 replicates. Panel B) Flow cytometry histograms of optoWnt hESCs expressing eGFP reporter for Bra after 24 hr illumination at varying light intensities. Graph shows sum of n=3 replicates.

FIG. 13, Panels A-D. Phototoxicity during continuous optogenetic stimulation of hESC cultures. Panel A) Temperature of media after 24 hrs of continuous illumination Panel B) Brightfield images (top) of live wild-type hESC cultures illuminated at indicated light intensities for 48 hrs and flow cytometry results for Annexin V and propidium iodide (PI) stain. Scale bar 250 µm. Panel C) Quantification of apoptosis marker Annexin V and dead cell stain PI shows a significant increase in apoptosis and cell death above 1 µW/mm$^2$ illumination intensity ($p_A$=0.002, $p_{PI}$=0.001 0-1 µW/mm$^2$ and $p_A$=0.0005, $p_{PI}$=0.0005 0-2 µW/mm$^2$). No difference was observed between 0 and 0.5 µW/mm$^2$ ($p_A$=0.78, $p_{PI}$=0.50). ANOVA followed by Tukey test. Graph shows mean±1 s.d., n=3 replicates. Panel D) Representative fluorescence images (left) and quantification (right) of wild-type hESCs stained for pluripotency markers Sox2, Nanog, Oct4, and differentiation marker Brachyury (Bra/T) after 48 hr illumination at 0.8 µW/mm$^2$. Student's t-test (two-tail). Graph shows mean±1 s.d., n=3 replicates. Scale bar 25 µm.

FIG. 14. Illumination power meter measurements of programmed blinking sequences show signal inaccuracy at 1 ms pulses. Voltage signal from power meter measured with oscilloscope and is proportional to irradiance.

FIG. 15, Panels A-C. Panel A) Images of adhesive die-cut masks applied using transfer tape (top) onto 24-well cell culture plate (bottom). Panel B) Brightfield images of die-cut mask illustrate resolution limit of cutter. Scale bar 3 mm. Panel C) Schematic of light scattering from photomask.

FIG. 16. Screenshot of Zemax model parameters of LAVA well, optimized for uniform 24-well illumination.

Figure 17A:
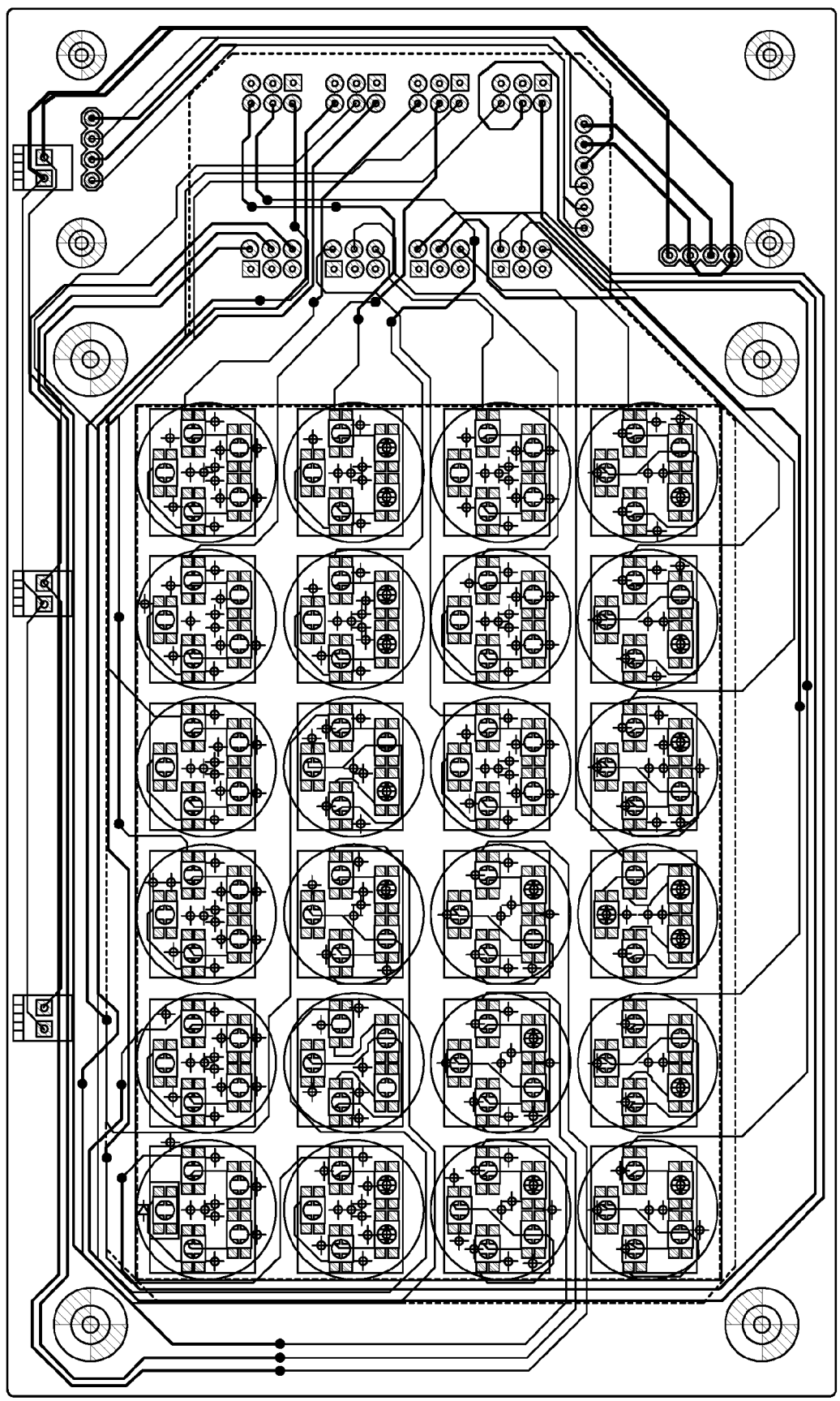
FIG. 17. Circuit board layout (top) and schematic (bottom) for 24-well LAVA device, PCB1.
Figure 17B:
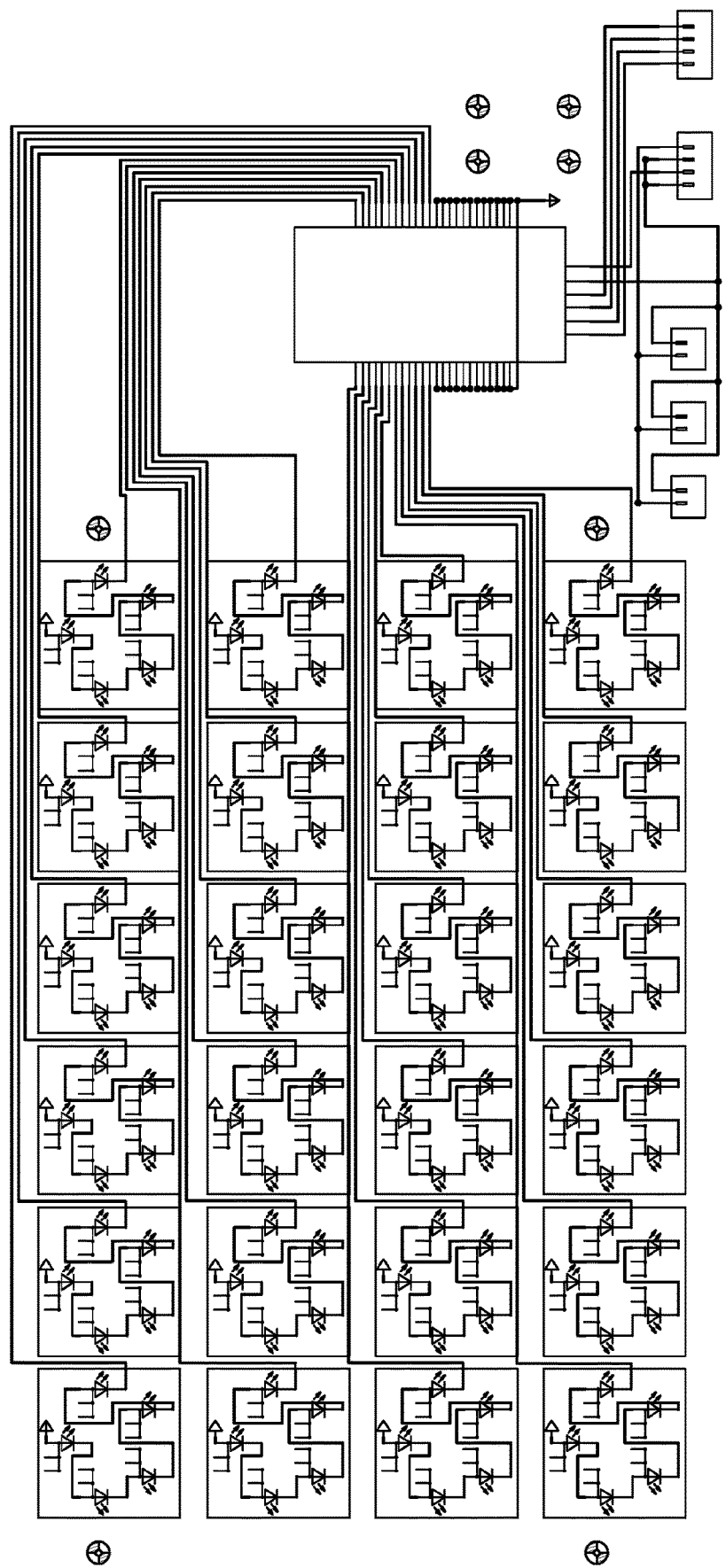

FIG. 17. Circuit board layout (top) and schematic (bottom) for 24-well LAVA device, PCB1.

Figure 18A:
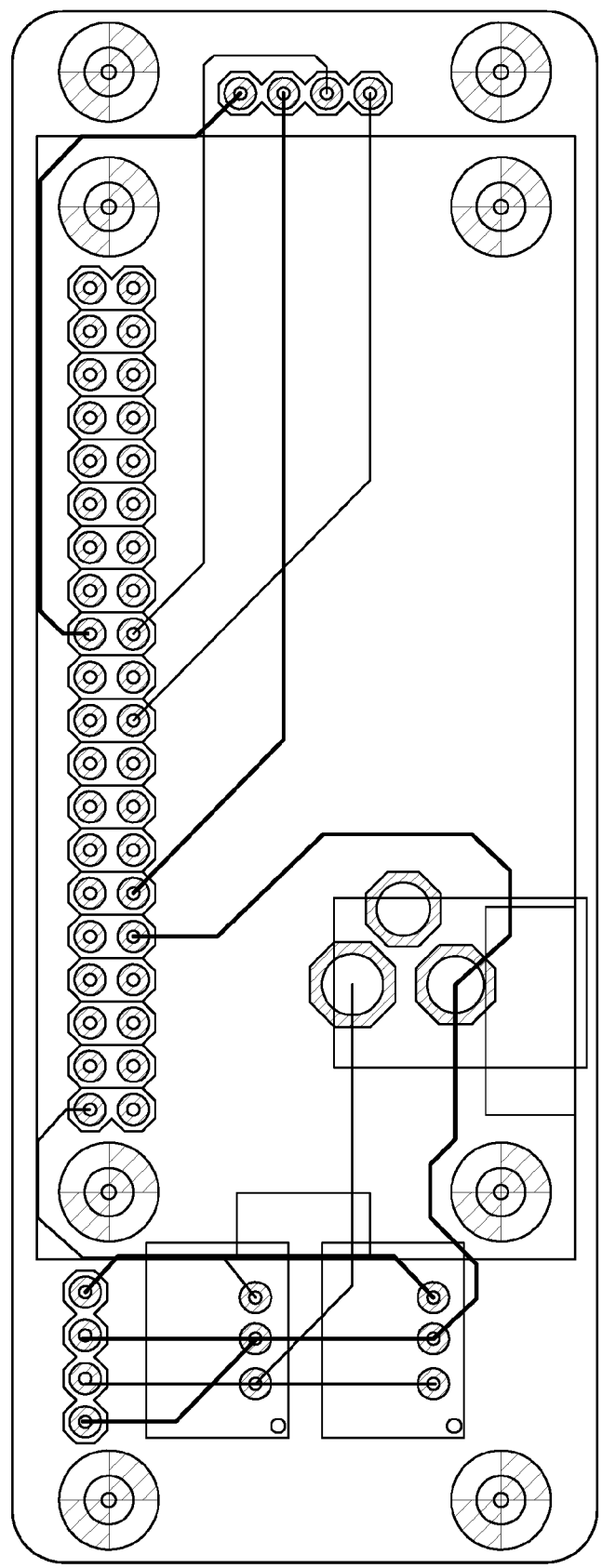
FIG. 18. Circuit board layout (top) and schematic (bottom) for LAVA device power distribution, PCB2.
Figure 18B:
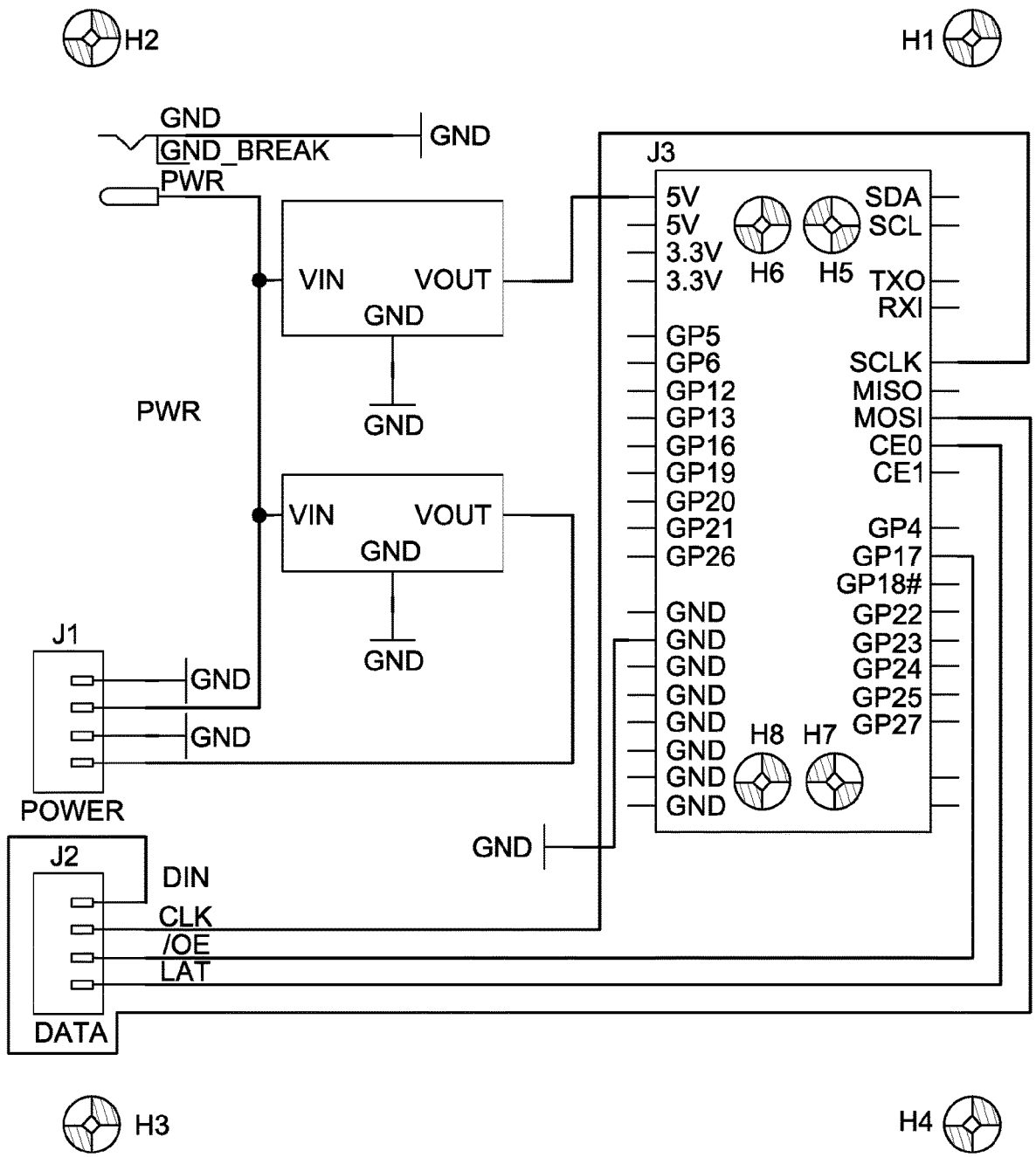

FIG. 18. Circuit board layout (top) and schematic (bottom) for LAVA device power distribution, PCB2.

Figure 19A:
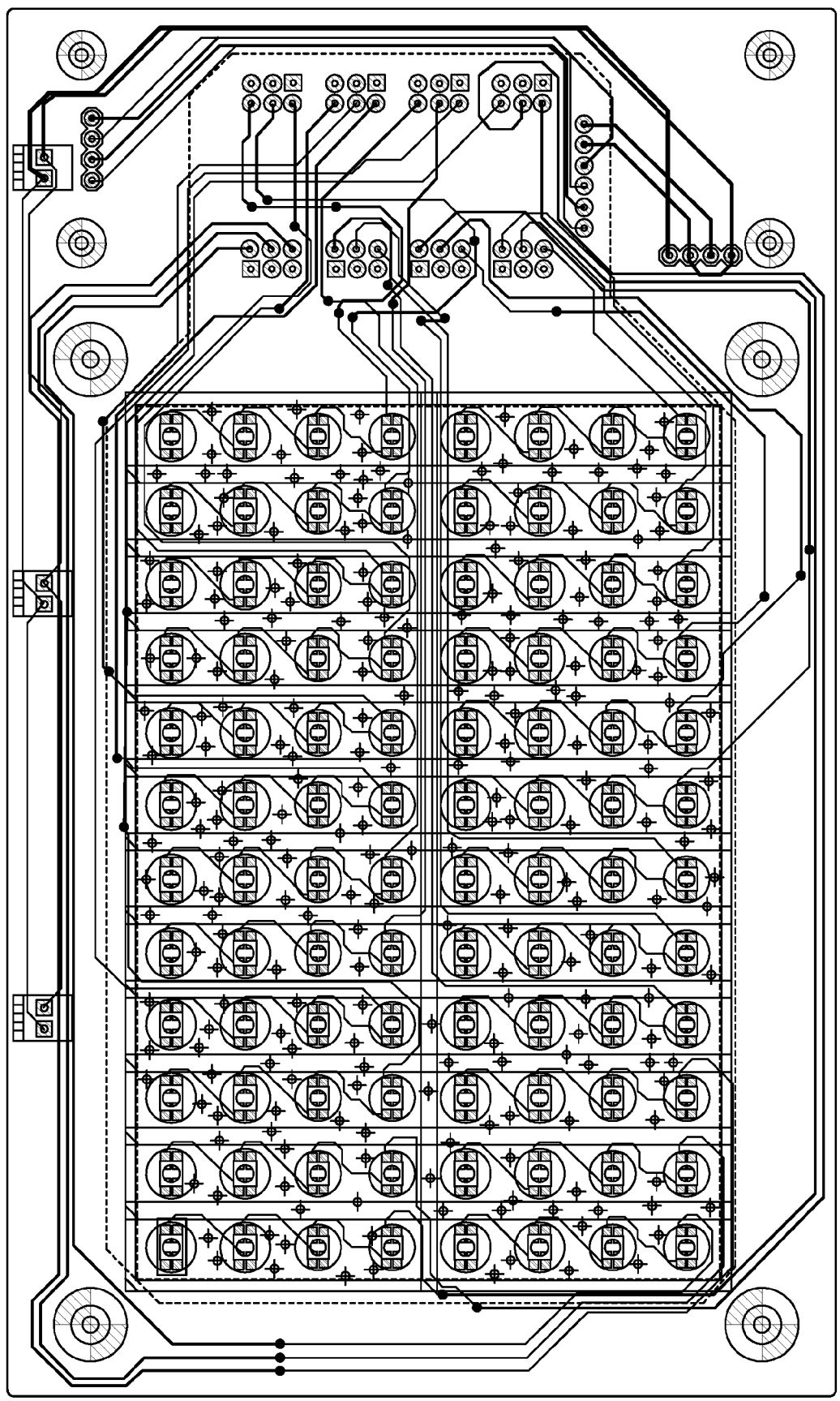
FIG. 19. Circuit board layout (top) and schematic (bottom) for 96-well LAVA device, PCB1.
Figure 19B:
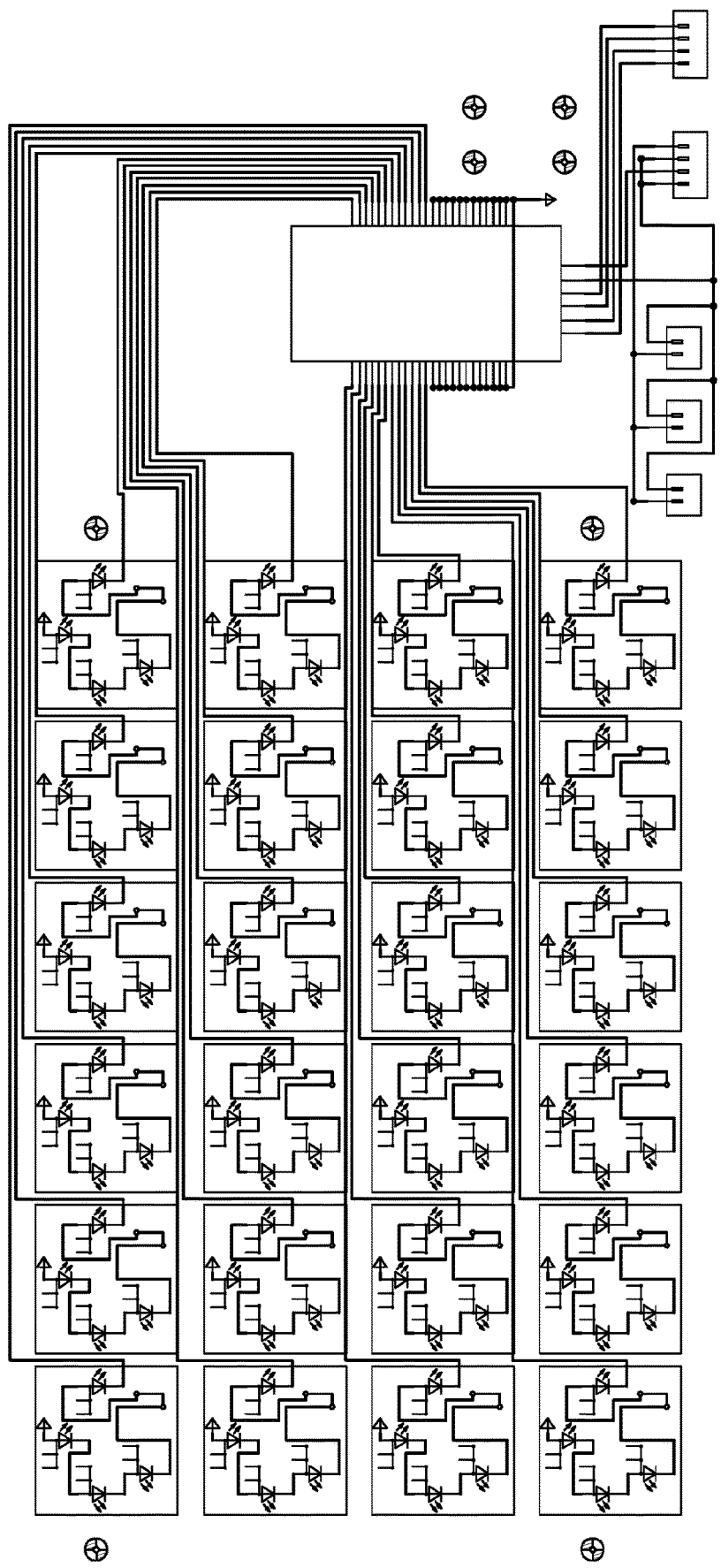

FIG. 19. Circuit board layout (top) and schematic (bottom) for 96-well LAVA device, PCB1.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for spatially and temporally controlling stem cell or progenitor cell signaling, differentiation, or both, the method comprising:
   (a) providing or obtaining a plurality of stem cells or progenitor cells, wherein at least one cell of the plurality of stem cells or progenitor cells is genetically engineered to express a light-activatable protein involved in a cell signaling or cell differentiation pathway; and
   (b) spatially and temporally illuminating the at least one cell of the plurality of stem cells or progenitor cells with light using one or more illumination parameters to activate the light-activatable protein,
   wherein the illuminating comprises illuminating a first subset of the plurality of stem cells or progenitor cells with light at a first wavelength, and illuminating a second subset of the plurality of stem cells or progenitor cells with light at a second wavelength,
   thereby spatially and temporally controlling stem cell or progenitor cell signaling, differentiation, or both.

2. The method of claim 1, wherein the one or more illumination parameters comprises one or more of: an illumination intensity, an illumination duration, an illumination pattern, an illumination wavelength, and any combination thereof.

3. The method of claim 2, wherein the illumination intensity is below an amount that causes phototoxicity in the plurality of stem cells or progenitor cells.

4. The method of claim 2, wherein the illumination intensity is from about 0.005 µW/mm$^2$ to about 20 µW/mm$^2$.

5. The method of claim 2, wherein the illumination pattern is a pulsing pattern, a sinusoidal pattern, a linear pattern, a blinking pattern, or any combination thereof.

6. The method of claim 1, wherein the illuminating comprises illuminating the plurality of stem cells or progenitor cells with light at a wavelength sufficient to activate the light-activatable protein in the at least one cell.

7. The method of claim 1, wherein an amount of activated light-activatable protein is controlled by the one or more illumination parameters.

8. The method of claim 1, wherein the light-activatable protein is selected from the group consisting of: a cryptochrome, a photoactive yellow protein (PYP) photosensor, a photoreceptor of blue light using flavin adenine dinucleotide (BLUF), a light, oxygen or voltage sensing (LOV) domain, and a phytochrome.

9. The method of claim 1, wherein the light-activatable protein is a light-inducible dimerizer.

10. The method of claim 9, wherein the light-activatable dimerizer is selected from the group consisting of: a CRY2/CIB system, a Phy/Pif system, and a BphP1/PpsR2 system.

11. The method of claim 1, wherein the illuminating comprises uniformly illuminating at least a subset of the plurality of stem cells or progenitor cells.

12. The method of claim 1, wherein the illuminating comprises independently illuminating at least one cell of the plurality of stem cells or progenitor cells with light.

13. The method of claim 1, wherein the plurality of stem cells or progenitor cells are on a multi-well plate.

14. The method of claim 1, wherein the plurality of stem cells or progenitor cells are on a tissue culture plate.

15. The method of claim 1, wherein the method results in spatial and temporal differentiation of the plurality of stem cells or progenitor cells.

16. The method of claim 1, wherein the illuminating comprises illuminating the plurality of stem cells or progenitor cells with a light pulse.

17. The method of claim 1, wherein the one or more illumination parameters comprises an illumination duration, and wherein the illumination duration is about 0.5 ms or more.

18. The method of claim 1, wherein the one or more illumination parameters comprises a pulsing frequency, and wherein the pulsing frequency is about 1 Hz or more.

19. The method of claim 1, wherein the one or more illumination parameters comprises an illumination duration, and wherein the illumination duration is about 1 minute or more.

* * * * *